US010679739B2

(12) United States Patent
Nearhood et al.

(10) Patent No.: US 10,679,739 B2
(45) Date of Patent: Jun. 9, 2020

(54) MANAGEMENT OF IMPLANTABLE CARDIAC DEVICE INTERROGATION DATA AND REPORTS

(71) Applicants: Rachel Marie Nearhood, Minneapolis, MN (US); Jeremy Scot Martinson, Los Angeles, CA (US); GilAnthony Daral Ungab, San Diego, CA (US); Stephen Matthew Sjoberg, San Diego, CA (US)

(72) Inventors: Rachel Marie Nearhood, Minneapolis, MN (US); Jeremy Scot Martinson, Los Angeles, CA (US); GilAnthony Daral Ungab, San Diego, CA (US); Stephen Matthew Sjoberg, San Diego, CA (US)

(73) Assignee: Geneva Healthcare, LLC, Malvern, PA (US)

( * ) Notice: Subject to any disclaimer, the term of this patent is extended or adjusted under 35 U.S.C. 154(b) by 907 days.

(21) Appl. No.: 14/705,498

(22) Filed: May 6, 2015

(65) Prior Publication Data

US 2015/0324549 A1   Nov. 12, 2015

Related U.S. Application Data

(60) Provisional application No. 61/990,064, filed on May 7, 2014.

(51) Int. Cl.
*G16H 15/00* (2018.01)
*G16H 80/00* (2018.01)
*G16H 40/63* (2018.01)

(52) U.S. Cl.
CPC ............. *G16H 15/00* (2018.01); *G16H 80/00* (2018.01); *G16H 40/63* (2018.01)

(58) Field of Classification Search
CPC ...... G06Q 10/06; G06Q 10/105; G16H 15/00; G16H 10/60
See application file for complete search history.

(56) References Cited

U.S. PATENT DOCUMENTS 5,319,363 A   6/1994  Welch et al.
D605,652 S   12/2009 Plaisted et al.
(Continued)

FOREIGN PATENT DOCUMENTS

EP               1 310 272 A2      5/2003
WO      WO-2012068223 A1 *  5/2012  ............. G06Q 50/22

OTHER PUBLICATIONS

International Search Report and Written Opinion for Application No. PCT/US2015/029499 dated Sep. 8, 2015.
(Continued)

*Primary Examiner* — John P Go
(74) *Attorney, Agent, or Firm* — Merchant & Gould P.C.

(57) ABSTRACT

An interrogation data management system operates to manage implantable cardiac device interrogation data and reports. In one example the system generates a report including a reading physician note, a summary report, and an implantable cardiac device manufacturer's report. Some embodiments include smart routing, to automatically route interrogation data reports to medical professionals based on predetermined rules. The interrogation data management system interacts with the reading physician to formally review the interrogation data reports and to generate a reading physician note. The reading physician note includes the reading physician's findings/interpretations and conclusions. Other aspects are also described in this disclosure.

13 Claims, 73 Drawing Sheets

(56) References Cited

U.S. PATENT DOCUMENTS

| | | |
|---|---|---|
| D667,418 S | 9/2012 | LoBosco et al. |
| 2001/0039504 A1 | 11/2001 | Linberg et al. |
| 2002/0120676 A1 | 8/2002 | Biondi et al. |
| 2003/0018822 A1 | 1/2003 | Robb et al. |
| 2003/0126195 A1 | 7/2003 | Reynolds et al. |
| 2004/0158132 A1 | 8/2004 | Zaleski |
| 2004/0172284 A1* | 9/2004 | Sullivan ................. G06Q 10/10 705/2 |
| 2005/0060187 A1 | 3/2005 | Gottesman |
| 2005/0192838 A1 | 9/2005 | Jones et al. |
| 2006/0020492 A1* | 1/2006 | Cousineau ............ G06F 17/278 705/2 |
| 2006/0241907 A1 | 10/2006 | Armstrong et al. |
| 2008/0021741 A1* | 1/2008 | Holla ..................... G06Q 50/22 705/3 |
| 2008/0127052 A1 | 5/2008 | Rostoker |
| 2008/0243539 A1* | 10/2008 | Barish .................. G06F 19/321 705/2 |
| 2008/0288317 A1 | 11/2008 | Kakar |
| 2009/0094086 A1 | 4/2009 | Bruno et al. |
| 2009/0144088 A1* | 6/2009 | Zubiller ............... G06Q 20/102 705/3 |
| 2009/0204435 A1* | 8/2009 | Gale .................... G06F 19/3418 705/3 |
| 2011/0145018 A1* | 6/2011 | Fotsch .................. G06F 19/326 705/3 |
| 2011/0154241 A1 | 6/2011 | Skidmore et al. |
| 2013/0018674 A1* | 1/2013 | Bedi ...................... G06Q 10/00 705/3 |
| 2013/0111319 A1 | 5/2013 | Lin et al. |
| 2013/0132142 A1* | 5/2013 | Wood-Salomon ..... G06Q 10/10 705/7.15 |
| 2013/0317852 A1* | 11/2013 | Worrell ............... G06F 19/3418 705/3 |

OTHER PUBLICATIONS

Patent Cooperation Treaty International Searching Authority, International Search Report and Written Opinion for PCT/US2013/041598 dated Oct. 7, 2013, 9 pages.

\* cited by examiner

Status: Preliminary

PATIENT NAME: ACKERMAN, KENDRA
D.O.B.: 02-FEB-1948
MRN #: 101-593-814
VISIT #: 61527632
LOCATION: SHARP CHULA VISTA ED

INTERROGATED: 20-MAR-14, 22:05
UPLOADED: 20-MAR-14, 22:10
REASON FOR INTERROGATION:
SHORTNESS OF BREATH, DIZZINESS

BATTERY STATUS

| | |
|---|---|
| BATTERY STATUS: | MOL (MIDDLE OF LIFE) |
| REMAINING LONGEVITY: | 26 MONTHS |
| MEASURED VOLTAGE: | XX V |
| MINIMUM VOLTAGE: | 3.4 < 4.5 V |
| CHARGE TIME: | 9.7 SEC |

LEAD STATUS

| | LEAD A | LEAD RV | LEAD LV |
|---|---|---|---|
| SENSE: | -- | 1.6 MV | 1.6 MV |
| IMPEDANCE: | -- | 503 OHMS | 503 OHMS |
| PACING THRESHOLD AMPLITUDE: | -- | 0.8 V | 0.8 V |
| THRESHOLD MEASUREMENT METHOD: | -- | PROGRAMMER MANUAL | PROGRAMMER MANUAL |

LEAD SETTINGS

| CHAMBER: | LEAD RA | LEAD RV | LEAD LV |
|---|---|---|---|
| SENSITIVITY: | -- | 1.3 MV (ADAPTIVE) | 1 MV (FIXED) |
| SENSING POLARITY: | -- | UNIPOLAR | UNIPOLAR |
| SENSING VECTOR: | -- | RVTIP - CAN | LVTIP - CAN |
| PACING OUTPUT: | -- | 2.0 V (ADAPTIVE) | 2.0 V (FIXED) |
| PACING PULSE WIDTH: | -- | 0.5 MS | 0.5 MS |
| PACING VECTOR*: | -- | BIPOLAR | UNIPOLAR |
| | -- | RVTIP - RVRING | LVTIP - RVRING |

SHOCK-VECTOR: RVCOIL, RACOIL - CAN
* (-) CATHODE - (+) ANODE

LEAD GENERAL INFORMATION

| | |
|---|---|
| LEAD MANUFACTURER: | [COMPANY NAME] |
| LEAD MODEL: | XXXXXXX-XX |
| LEAD SERIAL NUMBER: | XXXXXXX-XX |
| LEAD IMPLANT DATE: | 01/02/2011 |

FIG. 6B

PATIENT NAME: ACKERMAN, KENDRA
D.O.B.: 02-FEB-1948
MRN #: 101-593-814
VISIT #: 61527632
LOCATION: SHARP CHULA VISTA ED

INTERROGATED: 20-MAR-14, 22:05
UPLOADED: 20-MAR-14, 22:10
REASON FOR INTERROGATION:
SHORTNESS OF BREATH, DIZZINESS

Status: Preliminary

EPISODE COUNT — 272D

| | | |
|---|---|---|
| THERAPY COUNTS: | 5 | |
| TYPE | RECENT* | TOTAL** |
| SHOCKS DELIVERED | 3 | 3 |
| SHOCKS ABORTED | 0 | 0 |
| ANTI-TACHY PACINGS | 2 | 2 |
| RECENT EPISODES: | 1 | |
| SINCE: | 01/01/2012 | |
| TYPE | RECENT* | TOTAL** |
| ATRIAL FIBRILLATION | 1 | 1 |
| SVT | 0 | 0 |
| VF | 0 | 0 |
| VT1 | 0 | 0 |
| VT2 | 0 | 0 |

* SINCE COUNTERS LAST CLEARED: 01/01/2012, 10:30AM, ** SINCE IMPLANTATION: 01/01/2010

VT THERAPIES — 272E

VT THERAPIES: TURNED ON

| TYPE | RATE BPM | DETECTION | ANTI-TACHY PACING | SHOCKS | DETAILS |
|---|---|---|---|---|---|
| VF | 195 | 12/18 | -- | 30JX5 | STABILITY |
| FASTVT | 165 | 8 | RAMPX6 | 20JX1, 30JX5 | |
| VTMON | 145 | 12 | -- | -- | FFRW FILTER |
| AT | 190 | | | | XYZ XYZ XYZ |
| P-IEGM | -- | -- | -- | -- | XYZ |

MAGNET MODE — 272F

| | |
|---|---|
| MAGNET MODE: | ON |
| PACING: | NO EFFECT |
| TACHY: | DISABLED |

THIS PATIENT HAS AN ICD. PLACING A MAGNET OVER THE DEVICE WILL INHIBIT ALL TACHYARRHYTHMIA THERAPIES BUT WILL HAVE NO EFFECT ON THE PACEMAKER FUNCTIONALITY OF THE DEVICE.

PLEASE LIMIT ELECTROCAUTERY TO SHORT BURSTS (MAXIMUM 2 SECONDS) SINCE PACING OUTPUT WILL CONTINUE TO BE INHIBITED DURING ELECTROCAUTERY. IN PACEMAKER DEPENDENT PATIENTS, ELECTRICAL NOISE FROM ELECTROCAUTERY MAY INHIBIT PACING SIGNIFICANTLY AND LEAD TO A CLINICALLY RELEVANT DECREASE IN CARDIAC OUTPUT.

STATUS REPORT

TO: PHYSICIAN GILANTHONY UNGAB

| | EVIA DR-T (SN 66154262) | LAST MESSAGE: JUL 25, 2012 |
| | PM IMPLANTED JUN 27, 2012 | LAST CLINIC FOLLOW-UP: JUL 6, 2012 |

STATUS: NO ANOMALIES

STATUS - SUMMARY:
STATUS SUMMARY FOR PATIENT ID "HERNANDEZ ELVIRA"
AUTOMATIC REMARK: NO ANOMALIES DETECTED.

STATUS - DEVICE:

| BATTERY | |
|---|---|
| STATUS | OK |
| DATE OF IMPLANTATION | JUL 27, 2012 1:02:02 PM |
| HOME MONITORING | |
| MESSAGE TYPE | TIME TRIGGERED |
| DEVICE MESSAGE CREATED ON | JUL 25, 2012 1:02:00 AM |
| END OF LAST MONITORING INTERVAL | JUL 25, 2012 1:02:00 AM |
| TRANSMITTER | |
| TRANSMITTER SN | 48303648 |
| LAST TRANSMISSION RECEIVED ON | JUL 25, 2012 1:03:14 AM |

BATTERY STATUS

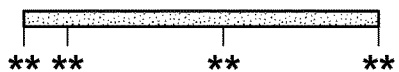

STATUS - LEAD:

| RA LEAD - SETROX S 45, BIO, IMPLANTED JUN 27, 2012 | 24H | SINCE JUL 8, 2012 1:02:00 AM MEAN VALUES, ** MIN VALUES |
|---|---|---|
| PACING IMPEDANCE [OHM] | 488 | 500 |
| PACING THRESHOLD [V] | 0.8 | 0.8 |
| LAST THRESHOLD MEASUREMENT [RA] | JUL 20, 2012 2:01:26 AM | |
| CAPTURE CONTROL STATUS | OK | |
| SENSING AMPLITUDE [DAILY MEAN] [MV] | 4.5 | 4.8 |
| SENSING AMPLITUDE [DAILY MIN] [MV] | 3.4 | 3.2** |
| LEAD CHECK | OK | |
| PACING POLARITY | BIPOLAR | |
| SENSING POLARITY | BIPOLAR | |

FIG. 7B

STATUS REPORT
TO: PHYSICIAN GILANTHONY UNGAB
EVIA DR-T (SN 66154262)          LAST MESSAGE: JUL 25, 2012
PM IMPLANTED JUN 27, 2012        LAST CLINIC FOLLOW-UP: JUL 6, 2012
| AV SEQUENCES (EXCEPT DURING MODE SWITCHING) | | |
|---|---|---|
| INTRINSIC RHYTHM (AS - VS) [%] | 14 | 9 |
| VAT STIMULATION (AS - VP) [%] | 4 | 4 |
| CONDUCTED ATRIAL PACING (AP - VS) [%] | 62 | 52 |
| DUAL-CHAMBER PACING (AP - VP) [%] | 0 | 23 |
| VV SEQUENCE (VX - VX) [%] | 20 | 12 |
| PVARP | | |
| PVARP [MS] | 250 | 250 |
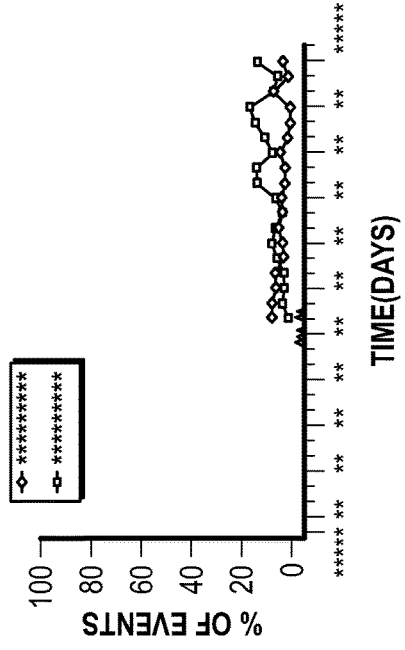
AV SEQUENCE (A SENSED)
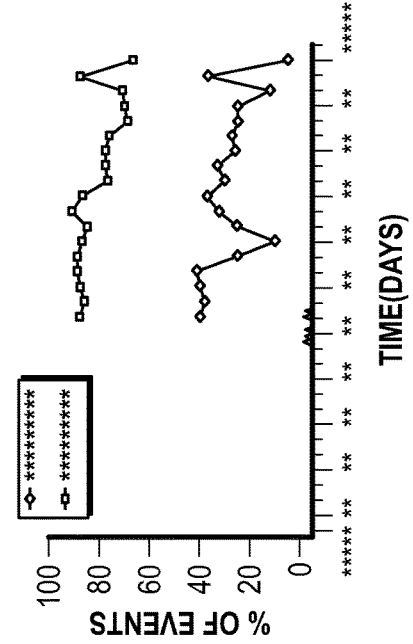
PACED RHYTHM
FIG. 7D

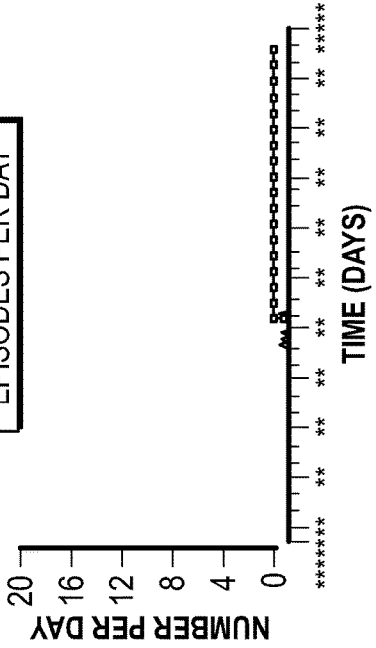
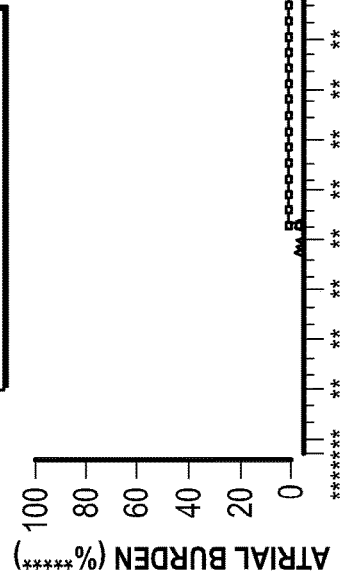
FIG. 7E

INTERROGATION INBOX

WELCOME, ADMIN
PATIENT SEARCH   INTERROGATION INBOX   REPORTING   READING SETTINGS   HELP

DISPLAY: [ALL INTERROGATIONS ▽]       FROM: [11-MAR-14]  TO: [21-MAR-14]

320

| STATUS▼ | READING PHYSICIAN▼ | ORDER▼ | PATIENT NAME▼ | LOCATION▼ | TIME REMAINING▼ | UPLOAD DATE, TIME▼ | VISIT #▼ | SOURCE▼ | SENT TO BILLING |
|---|---|---|---|---|---|---|---|---|---|
| PRELIMINARY | [UNGAB, GIL ▷] | 1 | △ ACKERMAN, KENDRA | SHARP CHULA VISTA ED | 2 HRS 40 MIN | 20-MAR-14, 22:10 | 352698412 | FOLLOWING | |
| PRELIMINARY | [UNGAB, GIL ▷] | 2 | WANG, XIXE | SHARP CHULA VISTA PACU | -1 HRS 20 MIN | 20-MAR-14, 10:50 | 995622347 | ADMIN | |
| PRELIMINARY | [SELECT... ▷] | — | JAMES, EDWARD | SHARP CHULA VISTA CANCER CTR | — | 21-MAR-14, 08:00 | 454778912 | — | |
| PRELIMINARY | [WAHDWA, MANISH ▷] | 2 | BENITEZ, JUANA | SHARP CHULA VISTA CANCER CTR | 7 HRS 0 MIN | 20-MAR-14, 22:10 | 985367454 | READING PANEL | |
| IN PROCESS | [WAHDWA, MANISH ▷] | 1 | GARCIA, TOMAS | SHARP CHULA VISTA CANCER CTR | — | 19-MAR-14, 22:10 | 332547845 | FOLLOWING | |
| IN PROCESS | [UNGAB, GIL ▷] | 1 | ALLEN, MICHAELA | REMOTE MONITORING | — | 19-MAR-14, 17:20 | 214475888 | ORDERING | |
| SIGNED | [UNGAB, GIL ▷] | 3 | NEARHOOD, RACHEL | IN-CLINIC | — | 15-MAR-14, 05:05 | 652244141 | READING PANEL | ☐ |
| SIGNED | [UNGAB, GIL ▷] | 1 | JACKSON, EZRA | IN-CLINIC | — | 11-MAR-14, 14:30 | 332657774 | READING PANEL | ✓ |

FIG. 9

PATIENT SEARCH   INTERROGATION INBOX   REPORTING   READING SETTINGS   HELP

WELCOME, ADMIN

330

READING SETTINGS

| CURRENT READING PANEL PHYSICIAN: | UNGAB, GIL ▷ | | | | | |
|---|---|---|---|---|---|---|
| UPCOMING SCHEDULE: | WAHDWA, MANISH ▷ | FROM: 22-MAR-14  08:00 ▷ | TO: 29-MAR-14  22:00 ▷ | | | |
| | LANDON, JAMES ▷ | FROM: 29-MAR-14  22:00 ▷ | TO: 05-APR-14  08:00 ▷ | | | |
| | ADD TO SCHEDULE | FROM: 05-APR-14  08:00 ▷ | TO: 12-APR-14  22:00 ▷ | | | |
| READING PANEL ROSTER: | ANDERSON, JOHN  BAXTER, BILL  DODGE, JOYCE | GILLIS, KARL  KENNEDY, TRISHA  LARSON, MILES | LANDON, JAMES  MCNABB, ARNE  MORRISON, CALVIN | NEARHOOD, RACHEL  SAMUELS, ROGER  SANTIAGO, TOMAS | UNGAB, GIL  VANCE, PAT  WAHDWA, MANISH | |
| | EDIT ROSTER | | | | | |
| READING PRIVILEGES: | CARDIOLOGIST:  ☑ PACING DEVICES  ☐ DEFIBRILLATING DEVICES | ELECTROPHYSIOLOGIST:  ☑ PACING DEVICES  ☑ DEFIBRILLATING DEVICES | PHYSICIAN:  ☑ PACING DEVICES  ☑ DEFIBRILLATING DEVICES | | | |
| READING PRIORITY: | 1ST PRIORITY: ORDERING PHYSICIAN ▷ | INTERROGATION ALERT: ALL ▷ | TIME LIMIT: 24 HOURS ▷ | TIME LIMIT ALERT: 2 HOURS ▷ | | |
| | 2ND PRIORITY: FOLLOWING PHYSICIAN ▷ | INTERROGATION ALERT: FLAGGED ▷ | TIME LIMIT: 12 HOURS ▷ | TIME LIMIT ALERT: 2 HOURS ▷ | | |
| | 3RD PRIORITY: READING PANEL ▷ | INTERROGATION ALERT: NONE ▷ | TIME LIMIT: 12 HOURS ▷ | TIME LIMIT ALERT: 2 HOURS ▷ | | |
| | 4TH PRIORITY: SELECT... ▷ | INTERROGATION ALERT: SELECT... ▷ | TIME LIMIT: SELECT... ▷ | TIME LIMIT ALERT: N/A | | |

READING SETTINGS — 330

WELCOME, ADMIN
PATIENT SEARCH   INTERROGATION INBOX   REPORTING   READING SETTINGS   HELP

CURRENT READING PANEL PHYSICIAN: [UNGAB, GIL ▷]

UPCOMING SCHEDULE:
[WAHDWA, MANISH ▷]   FROM: [22-MAR-14] [08:00 ▷]   TO: [29-MAR-14] [22:00 ▷]
[LANDON, JAMES ▷]   FROM: [29-MAR-14] [22:00 ▷]   TO: [05-APR-14] [08:00 ▷]
[ADD TO SCHEDULE]   FROM: [05-APR-14] [08:00 ▷]   TO: [12-APR-14] [22:00 ▷]

READING PANEL ROSTER:
ANDERSON, JOHN      GILLIS, KARL         LANDON, JAMES       NEARHOOD, RACHEL    UNGAB, GIL
BAXTER, BILL        KENNEDY, TRISHA      MCNABB, ARNE        SAMUELS, ROGER      VANCE, PAT
DODGE, JOYCE        LARSON, MILES        MORRISON, CALVIN    SANTIAGO, TOMAS     WAHDWA, MANISH

READING PRIVILEGES:
ELECTROPHYSIOLOGIST: [...IAN ▷]   PHYSICIAN:
PACING DEVICES                    ☑ PACING DEVICES
DEFIBRILLATING DEVICES            ☑ DEFIBRILLATING DEVICES

EDIT ROSTER
☑ ANDERSON, JOHN
☐ ANDREAS, PETE
☐ BASS, LANDON
☑ BAXTER, BILL
☑ DODGE, JOYCE
☑ GILLIS, KARL
☑ KENNEDY, TRISHA
☑ LARSON, MILES
SELECT: ALL  NONE   [DONE]

[...CIAN ▷]   INTERROGATION ALERT: [ALL ▷]       TIME LIMIT: [24 HOURS ▷]   TIME LIMIT ALERT: [2 HOURS ▷]
              INTERROGATION ALERT: [FLAGGED ▷]   TIME LIMIT: [12 HOURS ▷]   TIME LIMIT ALERT: [2 HOURS ▷]
[▷]           INTERROGATION ALERT: [NONE ▷]      TIME LIMIT: [12 HOURS ▷]   TIME LIMIT ALERT: [2 HOURS ▷]

READING PRIORITY:
4TH PRIORITY: [SELECT... ▷]   INTERROGATION ALERT: [SELECT... ▷]   TIME LIMIT: [SELECT... ▷]   TIME LIMIT ALERT: N/A

INTERROGATION INBOX

PATIENT SEARCH    INTERROGATION INBOX    REPORTING    READING SETTINGS    HELP

WELCOME, DR. UNGAB

DISPLAY: [ALL INTERROGATIONS ▽]    FROM: [11-MAR-14]    TO: [21-MAR-14]

| STATUS ▸ | PATIENT NAME ▸ | LOCATION ▸ | TIME REMAINING ▸ | UPLOAD DATE, TIME ▸ | VISIT # ▸ | SOURCE ▸ | REPORTS |
|---|---|---|---|---|---|---|---|
| PRELIMINARY | △ ACKERMAN, KENDRA | SHARP CHULA VISTA ED | 2 HRS 40 MIN | 20-MAR-14, 22:10 | 352698412 | FOLLOWING | [CREATE DICTATION] |
| PRELIMINARY | WANG XIXE | SHARP CHULA VISTA PACU | -1 HRS 20 MIN | 20-MAR-14, 10:50 | 995622347 | ADMIN | [CREATE DICTATION] |
| IN PROCESS | ALLEN MICHAELA | SHARP CHULA VISTA CANCER CTR | 1 HR 5 MIN | 21-MAR-14, 08:00 | 454778912 | ORDERING | [CREATE DICTATION] |
| SIGNED | NEARHOOD, RACHEL | REMOTE MONITORING | — | 15-MAR-14, 05:05 | 985367454 | READING PANEL | [GENEVA REPORT (PDF)] |
| SIGNED | JACKSON, EZRA | IN-CLINIC | — | 11-MAR-14, 14:30 | 332547845 | READING PANEL | [GENEVA REPORT (PDF)] |

FIG. 16

LEAD STATUS

⚠️ ATTENTION
GENEVA WAS UNABLE TO AUTOMATICALLY ACCESS ONE OR MORE DATA POINTS. SEE MANUFACTURER DATA WITHIN THE GENEVA REPORT (PDF) FOR COMPLETE DETAILS.

|  | LEAD A | LEAD RV | LEAD LV |
|---|---|---|---|
| SENSE: | 4.6 MV | 1.6 MV | NOT APPLICABLE |
| IMPEDANCE: | 532 OHM | 503 OHM | NOT APPLICABLE |
| PACING THRESHOLD AMPLITUDE: | ⚠ SEE MFR DATA | 0.8 V | NOT APPLICABLE |
| THRESHOLD MEASUREMENT METHOD: | ⚠ SEE MFR DATA | DEVICE AUTOMATIC | NOT APPLICABLE |

LEAD SETTINGS

| CHAMBER: | LEAD RA | LEAD RV | LEAD LV |
|---|---|---|---|
| SENSITIVITY: | .04 MV | 1.3 MV (ADAPTIVE) | NOT APPLICABLE |
| SENSING POLARITY: | BIPOLAR | UNIPOLAR | NOT APPLICABLE |
| SENSING VECTOR: | RA TIP RA RING | RA TIP-CAN | NOT APPLICABLE |
| PACING OUTPUT: | 2.0 V | 2.0 V (ADAPTIVE) | NOT APPLICABLE |
| PACING PULSE WIDTH: | .04 MS | 0.5 MS | NOT APPLICABLE |
| PACING VECTOR*: | RA TIP RA RING | RV TIP-RV RING | NOT APPLICABLE |
| SHOCK IMPEDANCE MEASUREMENT: | ⚠ SEE MFR DATA | | |
| SHOCK-VECTOR | ⚠ SEE MFR DATA | | |

*(-) CATHODE - (+) ANODE

LEAD GENERAL INFORMATION

| LEAD MANUFACTURER: | ⚠ SEE MFR DATA |
|---|---|
| LEAD MODEL: | ⚠ SEE MFR DATA |
| LEAD SERIAL NUMBER: | ⚠ SEE MFR DATA |
| LEAD IMPLANT DATE: | ⚠ SEE MFR DATA |

PATIENT NAME: ACKERMAN, KENDRA
D.O.B.: 02-FEB-1948
MRN #: 101-593-814
VISIT #: 61527632
LOCATION: SHARP CHULA VISTA ED

INTERROGATED: 20-MAR-14, 22:05
UPLOADED: 20-MAR-14, 22:10
REASON FOR INTERROGATION:
SHORTNESS OF BREATH, DIZZINESS

STATUS: IN PROCESS
CURRENT REVIEWER:
UNGAB,GILL

DEVICE INTERROGATION DICTATION   EXPAND ALL   COLLAPSE ALL   [MANUFACTURER DATA (PDF)]

[INTERPRETATION/FINDINGS*] > [CONCLUSION*] > [BILLING*]   [SAVE]
SECTIONS MARKED WITH AN ASTERISK (*) ARE REQUIRED/INCOMPLETE.

INTERPRETATION/FINDINGS

| DEVICE DETAILS | BIOTRONIK AICD |
| BATTERY STATUS | NORMAL BATTERY FUNCTION |
| LEAD STATUS | REQUIRED/INCOMPLETE* |
| EPISODE COUNT | REQUIRED/INCOMPLETE* |
| VT THERAPIES | VT THERAPIES ARE PROGRAMMED ON |
| MAGNET MODE | MAGNET MODE IS TURNED ON FOR INTRAOPERATIVE OF DEFIBRILLATOR PLACING THE MAGNET OVER THE DEVICE WILL INHIBIT TACHY |
| MRI SAFETY | DEVICE IS NOT MRI CONDITIONAL |

CONCLUSION

[CONCLUSION]   REQUIRED/INCOMPLETE*

BILLING (NOT INCLUDED IN FINAL REPORT)

[ADD CPT CODE(S)]   REQUIRED/INCOMPLETE*

[ADD DIAGNOSIS CODE(S)]   REQUIRED/INCOMPLETE*

[REVIEW]

FIG. 19

PATIENT NAME: ACKERMAN, KENDRA   INTERROGATED: 20-MAR-14, 22:05   STATUS: IN PROCESS
D.O.B.: 02-FEB-1948   UPLOADED: 20-MAR-14, 22:10   CURRENT REVIEWER: UNGAB,GILL
MRN #: 101-593-814   REASON FOR INTERROGATION:
VISIT #: 61527632   SHORTNESS OF BREATH, DIZZINESS
LOCATION: SHARP CHULA VISTA ED

DEVICE INTERROGATION DICTATION   EXPAND ALL   COLLAPSE ALL   [MANUFACTURER DATA (PDF)]

[ INTERPRETATION/FINDINGS > CONCLUSION > BILLING* > ]   [ SAVE ]
SECTIONS MARKED WITH AN ASTERISK (*) ARE REQUIRED/INCOMPLETE.

INTERPRETATION/FINDINGS

DEVICE DETAILS

| | |
|---|---|
| DEVICE TYPE: | AICD |
| IMPLANT DATE: | 01/01/12 |
| FOLLOWING PHYSICIAN: | DR. UNGAB |
| FOLLOWING PHYSICIAN CONTACT: | XXX-XXX-XXXX |
| PATIENT DATE OF BIRTH: | 04/30/1967 |
| DEVICE MANUFACTURER: | BIOTRONIK |
| DEVICE MODEL: | XXXXX |
| DEVICE SERIAL NUMBER: | XXXX-XXXXX |
| DEVICE IMPLANTER: | DR. UNGAB |
| DEVICE IMPLANTER CONTACT: | XXX-XXX-XXXX |
| ADVISORY: | N/A |

| INTERPRETATION | CONCLUSION | |
|---|---|---|
| | | MEDTRONIC |
| ✓ | | BIOTRONIK |
| | | BOSTON SCIENTIFIC |
| | | ST. JUDE |
| | | PACEMAKER |
| ✓ | | AICD |
| | | CRTD |
| | | CRTP |
| | | ILR |
| | | FREE TEXT... |

FIG. 20A

| BATTERY STATUS | | |
|---|---|---|
| BATTERY STATUS: | MOL (MIDDLE OF LIFE) | |
| REMAINING LONGEVITY: | 26 MONTHS | |
| MEASURED VOLTAGE: | XXV | |
| MINIMUM VOLTAGE: | 3.4 / 4.5 V | |
| CHARGE TIME: | 9.7 SEC | |

| INTERROGATION | CONCLUSION |
|---|---|
| ✓ | NORMAL BATTERY FUNCTION |
| | DEVICE IS NEARING REPLACEMENT INTERVAL |
| | DEVICE HAS REACHED REPLACEMENT INTERVAL |
| | DEVICE HAS REACHED END OF LIFE |
| | ABNORMAL CHARGE TIME |
| | NORMAL CHARGE TIME |
| | BATTERY STATUS: |
| | FREE TEXT... |

| LEAD STATUS | LEAD A | LEAD RV | LEAD LV |
|---|---|---|---|
| SENSE: | 4.6 MV | 1.6MV | NOT APPLICABLE |
| IMPEDANCE: | 532 OHM | 503 OHMS | NOT APPLICABLE |
| PACING THRESHOLD AMPLITUDE: | ⚠ SEE MFR DATA | 0.8 V | NOT APPLICABLE |
| THRESHOLD MEASUREMENT METHOD: | ⚠ SEE MFR DATA | DEVICE AUTOMATIC | NOT APPLICABLE |

LEAD SETTINGS

| CHAMBER: | LEAD RA | LEAD RV | LEAD LV |
|---|---|---|---|
| SENSITIVITY: | .04 TV | 1.3 MV (ADAPTIVE) | NOT APPLICABLE |
| SENSING POLARITY: | BIPOLAR | UNIPOLAR | NOT APPLICABLE |
| SENSING VECTOR: | RA TIP RA RING | RVTIP - CAN | NOT APPLICABLE |
| PACING OUTPUT: | 2.0V | 2.0 V (ADAPTIVE) | NOT APPLICABLE |
| PACING PULSE WIDTH: | .40 TS | 0.5 MS | NOT APPLICABLE |
| PACING VECTOR*: | RA TIP RA RING | RVTIP - RVRING | NOT APPLICABLE |
| SHOCK IMPEDANCE MEASUREMENT: | ⚠ SEE MFR DATA | | |
| SHOCK - VECTOR: | ⚠ SEE MFR DATA | | |

* (-) CATHODE - (+) ANODE

LEAD GENERAL INFORMATION

| LEAD MANUFACTURER: | ⚠ SEE MFR DATA |
|---|---|
| LEAD MODEL: | ⚠ SEE MFR DATA |
| LEAD SERIAL NUMBER: | ⚠ SEE MFR DATA |
| LEAD IMPLANT DATE: | ⚠ SEE MFR DATA |

| INTERPRETATION | CONCLUSION | THRESHOLD |
| --- | --- | --- |
| | | ELEVATION OF RV THRESHOLD. THIS PARAMETER SHOULD BE MONITORED WITH MORE FREQUENT EVALUATION. |
| | | PACING THRESHOLD IS GREATER THAN THE PROGRAMMED OUTPUTS FOR THIS LEAD |
| | | POSSIBLE LEAD MALFUNCTION DETECTED |
| | | LEAD DATA AVAILABLE IS WITHIN NORMAL LIMITS, HOWEVER FURTHER TESTING MAY BE NEEDED OF CLINICALLY INDICATED |
| | | LEAD DATA IS WITHIN NORMAL LIMITS |
| | | THIS LEAD DOES NOT HAVE A 2:1 SAFETY MARGIN |
| | ✓ | AUTOCAPTURE FUNCTIONALITY NOT PROGRAMMED. IF CLINICALLY INDICATED, WOULD RECOMMEND MANUAL LEAD TESTED |
| | | PACING THRESHOLDS ARE WITHIN NORMAL LIMITS |
| | | FREE TEXT... |

| INTERPRETATION | CONCLUSION | IMPEDANCE |
| --- | --- | --- |
| | | IMPEDANCES ARE WITHIN THE NORMAL RANGE |
| | ✓ | IMPEDANCES ARE NOT WITHIN NORMAL RANGE |
| | | FREE TEXT... |

| INTERPRETATION | CONCLUSION | SENSING |
| --- | --- | --- |
| | | RIGHT ATRIAL WAVE SENSING WITHIN NORMAL LIMITS |
| | | RIGHT VENTRICULAR LEAD SENSING WITHIN NORMAL LIMITS |
| | | LEFT VENTRICULAR LEAD SENSING WITHIN NORMAL LIMITS |
| | | SMALL P WAVE AMPLITUDE NOTED. POSS BY RESULTING IN ATRIAL UNDER SENSING |
| | | SMALL R WAVE AMPLITUDE NOTED. POSS BY RESULTING IN A WAVE UNDER SENSING |
| | ✓ | SEARCHING VALUES ARE WITHIN NORMAL RANGE |

| (#) EPISODE COUNT | | | 430 |
|---|---|---|---|
| THERAPY COUNTS: | 5 | | |
| TYPE | RECENT* | TOTAL** | |
| SHOCKS DELIVERED | 3 | 3 | |
| SHOCKS ABORTED | 0 | 0 | |
| ANTI-TACHY PACINGS | 2 | 2 | |
| RECENT EPISODES: | 1 | | |
| SINCE: | 01/01/2012 | | |
| TYPE | RECENT* | TOTAL** | |
| ATRIAL FIBRILLATION | 1 | 1 | |
| SVT | 0 | 0 | |
| VF | 0 | 0 | |
| VT1 | 0 | 0 | |
| VT2 | 0 | 0 | |

* SINCE COUNTERS LAST CLEARED: 01/01/2012, 10:30AM
** SINCE IMPLANTATION: 01/01/2010

| INTERPRETATION | CONCLUSION |
|---|---|
| ✓ | POSSIBLE DEVICE DETECTED AFIB RECORDED |
|   | PACEMAKER TACHYCARDIA PMT DETECTED |
| ✓ | EVIDENCE OF FREQUENT NON-SUSTAINED VENTRICULAR ARRHYTHMIAS NOTED. FREQUENCY AND DURATION OF THESE EVENTS SHOULD BE FOLLOWED EVER TIME |
|   | EVENT(S) NOTED: 2 ▸ ▸ SVT ▸ NO TREATMENT ▸ DELIVERED ▸ |
|   | EVENT(S) NOTED: SELECT P... ▸ SELECT EPISODE TYPE... ▸ SELECT THERAPY... ▸ SELECT OUTCOME... ▸ |
|   | FREE TEXT... |

VT THERAPIES

VT THERAPIES: TURNED ON

| TYPE | RATE BPM | DETECTION BEATS | ANTI-TACHY PACING | SHOCKS | DETAILS |
|---|---|---|---|---|---|
| VF | 195 | 12/18 | - | 30JX5 | STABILITY |
| FASTVT | 165 | 8 | RAMPX6 | 20JX1, 30JX5 | |
| VTMON | 145 | 12 | - | - | FFRW FILTER |
| AT | 190 | | | | XYZ XYZ XYZ XYZ |
| P-IEGM | - | - | - | - | |

| INTERPRETATION | CONCLUSION | |
|---|---|---|
| ✓ | | VT THERAPIES ARE PROGRAMMED ON |
| | | VT THERAPIES ARE PROGRAMMED OFF |
| | | FREE TEXT... |

MAGNET MODE

| MAGNET MODE: | ON |
|---|---|
| PACING: | NO EFFECT |
| TACHY: | DISABLED |

THIS PATIENT HAS AN ICD. PLACING A MAGNET OVER THE DEVICE WILL INHIBIT ALL TACHYARRHYTHMIA THERAPIES BUT WILL HAVE NO EFFECT ON THE PACEMAKER FUNCTIONALITY OF THE DEVICE.

PLEASE LIMIT ELECTRACAUTERY TO SHORT BURSTS (MAXIMUM 2 SECONDS) SINCE PACING OUTPUT WILL CONTINUE TO BE INHIBITED DURING ELECTROCAUTERY. IN PACEMAKER DEPENDENT PATIENTS, ELECTRICAL NOISE FROM ELECTROCAUTERY MAY INHIBIT PACING SIGNIFICANTLY AND LEAD TO A CLINICALLY RELEVANT DECREASE IN CARDIAC OUTPUT.

| INTERPRETATION | CONCLUSION | |
|---|---|---|
| | | MAGNET MODE IS TURNED ON FOR PACEMAKER. PLACING MAGNET OVER THE DEVICE WILL RESULT IN FORCED PACING. |
| | | MAGNET MODE IS TURNED OFF FOR PACEMAKER. REPROGRAMMING OF DEVICE REQUIRED FOR INTRAOPERATIVE MANAGEMENT. |
| ✓ | | MAGNET MODE IS TURNED ON FOR DEFIBRILLATOR. PLACING THE MAGNET OVER THE DEVICE WILL INHIBIT TACHYARRHYTHMIA THERAPIES. THERE IS NO EFFECT ON PACING. |
| | | MAGNET MODE IS TURNED OFF FOR DEFIBRILLATOR. PLACING A MAGNET OVER THE DEVICE WILL HAVE NO EFFECT ON PREVENTION OF SHOCKS AND NO EFFECT ON PACING. |
| | | FREE TEXT... |

FIG. 20E

Conclusion

430

| CONCLUSION | |
|---|---|
| ✓ | Normal device function based on available data. No suggestion of volume overload based on optivol fluid threshold. |
| | Probably acute on chronic sostolic congestive heart failure as per transtherasic impedance trending. |
| | Anticoagulation can be considered if clinically indicated. |
| | Evidence of appropriately treated VT episode. |
| | Increased impedance suggests lead fracture. Recommend further clinical evaluation. |
| | Ventricular arrhythmia detected outside of the current programmed zones. Consider reprogramming zones. |
| | Autocapture not programmed. If clinically indicated would recommend manual threshold testing. |
| | free text... |

Billing (Not included in Final Report)

Add CPT Code(s)    required/incomplete*

Add Diagnosis Code(s)    required/incomplete*

Reset    Review

FIG. 20G

Free Text Dictation: Color Coding

You have entered a free text dictation in a section where Geneva detected missing data. How should Geneva interpret your entry in terms of color coding?

☑ Green: Data available is consistent with normal function — 452

☐ Yellow: Data is incomplete or not conclusive of normal function — 454

☐ Red: Critical abnormal data identified — 456

Done

PATIENT NAME: ACKERMAN, KENDRA
D.O.B.: 02-FEB-1948
MRN #: 101-593-814
VISIT #: 61527632
LOCATION: SHARP CHULA VISTA ED

INTERROGATED: 20-MAR-14, 22:05
UPLOADED: 20-MAR-14, 22:10
REASON FOR INTERROGATION:
SHORTNESS OF BREATH, DIZZINESS

STATUS: IN PROCESS
CURRENT REVIEWER:
UNGAB,GILL

DEVICE INTERROGATION DICTATION

EXPAND ALL  COLLAPSE ALL  [MANUFACTURER DATA (PDF)]

[INTERPRETATION/FINDINGS > CONCLUSION > BILLING >]

[SAVE]

SECTIONS MARKED WITH AN ASTERISK (*) ARE REQUIRED/INCOMPLETE.

INTERPRETATION/FINDINGS

DEVICE DETAILS — BIOTRONIK AICD

BATTERY STATUS — NORMAL BATTERY FUNCTION

LEAD STATUS —
THRESHOLD:
MANUFACTURER'S DATA REVIEWED AS WITHIN NORMAL RANGE <--SELECTED DICATION WILL CONVERT COLOR CODE TO GREEN UPON FINAL REVIEW/E-SIGN.
IMPEDANCE:
IMPEDANCE VALUES WITHIN NORMAL RANGE <--SELECTED DICATION WILL CONVERT COLOR CODE TO GREEN UPON FINAL REVIEW/E-SIGN.
SENSING:
SENSING VALUES WITHIN NORMAL RANGE <--FREE TEXT DICATION WILL CONVERT COLOR CODE TO GREEN UPON FINAL REVIEW/E-SIGN.

EPISODE COUNT —
MULTIPLE A-FIB EVENTS OF UNKNOWN DURATION
MULTIPLE NON-SUSTAINED NSVT EVENTS
1 ABORTED SHOCK
1 TREATED VFIB EVENT

VT THERAPIES — VT THERAPIES ARE PROGRAMMED ON

MAGNET — MAGNET MODE IS TURNED ON FOR INTRAOPERATIVE OF DEFIBRILLATOR
...IBIT TACHY

[ADD CPT CODE(S)]
IN PERSON
☑ 93288 - PACEMAKER (NO PROGRAMMING EVALUATION)
☐ 93279 - PACEMAKER (SINGLE LEAD)
☐ 93280 - PACEMAKER (DUAL CHAMBER)
☐ 93281 - PACEMAKER (CRT-P)
☑ 93289 - AICD (NO PROGRAMMING EVALUATION)
☐ 93282 - AICD (SINGLE LEAD)
☐ 93283 - AICD (DUAL CHAMBER)
☐ 93284 - AICD (CRT-D)
REMOTE MONITORING
☐ 93296 - PACEMAKER/AICD TECHNICAL FEE (90 DAYS)

SELECT: ALL  NONE          [DONE]

...PTIVOL FLUID THRESHOLD.

430A

[ADD DIAGNOSIS CODE(S)] REQUIRED/INCOMPLETE*

[RESET]  [REVIEW]

PATIENT NAME: ACKERMAN, KENDRA
D.O.B.: 02-FEB-1948
MRN #: 101-593-814
VISIT #: 61527632
LOCATION: SHARP CHULA VISTA ED

INTERROGATED: 20-MAR-14, 22:05
UPLOADED: 20-MAR-14, 22:10
REASON FOR INTERROGATION:
SHORTNESS OF BREATH, DIZZINESS

STATUS: IN PROCESS
CURRENT REVIEWER: UNGAB, GILL

EXPAND ALL  COLLAPSE ALL  [ MANUFACTURER DATA (PDF) ]

DEVICE INTERROGATION DICTATION

[ INTERPRETATION/FINDINGS > CONCLUSION > BILLING* > ]

[ SAVE ]

SECTIONS MARKED WITH AN ASTERISK (*) ARE REQUIRED/INCOMPLETE.

INTERPRETATION/FINDINGS

DEVICE DETAILS — BIOTRONIK AICD

BATTERY STATUS — NORMAL BATTERY FUNCTION

LEAD STATUS —
THRESHOLD:
MANUFACTURER'S DATA REVIEWED AS WITHIN NORMAL RANGE <--SELECTED DICATION WILL CONVERT COLOR CODE TO GREEN UPON FINAL REVIEW/E-SIGN.
IMPEDANCE:
IMPEDANCE VALUES WITHIN NORMAL RANGE <--SELECTED DICATION WILL CONVERT COLOR CODE TO GREEN UPON FINAL REVIEW/E-SIGN.
SENSING:
SENSING VALUES WITHIN NORMAL RANGE <--FREE TEXT DICATION WILL CONVERT COLOR CODE TO GREEN UPON FINAL REVIEW/E-SIGN.

EPISODE COUNT —
MULTIPLE A-FIB EVENTS OF UNKNOWN DURATION
MULTIPLE NON-SUSTAINED NSVT EVENTS
1 ABORTED SHOCK
1 TREATED VFIB EVENT

VT THERAPIES — VT THERAPIES ARE PROGRAMMED ON

MAGNET MODE —
MAGNET MODE IS TURNED ON FOR INTRAOPERATIVE OF DEFIBRILLATOR
PLACING THE MAGNET OVER THE DEVICE WILL INHIBIT TACHY

MRI SAFETY — DEVICE IS NOT MRI CONDITIONAL

CONCLUSION

CONCLUSION — NORMAL DEVICE FUNCTION BASED ON AVAILABLE DATA.
...BASED ON OPTIVOL FLUID THRESHOLD.

ADD DIAGNOSIS CODE(S) — 430B
- [ ] V45.01 - PACEMAKER INSITU
- [ ] V45.02 - AICD INSITU
- [ ] 780.1 - PRE SYNCOPE
- [ ] 780.2 - SYNCOPE
- [✓] 786.05 - SHORTNESS OF BREATH
- [✓] 780.4 - DIZZINESS
- [✓] 785.1 - PALPITATIONS
- [ ] 414.8 - INSCHEMIC CARDIOMYOPOTHY (EVALUATION)
(TION)

SELECT: ALL  NONE       [ DONE ]

[ RESET ] [ REVIEW ]

| FINAL DICTATION PREVIEW | |
|---|---|
| CONCLUSION | |
| CONCLUSION | NORMAL DEVICE FUNCTION BASED ON AVAILABLE DATA.<br>NO SUGGESTIONS OF VOLUME OVERLOAD BASED ON OPTIVOL FLUID THRESHOLD. |
| INTERPRETATION/FINDINGS | |
| DEVICE DETAILS | BIOTRONIK<br>AICD |
| BATTERY STATUS | NORMAL BATTERY FUNCTION |
| LEAD STATUS | THRESHOLD:<br>MANUFACTURER'S DATA REVIEWED AS WITHIN NORMAL RANGE<br><br>IMPEDANCE:<br>IMPEDANCE VALUES WITHIN NORMAL RANGE<br><br>SENSING:<br>SENSING VALUES WITHIN NORMAL RANGE |
| EPISODE COUNT | MULTIPLE A-FIB EVENTS OF UNKNOWN DURATION<br>MULTIPLE NON-SUSTAINED NSVT EVENTS<br>1 ABORTED SHOCK<br>1 TREATED VFIB EVENT |
| VT THERAPIES | VT THERAPIES ARE PROGRAMMED ON |
| MAGNET MODE | MAGNET MODE IS TURNED ON FOR INTRAOPERATIVE OF DEFIBRILLATOR<br>PLACING THE MAGNET OVER THE DEVICE WILL INHIBIT TACHY |
| MRI SAFETY | DEVICE IS NOT MRI CONDITIONAL |

E-SIGN ⟋432

LOREM IPSUM DOLOR SIT AMET, CONSECTETUR ADIPISICING ELIT, SED DO EIUSMOD TEMPOR INCIDIDUNT UT LABORE ET DOLORE MAGNA ALIQUA. UT ENIM AD MINIM VENIAM, QUIS NOSTRUD EXERCITATION ULLAMCO LABORIS NISI UT ALIQUIP EX EA COMMODO CONSEQUAT. LOREM IPSUM DOLOR SIT AMET, CONSECTETUR ADIPISICING ELIT, SED DO EIUSMOD TEMPOR INCIDIDUNT UT LABORE ET DOLORE MAGNA ALIQUA. UT ENIM AD MINIM VENIAM, QUIS NOSTRUD EXERCITATION ULLAMCO LABORIS NISI UT ALIQUIP EX EA COMMODO CONSEQUAT.

I HAVE READ AND AGREE TO THE TERMS AND CONDITIONS STATED ABOVE. ☐

[RETURN TO EDITING]

FIG. 26

FINAL DICTATION PREVIEW

CONCLUSION

| CONCLUSION | NORMAL DEVICE FUNCTION BASED ON AVAILABLE DATA.<br>NO SUGGESTIONS OF VOLUME OVERLOAD BASED ON OPTIVOL FLUID THRESHOLD. |
|---|---|

INTERPRETATION/FINDINGS

| | | |
|---|---|---|
|  | DEVICE DETAILS | BIOTRONIK<br>AICD |
|  | BATTERY STATUS | NORMAL BATTERY FUNCTION |
|  | LEAD STATUS | THRESHOLD:<br>MANUFACTURER'S DATA REVIEWED AS WITHIN NORMAL RANGE<br><br>IMPEDANCE:<br>IMPEDANCE VALUES WITHIN NORMAL RANGE<br><br>SENSING:<br>SENSING VALUES WITHIN NORMAL RANGE |
|  | EPISODE COUNT | MULTIPLE A-FIB EVENTS OF UNKNOWN DURATION<br>MULTIPLE NON-SUSTAINED NSVT EVENTS<br>1 ABORTED SHOCK<br>1 TREATED VFIB EVENT |
|  | VT THERAPIES | VT THERAPIES ARE PROGRAMMED ON |
|  | MAGNET MODE | MAGNET MODE IS TURNED ON FOR INTRAOPERATIVE OF DEFIBRILLATOR<br>PLACING THE MAGNET OVER THE DEVICE WILL INHIBIT TACHY |
|  | MRI SAFETY | DEVICE IS NOT MRI CONDITIONAL |

E-SIGN —432

LOREM IPSUM DOLOR SIT AMET, CONSECTETUR ADIPISICING ELIT, SED DO EIUSMOD TEMPOR INCIDIDUNT UT LABORE ET DOLORE MAGNA ALIQUA. UT ENIM AD MINIM VENIAM, QUIS NOSTRUD EXERCITATION ULLAMCO LABORIS NISI UT ALIQUIP EX EA COMMODO CONSEQUAT. LOREM IPSUM DOLOR SIT AMET, CONSECTETUR ADIPISICING ELIT, SED DO EIUSMOD TEMPOR INCIDIDUNT UT LABORE ET DOLORE MAGNA ALIQUA. UT ENIM AD MINIM VENIAM, QUIS NOSTRUD EXERCITATION ULLAMCO LABORIS NISI UT ALIQUIP EX EA COMMODO CONSEQUAT.

I HAVE READ AND AGREE TO THE TERMS AND CONDITIONS STATED ABOVE. ☑     [ E-SIGN ]

[ RETURN TO EDITING ]

PATIENT NAME: ACKERMAN, KENDRA  INTERROGATED: 20-MAR-14, 22:05
D.O.B.: 02-FEB-1948                UPLOADED: 20-MAR-14, 22:10
MRN #: 101-593-814
VISIT #: 61527632
LOCATION: SHARP CHULA VISTA ED

STATUS: SIGNED
ELECTRONICALLY SIGNED BY: UNGAB,GIL
DATE/TIME: 21-MAR-14, 08:15

FINAL REPORT - DEVICE INTERROGATION

1. CONCLUSION AND INTERPRETATION/FINDINGS..................................................................PAGE 1
2. GENEVA REPORT................................................................................................................PAGE 2
3. MANUFACTURER'S DATA...................................................................................................PAGE 5

- CONCLUSION -

| CONCLUSION | NORMAL DEVICE FUNCTION BASED ON AVAILABLE DATA.<br>NO SUGGESTION OF VOLUME OVERLOAD BASED ON OPTIVOL FLUID THRESHOLD. |
|---|---|

- INTERPRETATION/FINDINGS -

| DEVICE DETAILS | BIOTRONIK<br>AICD |
|---|---|
| BATTERY STATUS | NORMAL BATTERY FUNCTION |
| LEAD STATUS | THRESHOLD:<br>NO THRESHOLD DATA AVAILABLE<br><br>IMPEDANCE:<br>IMPEDANCE VALUES WITHIN NORMAL RANGE<br><br>SENSING:<br>SENSING VALUES WITHIN NORMAL RANGE |
| EPISODE COUNT | MULTIPLE A-FIB EVENTS OF UNKNOWN DURATION<br>MULTIPLE NON-SUSTAINED NSVT EVENTS<br>1 ABORTED SHOCK<br>1 TREATED VFIB EVENT |
| VT THERAPIES | VT THERAPIES ARE PROGRAMMED ON |
| MAGNET MODE | DEVICE IS NOT MRI CONDITIONAL |
| MRI SAFETY | DEVICE IS NOT MRI CONDITIONAL |

- END CONCLUSION AND INTERPRETATION/FINDINGS -

PATIENT NAME: ACKERMAN, KENDRA
D.O.B.: 02-FEB-1948
MRN #: 101-593-814
VISIT #: 61527632
LOCATION: SHARP CHULA VISTA ED

INTERROGATED: 20-MAR-14, 22:05
UPLOADED: 20-MAR-14, 22:10
REASON FOR INTERROGATION:
SHORTNESS OF BREATH, DIZZINESS

STATUS: SIGNED
ELECTRONICALLY SIGNED BY:
UNGAB, GIL
DATE/TIME: 21-MAR-14, 08:15

- GENEVA REPORT -

KENDRA ACKERMAN
UPLOADED: 20-MAR-14, 22:10 (ED)

272

| DEVICE DETAILS | BATTERY STATUS | LEAD STATUS | ARRYTHMIA LOG | VT THERAPIES | MAGNET MODE | MRI SAFETY | CHF WATCH |
|---|---|---|---|---|---|---|---|
| ICD 01/01/12 DR. UNGAB XXX-XXX-XXXX | MOL 26 MONTHS | OK | AFIB: DETECTED CHADS$_2$: 3 HAS-BLED: 3 | TURNED ON | ON PACING: NO EFFECT TACHY: DISABLED | NOT SAFE FOR MRI! | NOT APPLICABLE |

274

HEART HISTORY
IMPLANTED: 01/01/12
PACING PARAMETERS: DODR 60/120
LAST UPDATED: 20-MAR-14, 22:10
ED INTERROGATION

V FIB 200
VT 2 175
VT 1 150

HR | JAN 2013 | FEB 2013 | MAR 2013 | APR 2013 | MAY 2013 | JUN 2013 | JUL 2013 | AUG 2013 | SEP 2013 | OCT 2013 | NOV 2013 | DEC 2013

ATP  ATP  DEFIB

* GRAPH DISPLAYS LAST 4 EPISODES ONLY

276

DEVICE DETAILS

| DEVICE TYPE: | ICD |
|---|---|
| IMPLANT DATE: | 01/01/12 |
| FOLLOWING PHYSICIAN: | DR. UNGAB |
| FOLLOWING PHYSICIAN CONTACT: | XXX-XXX-XXXX |
| PATIENT DATE OF BIRTH: | 04/30/1967 |
| DEVICE MODEL: | XXXXX |
| DEVICE SERIAL NUMBER: | XXXX-XXXXX |
| DEVICE IMPLANTER: | DR. UNGAB |
| DEVICE IMPLANTER CONTACT: | XXX-XXX-XXXX |
| ADVISORY: | N/A |

276

BATTERY STATUS

| BATTERY STATUS: | MOL (MIDDLE OF LIFE) |
|---|---|
| REMAINING LONGEVITY: | 26 MONTHS |
| MEASURED VOLTAGE: | XX V |
| MINIMUM VOLTAGE: | 3.4 < 4.5 V |
| CHARGE TIME: | 9.7 SEC |

| | | | STATUS: SIGNED |
|---|---|---|---|
| PATIENT NAME: ACKERMAN, KENDRA | INTERROGATED: 20-MAR-14, 22:05 | | ELECTRONICALLY SIGNED BY: |
| D.O.B.: 02-FEB-1948 | UPLOADED: 20-MAR-14, 22:10 | | UNGAB, GIL |
| MRN #: 101-593-814 | REASON FOR INTERROGATION: | | DATE/TIME: 21-MAR-14, 08:15 |
| VISIT #: 61527632 | SHORTNESS OF BREATH, DIZZINESS | | |
| LOCATION: SHARP CHULA VISTA ED | | | |

LEAD STATUS

| | LEAD A | LEAD RV | LEAD LV |
|---|---|---|---|
| SENSE: | -- | 1.6 MV | 1.6MV |
| IMPEDANCE: | -- | 503 OHMS | 503 OHMS |
| PACING THRESHOLD AMPLITUDE: | -- | 0.8 V | 0.8 V |
| THRESHOLD MEASUREMENT METHOD: | -- | PROGRAMMER MANUAL | PROGRAMMER MANUAL |
| LEAD SETTINGS | | | |
| CHAMBER: | LEAD RA | LEAD RV | LEAD LV |
| SENSITIVITY: | -- | 1.3 MV (ADAPTIVE) | 1 MV (FIXED) |
| SENSING POLARITY: | -- | UNIPOLAR | UNIPOLAR |
| SENSING VECTOR: | -- | RVTIP - CAN | LVTIP - CAN |
| PACING OUTPUT: | -- | 2.0 V (ADAPTIVE) | 2.0 V (FIXED) |
| PACING PULSE WIDTH: | -- | 0.5 MS | 0.5 MS |
| PACING VECTOR*: | -- | BIPOLAR | UNIPOLAR |
| | -- | RVTIP - RVRING | LVTIP - RVRING |

SHOCK-VECTOR: RVCOIL, RACOIL - CAN
* (-) CATHODE - (+) ANODE
LEAD GENERAL INFORMATION

| LEAD MANUFACTURER: | [COMPANY NAME] |
|---|---|
| LEAD MODEL: | XXXXXXX-XX |
| LEAD SERIAL NUMBER: | XXXXXXX-XX |
| LEAD IMPLANT DATE: | 01/02/2011 |

EPISODE COUNT

| THERAPY COUNTS: | 5 | |
|---|---|---|
| TYPE | RECENT* | TOTAL** |
| SHOCKS DELIVERED | 3 | 3 |
| SHOCKS ABORTED | 0 | 0 |
| ANTI-TACHY PACINGS | 2 | 2 |
| RECENT EPISODES: | 1 | |
| SINCE: | 01/01/2012 | |
| TYPE | RECENT* | TOTAL** |
| ATRIAL FIBRILLATION | 1 | 1 |
| SVT | 0 | 0 |
| VF | 0 | 0 |
| VT1 | 0 | 0 |
| VT2 | 0 | 0 |

* SINCE COUNTERS LAST CLEARED: 01/01/2012, 10:30AM    **SINCE IMPLANTATION: 01/01/2010

| PATIENT NAME: ACKERMAN, KENDRA | INTERROGATED: 20-MAR-14, 22:05 | STATUS: FINAL |
| --- | --- | --- |
| D.O.B.: 02-FEB-1948 | UPLOADED: 20-MAR-14, 22:10 | ELECTRONICALLY SIGNED BY: |
| MRN #: 101-593-814 | REASON FOR INTERROGATION: | UNGAB, GIL |
| VISIT #: 61527632 | SHORTNESS OF BREATH, DIZZINESS | DATE/TIME: 21-MAR-14, 08:15 |
| LOCATION: SHARP CHULA VISTA ED | | |

VT THERAPIES

VT THERAPIES: TURNED ON

| TYPE | RATE BPM | DETECTION | ANTI-TACHY PACING | SHOCKS | DETAILS |
| --- | --- | --- | --- | --- | --- |
| VF | 195 | 12/18 | - | 30JX5 | STABILITY |
| FASTVT | 165 | 8 | RAMPX6 | 20JX1, 30JX5 | |
| VTMON | 145 | 12 | - | - | FFRW FILTER |
| AT | 190 | | | | XYZ XYZ XYZ |
| P-IEGM | - | - | - | - | XYZ |

MAGNET MODE

| MAGNET MODE: | ON |
| --- | --- |
| PACING: | NO EFFECT |
| TACHY: | DISABLED |

THIS PATIENT HAS AN ICD. PLACING A MAGNET OVER THE DEVICE WILL INHIBIT ALL TACHYARRHYTHMIA THERAPIES BUT WILL HAVE NO EFFECT ON THE PACEMAKER FUNCTIONALITY OF THE DEVICE

PLEASE LIMIT ELECTROCAUTERY TO SHORT BURSTS (MAXIMUM 2 SECONDS) SINCE PACING OUTPUT WILL CONTINUE TO BE INHIBITED DURING ELECTROCAUTERY. IN PACEMAKER DEPENDENT PATIENTS, ELECTRICAL NOISE FROM ELECTROCAUTERY MAY INHIBIT PACING SIGNIFICANTLY AND LEAD TO A CLINICALLY RELEVANT DECREASE IN CARDIAC OUTPUT.

MRI SAFETY

| MRI CONDITIONAL: | NOT CONDITIONALLY APPROVED |
| --- | --- |
| THIS DEVICE IS NOT APPROVED FOR USE DURING AN MRI. PLEASE CALL MANUFACTURER FOR ADDITIONAL INFORMATION. THE NUMBER IS LISTED BELOW: | |
| [DEVICE COMPANY]: | XXX-XXX-XXXX |

- END GENEVA REPORT -

STATUS REPORT

TO: PHYSICIAN GILANTHONY UNGAB

| | EVIA DR-T (SN 66154262) | LAST MESSAGE: JUL 25, 2012 |
| | PM IMPLANTED JUN 27, 2012 | LAST CLINIC FOLLOW-UP: JUL 6, 2012 |

STATUS: NO ANOMALIES

STATUS - SUMMARY:
STATUS SUMMARY FOR PATIENT ID "HERNANDEZ ELVIRA"
AUTOMATIC REMARK: NO ANOMALIES DETECTED.

STATUS - DEVICE:

| BATTERY | |
|---|---|
| STATUS | OK |
| DATE OF IMPLANTATION | JUL 27, 2012 1:02:02 PM |
| HOME MONITORING | |
| MESSAGE TYPE | TIME TRIGGERED |
| DEVICE MESSAGE CREATED ON | JUL 25, 2012 1:02:00 AM |
| END OF LAST MONITORING INTERVAL | JUL 25, 2012 1:02:00 AM |
| TRANSMITTER | |
| TRANSMITTER SN | 48303648 |
| LAST TRANSMISSION RECEIVED ON | JUL 25, 2012 1:03:14 AM |

BATTERY STATUS

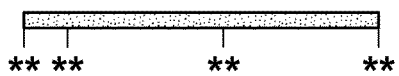

STATUS - LEAD:

| RA LEAD - SETROX S 45, BIO, IMPLANTED JUN 27, 2012 | 24H | SINCE JUL 8, 2012 1:02:00 AM MEAN VALUES, ** MIN VALUES |
|---|---|---|
| PACING IMPEDANCE [OHM] | 488 | 500 |
| PACING THRESHOLD [V] | 0.8 | 0.8 |
| LAST THRESHOLD MEASUREMENT [RA] | JUL 20, 2012 2:01:26 AM | |
| CAPTURE CONTROL STATUS | OK | |
| SENSING AMPLITUDE [DAILY MEAN] [MV] | 4.5 | 4.8 |
| SENSING AMPLITUDE [DAILY MIN] [MV] | 3.4 | 3.2** |
| LEAD CHECK | OK | |
| PACING POLARITY | BIPOLAR | |
| SENSING POLARITY | BIPOLAR | |

FIG. 31B

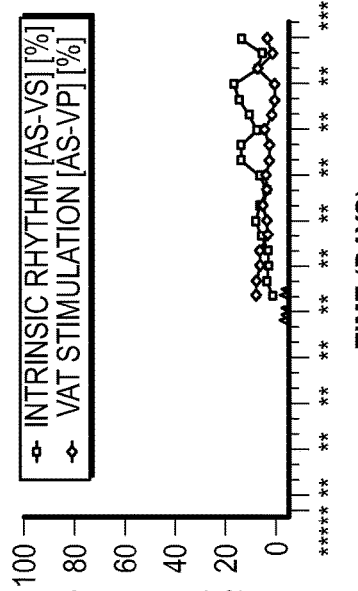
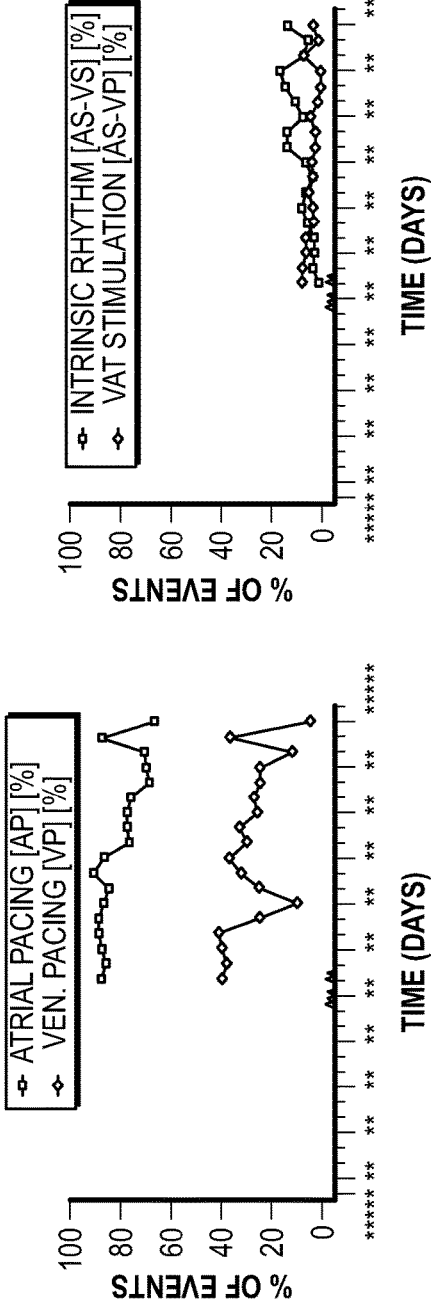
FIG. 31D

REPORTING

PATIENT SEARCH  INTERROGATION INBOX  REPORTING  READING SETTINGS

WELCOME, DR. UNGAB  HELP

490

REQUIRED FIELDS ARE MARKED WITH AN ASTERISK (*)

REPORT TYPE:* [SELECT... ▶]

TIME FRAME:* [SELECT...] TO: [SELECT... ▶]

REPORT FORMAT:* [SELECT... ▶]

FIG. 34

PATIENT SEARCH INTERROGATION INBOX REPORTING READING SETTINGS HELP

WELCOME, DR. UNGAB

REPORTING

REQUIRED FIELDS ARE MARKED WITH AN ASTERISK (*)

REPORT TYPE:* [SELECT... ▶]
INTERROGATION STATISTIC
BILLING

TIME FRAME:*

REPORT FORMAT:* [SELECT... ▶]

REPORTING

PATIENT SEARCH   INTERROGATION INBOX   REPORTING   READING SETTINGS   HELP

WELCOME, DR. UNGAB

490

REQUIRED FIELDS ARE MARKED WITH AN ASTERISK (*)

REPORT TYPE:* [BILLING ▶]

FILTER:*       PHYSICIAN(S)     UNGAB, GIL
               [LOCATION(S)]    [DEFAULT: NONE]
               [CPT CODE(S)]    [DEFAULT: NONE]
               [DIAGNOSIS CODE(S)]  [DEFAULT: NONE]

TIME FRAME:*   [SELECT...]  TO:  [SELECT...]

REPORT FORMAT:*  [SELECT... ▶]

[RESET]

FIG. 36

REPORTING

REQUIRED FIELDS ARE MARKED WITH AN ASTERISK (*)

REPORT TYPE:* [BILLING ▼]

FILTER:* PHYSICIAN(S) UNGAB, GIL

FILTER: LOCATION(S)
☐ UNGAB MEDICAL CENTER
☐ SHARP CHULA VISTA
☐ REMOTE MONITORING

SELECT: ALL NONE [DONE]

TIME FRAME:* [SELECT...] TO: [SELECT...]

REPORT FORMAT:* [SELECT... ▼]

PATIENT SEARCH  INTERROGATION INBOX  REPORTING  READING SETTINGS  HELP

WELCOME, DR. UNGAB

[RESET]

REPORTING

REQUIRED FIELDS ARE MARKED WITH AN ASTERISK (*)

REPORT TYPE:* [BILLING ▼]

FILTER:* PHYSICIAN(S) UNGAB, GIL

FILTER: LOCATION(S)
☐ UNGAB MEDICAL CENTER
☑ SHARP CHULA VISTA
☐ REMOTE MONITORING
SELECT: ALL NONE [DONE]

TIME FRAME:* [SELECT... ▼] TO: [SELECT...]

REPORT FORMAT:* [SELECT... ▼]

[RESET]

PATIENT SEARCH   INTERROGATION INBOX   REPORTING   READING SETTINGS   HELP

WELCOME, DR. UNGAB

REPORTING

PATIENT SEARCH   INTERROGATION INBOX   REPORTING   READING SETTINGS   HELP

WELCOME, DR. UNGAB

490

REQUIRED FIELDS ARE MARKED WITH AN ASTERISK (*)

REPORT TYPE:* [BILLING ▶]

FILTER:*
PHYSICIAN(S)    UNGAB, GIL
[LOCATION(S)]   SHARP CHULA VISTA
[CPT CODE(S)]   [DEFAULT: NONE]
[DIAGNOSIS CODE(S)]   [DEFAULT: NONE]

TIME FRAME:*   [SELECT...]   TO:   [SELECT...]

REPORT FORMAT:*   [SELECT... ▶]

[RESET]

FIG. 39

REPORTING

PATIENT SEARCH   INTERROGATION INBOX   REPORTING   READING SETTINGS   HELP

WELCOME, DR. UNGAB

490

REQUIRED FIELDS ARE MARKED WITH AN ASTERISK (*)

REPORT TYPE:* [BILLING ▼]

FILTER:*

PHYSICIAN(S)   UNGAB, GIL

[LOCATION(S)]   SHARP CHULA VISTA

FILTER: CPT CODE(S)

IN PERSON
- ☐ 93288 - PACEMAKER (NO PROGRAMMING EVALUATION)
- ☐ 93279 - PACEMAKER (SINGLE LEAD)
- ☐ 93280 - PACEMAKER (DUAL CHAMBER)
- ☐ 93281 - PACEMAKER (CRT-P)
- ☐ 93289 - AICD (NO PROGRAMMING EVALUATION)
- ☐ 93282 - AICD (SINGLE LEAD)
- ☐ 93283 - AICD (DUAL CHAMBER)
- ☐ 93284 - AICD (CRT-D)

REMOTE MONITORING
- ☐ 93296 - PACEMAKER/AICD TECHNICAL FEE (90 DAYS)

SELECT: ALL   NONE

[DONE]

TIME FRAME:*

REPORT FORMAT:*

[RESET]

FIG. 40

REPORTING

REQUIRED FIELDS ARE MARKED WITH AN ASTERISK (*)

REPORT TYPE:* [BILLING ▶]

FILTER:*

PHYSICIAN(S)   UNGAB, GIL

[LOCATION(S)]   SHARP CHULA VISTA

FILTER: CPT CODE(S)

IN PERSON
- ☑ 93288 - PACEMAKER (NO PROGRAMMING EVALUATION)
- ☐ 93279 - PACEMAKER (SINGLE LEAD)
- ☐ 93280 - PACEMAKER (DUAL CHAMBER)
- ☐ 93281 - PACEMAKER (CRT-P)
- ☑ 93289 - AICD (NO PROGRAMMING EVALUATION)
- ☐ 93282 - AICD (SINGLE LEAD)
- ☐ 93283 - AICD (DUAL CHAMBER)
- ☐ 93284 - AICD (CRT-D)

REMOTE MONITORING
- ☐ 93296 - PACEMAKER/AICD TECHNICAL FEE (90 DAYS)

SELECT:  ALL   NONE          [DONE]

TIME FRAME:*

REPORT FORMAT:*

[RESET]

490

WELCOME, DR. UNGAB
PATIENT SEARCH  INTERROGATION INBOX  REPORTING  READING SETTINGS  HELP

FIG. 41

REPORTING

PATIENT SEARCH  INTERROGATION INBOX  REPORTING  READING SETTINGS  HELP

WELCOME, DR. UNGAB

490

REQUIRED FIELDS ARE MARKED WITH AN ASTERISK (*)

REPORT TYPE:* [ BILLING ▶ ]

FILTER:*
PHYSICIAN(S)  UNGAB, GIL
[ LOCATION(S) ]  SHARP CHULA VISTA
[ CPT CODE(S) ]  93288 - PACEMAKER (NO PROGRAMMING EVALUATION)
                 93289 - AICD (NO PROGRAMMING EVALUATION)
[ DIAGNOSIS CODE(S) ]  [DEFAULT: NONE]

TIME FRAME:* [ SELECT... ] TO: [ SELECT... ]

REPORT FORMAT:* [ SELECT... ▶ ]

[ RESET ]

FIG. 42

REPORTING

REQUIRED FIELDS ARE MARKED WITH AN ASTERISK (*)

490

PATIENT SEARCH   INTERROGATION INBOX   REPORTING   READING SETTINGS   HELP

WELCOME, DR. UNGAB

REPORT TYPE:*  [BILLING ▶]

FILTER:*

PHYSICIAN(S)   UNGAB, GIL

[LOCATION(S)]   SHARP CHULA VISTA

[CPT CODE(S)]   93288 - PACEMAKER (NO PROGRAMMING EVALUATION)
                93289 - AICD (NO PROGRAMMING EVALUATION)

FILTER: DIAGNOSIS CODE(S)
☐ V45.01 - PACEMAKER INSITU
☐ V45.02 - AICD INSITU
☐ 780.1 - PRE SYNCOPE
☐ 780.2 - SYNCOPE
☐ 786.05 - SHORTNESS OF BREATH
☐ 780.4 - DIZZINESS
☐ 785.1 - PALPITATIONS
☐ 414.8 - ISCHEMIC CARDIOMYOPOTHY

SELECT: ALL  NONE        [DONE]

TIME FRAME:*

REPORT FORMAT:*

[RESET]

FIG. 43

REPORTING

PATIENT SEARCH   INTERROGATION INBOX   REPORTING   READING SETTINGS   HELP

WELCOME, DR. UNGAB

490

REQUIRED FIELDS ARE MARKED WITH AN ASTERISK (*)

REPORT TYPE:*  [ BILLING ▶ ]

FILTER:*

PHYSICIAN(S)   UNGAB, GIL

[ LOCATION(S) ]   SHARP CHULA VISTA

[ CPT CODE(S) ]   93288 - PACEMAKER (NO PROGRAMMING EVALUATION)
                  93289 - AICD (NO PROGRAMMING EVALUATION)

┌─ FILTER: DIAGNOSIS CODE(S) ────────────────── ◀ ▦ ▶ ─┐
│ ☐ V45.01 - PACEMAKER INSITU                          │
│ ☐ V45.02 - AICD INSITU                               │
│ ☐ 780.1 - PRE SYNCOPE                                │
│ ☐ 780.2 - SYNCOPE                                    │
│ ☑ 786.05 - SHORTNESS OF BREATH                       │
│ ☑ 780.4 - DIZZINESS                                  │
│ ☑ 785.1 - PALPITATIONS                               │
│ ☐ 414.8 - ISCHEMIC CARDIOMYOPOTHY                    │
│ SELECT: ALL NONE           [ DONE ]          │
└──────────────────────────────────────────────────────┘

TIME FRAME:*

REPORT FORMAT:*

[ RESET ]

FIG. 44

REPORTING

PATIENT SEARCH   INTERROGATION INBOX   REPORTING   READING SETTINGS   HELP

WELCOME, DR. UNGAB

490

REQUIRED FIELDS ARE MARKED WITH AN ASTERISK (*)

REPORT TYPE:* [ BILLING ▶ ]

FILTER:*   PHYSICIAN(S)   UNGAB, GIL
    [ LOCATION(S) ]   SHARP CHULA VISTA
    [ CPT CODE(S) ]   93288 - PACEMAKER (NO PROGRAMMING EVALUATION)
                               93289 - AICD (NO PROGRAMMING EVALUATION)
    [ DIAGNOSIS CODE(S) ]   786.05 - SHORTNESS OF BREATH
                               780.4 - DIZZINESS
                               785.1 - PALPITATIONS

TIME FRAME:*   [ SELECT... ]   TO:   [ SELECT... ]

REPORT FORMAT:*   [ SELECT... ▶ ]

[ RESET ]

FIG. 45

PATIENT SEARCH   INTERROGATION INBOX   REPORTING   READING SETTINGS   HELP

WELCOME, DR. UNGAB

REPORTING

490

REQUIRED FIELDS ARE MARKED WITH AN ASTERISK (*)

REPORT TYPE:*  [ BILLING ▶ ]

FILTER:*       PHYSICIAN(S)      UNGAB, GIL
               [ LOCATION(S) ]   SHARP CHULA VISTA
               [ CPT CODE(S) ]   93288 - PACEMAKER (NO PROGRAMMING EVALUATION)
                                 93289 - AICD (NO PROGRAMMING EVALUATION)
               [ DIAGNOSIS CODE(S) ]  786.05 - SHORTNESS OF BREATH
                                     780.4 - DIZZINESS
                                     785.1 - PALPITATIONS

TIME FRAME:*   [ 22-MAR-14 ]  TO:  [ 29-MAR-14 ]

REPORT FORMAT:*  [ SELECT... ▶ ]
                 .PDF
                 .CSV

[ RESET ]

FIG. 46

REPORTING

PATIENT SEARCH   INTERROGATION INBOX   REPORTING   READING SETTINGS   HELP

WELCOME, DR. UNGAB

490

REPORTING

REQUIRED FIELDS ARE MARKED WITH AN ASTERISK (*)

REPORT TYPE:*   [BILLING ▼]

FILTER:*   PHYSICIAN(S)   UNGAB, GIL
          [LOCATION(S)]   SHARP CHULA VISTA
          [CPT CODE(S)]   93288 - PACEMAKER (NO PROGRAMMING EVALUATION)
                          93289 - AICD (NO PROGRAMMING EVALUATION)
          [DIAGNOSIS CODE(S)]   786.05 - SHORTNESS OF BREATH
                                780.4 - DIZZINESS
                                785.1 - PALPITATIONS

TIME FRAME:*   [22-MAR-14]   TO:   [29-MAR-14]

REPORT FORMAT:*   [.PDF ▼]

[RESET]   [DOWNLOAD]

FIG. 47

BILLING REPORT
TIME FRAME: 22-MAR-14 TO 29-MAR-14
PHYSICIAN(S): UNGAB, GIL
LOCATION(S): SHARP CHULA VISTA

CPT CODE(S): 93288 - PACEMAKER (NO PROGRAMMING EVALUATION)
93289 - AICD (NO PROGRAMMING EVALUATION)
DIAGNOSIS CODE(S): 786.05 - SHORTNESS OF BREATH
780.4 - DIZZINESS
785.1 - PALPITATIONS

CREATED: 31-MAR-14, 08:15
BY: UNGAB, GIL

500

| | PHYSICIAN | DATE OF DICTATION | PATIENT IDENTIFIERS | VISIT # | LOCATION | CPT CODE(S) | DIAGNOSIS CODE(S) | DATE OF INTERROGATION |
|---|---|---|---|---|---|---|---|---|
| 1 | UNGAB, GIL | 22-MAR-14 | ACKERMAN, KENDRA<br>D.O.B.: 10-OCT-54<br>MRN #: 6572891234 | 352698412 | SHARP CHULA VISTA | 93288 - PACEMAKER (NO PROGRAMMING EVALUATION) | 786.05 - SHORTNESS OF BREATH<br>780.4 - DIZZINESS | 21-MAR-14 |
| 2 | UNGAB, GIL | 22-MAR-14 | WANG, XIXE<br>D.O.B.: 10-OCT-54<br>MRN #: 6572891234 | 995622347 | SHARP CHULA VISTA | 93288 - PACEMAKER (NO PROGRAMMING EVALUATION) | 786.05 - SHORTNESS OF BREATH | 21-MAR-14 |
| 3 | UNGAB, GIL | 23-MAR-14 | JAMES, EDWARD<br>D.O.B.: 10-OCT-54<br>MRN #: 6572891234 | 454778912 | SHARP CHULA VISTA | 93289 - AICD (NO PROGRAMMING EVALUATION) | 786.05 - SHORTNESS OF BREATH | 22-MAR-14 |
| 4 | UNGAB, GIL | 24-MAR-14 | BENITEZ, JUANA<br>D.O.B.: 10-OCT-54<br>MRN #: 6572891234 | 985367454 | SHARP CHULA VISTA | 93288 - PACEMAKER (NO PROGRAMMING EVALUATION) | 786.05 - SHORTNESS OF BREATH<br>780.4 - DIZZINESS | 23-MAR-14 |
| 5 | UNGAB, GIL | 26-MAR-14 | GARCIA, TOMAS<br>D.O.B.: 10-OCT-54<br>MRN #: 6572891234 | 3325 47845 | SHARP CHULA VISTA | 93288 - PACEMAKER (NO PROGRAMMING EVALUATION) | 786.05 - SHORTNESS OF BREATH<br>780.4 - DIZZINESS<br>785.1 - PALPITATIONS | 25-MAR-14 |
| 6 | UNGAB, GIL | 26-MAR-14 | ALLEN, MICHAELA<br>D.O.B.: 10-OCT-54<br>MRN #: 6572891234 | 214475888 | SHARP CHULA VISTA | 93289 - AICD (NO PROGRAMMING EVALUATION) | 786.05 - SHORTNESS OF BREATH<br>785.1 - PALPITATIONS | 25-MAR-14 |
| 7 | UNGAB, GIL | 27-MAR-14 | NEARHOOD, RACHEL<br>D.O.B.: 10-OCT-54<br>MRN #: 6572891234 | 652244141 | SHARP CHULA VISTA | 93289 - AICD (NO PROGRAMMING EVALUATION) | 786.05 - SHORTNESS OF BREATH<br>780.4 - DIZZINESS | 26-MAR-14 |
| 8 | UNGAB, GIL | 28-MAR-14 | JACKSON, EZRA<br>D.O.B.: 10-OCT-54<br>MRN #: 6572891234 | 332657774 | SHARP CHULA VISTA | 93288 - PACEMAKER (NO PROGRAMMING EVALUATION) | 780.4 - DIZZINESS | 27-MAR-14 |

TOTAL BILLINGS: 8

- END OF BILLING REPORT -

FIG. 48

MANAGEMENT OF IMPLANTABLE CARDIAC DEVICE INTERROGATION DATA AND REPORTS

CROSS-REFERENCE TO RELATED APPLICATION(S)

This application claims priority to U.S. Application No. 61/990,064 filed on May 7, 2014, titled MANAGEMENT OF IMPLANTABLE CARDIAC DEVICE INTERROGATION DATA AND REPORTS, the disclosure of which is hereby incorporated by reference in its entirety.

BACKGROUND

Implantable cardiac devices, including pacemakers and implantable cardioverter-defibrilators, are sometimes used in the care of patients having cardiac conditions. During operation, these devices typically generate and store device data that records information about the device's operation and the patient's condition.

Device data can be obtained from an implantable cardiac device by interrogating the device. Interrogation can occur at home, such as through a home monitoring device, or at a point of care, such as at a hospital or clinic. Home monitoring typically occurs on a periodic or occasional basis, while point of care interrogations are typically ordered by a requesting physician, as part of a patient's visit to a care facility.

Device data is typically routed through the device manufacturer's own systems, which generates the manufacturer's interrogation report. Such manufacturer's interrogation reports often vary from company to company.

Once the manufacturer's report is obtained, it may be printed out or otherwise sent to a physician for review, such as in an e-mail message. The physician may choose to review the report, and if so, may also pull up and navigate through the patient's medical record to assist in his study of the report and to investigate any noticeable issues or concerns relating to this patient. Once completed, the physician may also choose to make a record of his or her findings. The process can consume a considerable amount of time, and as a result the physician may choose to complete the process only in exceptional circumstances.

Sometimes an interrogation report reveals clinically relevant information. A health care facility may face liability if a physician chooses not to review the interrogation report, or simply forgets, or if the physician does not understand the report and overlooks the clinically relevant information.

SUMMARY

In general terms, this disclosure is directed to management of implantable cardiac device interrogation data and reports. In one possible configuration and by non-limiting example, a reading system manages the interrogation data and reports, such as to assign the interrogation data to one or more physicians for formal review. Various aspects are described in this disclosure, which include, but are not limited to, the following aspects.

One aspect is a method of generating a report relating to an implantable cardiac device, the method being implemented by one or more computing devices, and comprising: receiving, using the one or more computing devices, an implantable cardiac device manufacturer's report associated with the implantable cardiac device; generating, using the one or more computing devices, a summary report from the implantable cardiac device manufacturer's report; generating, using the one or more computing devices, a reading physician note relating to the implantable cardiac device; and generating, using the one or more computing devices, a report relating to the implantable cardiac device, the report including the implantable cardiac device manufacturer's report, the summary report, and the reading physician note.

Another aspect is a method of reviewing interrogation data of an implantable cardiac device, the method comprising: receiving the interrogation data of the implantable cardiac device; assigning, using a computing device, reading of the interrogation data to a first reader; and when the reading of the interrogation data by the first reader does not occur within a predetermined period of time, assigning reading of the interrogation data to a second reader.

A further aspect is a method of generating a reading physician's note associated with an implantable cardiac device, the method comprising: receiving an implantable cardiac device manufacturer's report containing device data associated with the implantable cardiac device; extracting the device data from the implantable cardiac device manufacturer's report; and using the device data to automatically populate one or more fields of the reading physician's note.

Another aspect is a method of electronically signing an implantable cardiac device report, the method comprising: receiving interrogation data at a server computing device associated with an implantable cardiac device; sending data from the server computing device to a remote computing device to generate a user interface for displaying the interrogation data to a physician; and receiving at the server computing device, and from the remote computing device, an input from the physician electronically signing the interrogation data.

Yet another aspect is a method of distributing interrogation data associated with implantable cardiac devices to a physician, the method comprising: receiving interrogation data associated with a first implantable cardiac device, the interrogation data identifying a first medical facility; receiving interrogation data associated with a second implantable cardiac device, the interrogation data identifying a second medical facility different than the first medical facility; and assigning reading of the interrogation data associated with the first and second implantable cardiac devices to a first physician.

A further aspect is a method of formally reviewing implantable cardiac device data, the method comprising: designating a physician as a reader; receiving implantable cardiac device data; and when the implantable cardiac device data is not read according to one or more predetermined criteria, assigning the implantable cardiac device data to be read by the designated reader using a computing device.

Another aspect is a system comprising: one or more processing devices; and one or more computer readable media, wherein the one or more computer readable media store data instructions, which when executed by the one or more processing devices cause the one or more processing devices to: receive an implantable cardiac device manufacturer's report associated with the implantable cardiac device; generate a summary report from the implantable cardiac device manufacturer's report; generate a reading physician note relating to the implantable cardiac device; and generate a report relating to the implantable cardiac device, the report including the implantable cardiac device manufacturer's report, the summary report, and the reading physician note.

Yet another aspect is a system comprising: one or more processing devices; and one or more computer readable media, wherein the one or more computer readable media store data instructions, which when executed by the one or more processing devices cause the one or more processing devices to: receive interrogation data of an implantable cardiac device; assign reading of the interrogation data to a first reader; and when the reading of the interrogation data by the first reader does not occur within a predetermined period of time, assign reading of the interrogation data to a second reader.

A further aspect is a system comprising: one or more processing devices; and one or more computer readable media, wherein the one or more computer readable media store data instructions, which when executed by the one or more processing devices cause the one or more processing devices to: receive an implantable cardiac device manufacturer's report containing device data associated with an implantable cardiac device; extract the device data from the implantable cardiac device manufacturer's report; and use the device data to automatically populate one or more fields of a reading physician's note.

Another aspect is a system comprising: one or more processing devices; and one or more computer readable media, wherein the one or more computer readable media store data instructions, which when executed by the one or more processing devices cause the one or more processing devices to: receive interrogation data associated with an implantable cardiac device; send data to a remote computing device to generate a user interface for displaying the interrogation data to a physician; and receive from the remote computing device an input from the physician electronically signing the interrogation data.

A further aspect is a system comprising: one or more processing devices; and one or more computer readable media, wherein the one or more computer readable media store data instructions, which when executed by the one or more processing devices cause the one or more processing devices to: receive interrogation data associated with a first implantable cardiac device, interrogation data identifying a first medical facility; receive interrogation data associated with a second implantable cardiac device, the interrogation data identifying a second medical facility different than the first medical facility; and assign reading of the interrogation data associated with the first and second implantable cardiac devices to a first physician.

Another aspect is a system comprising: one or more processing devices; and one or more computer readable media, wherein the one or more computer readable media store data instructions, which when executed by the one or more processing devices cause the one or more processing devices to: designate a physician as a reader; receive implantable cardiac device data; and when the implantable cardiac device data is not read according to one or more predetermined criteria, assign the implantable cardiac device data to be read by the designated reader.

Another aspect is any one of the methods illustrated and/or described herein.

Yet another aspect is any one of the systems illustrated and/or described herein.

A further aspect is a system comprising: one or more processing devices; and one or more computer readable media, wherein the one or more computer readable media store data instructions, which when executed by the one or more processing devices cause the one or more processing devices to execute any one or more of the engines illustrated and/or described herein.

BRIEF DESCRIPTION OF THE DRAWINGS

FIG. 9 is a screen shot illustrating an example of an administrative inbox display, such as generated by an administrative inbox engine of the administrative interface engine shown in FIG. 8.

FIG. 10 (including FIGS. 10A and 10B) is a screen shot illustrating an example of routing rules definition display, such as generated by a routing rules definition engine of the administrative interface engine shown in FIG. 8.

FIG. 16 is a screen shot of an example reader inbox display, such as generated by a reader inbox engine of the reader interface engine shown in FIG. 15.

FIG. 18 is a screen shot of a details display, such as generated by the summary report engine, shown in FIG. 15.

FIG. 19 is a screen shot illustrating an example physician note interface display, such as generated by the physician note interface engine shown in FIG. 15.

FIG. 21 is a screen shot of an example status selection page of the example physician note interface engine shown in FIG. 19.

FIG. 22 is a screen shot illustrating an example of the physician note interface display shown in FIG. 19, and further illustrating the selection of one or more billing codes, such as Current Procedural Terminology (CPT) codes.

FIG. 23 is a screen shot illustrating an example of the physician note interface display shown in FIG. 19, and further illustrating the selection of one or more billing codes, such as diagnosis codes.

FIG. 26 is a screen shot illustrating another example of a physician note interface display after the reading physician's findings/interpretations and conclusion have been entered.

FIG. 27 is a screen shot illustrating the example physician note interface display of FIG. 26, and further illustrating an electronic signature process involving the electronic signature engine shown in FIG. 15.

FIG. 29 illustrates an example physician note of the final device interrogation report.

FIG. 30 (including FIGS. 30A-30C) illustrates an example summary report of the final device interrogation report.

FIG. 34 is a screen shot illustrating an example of a reporting interface display.

FIG. 35 is another screen shot of the example reporting interface display shown in FIG. 34.

FIG. 36 is another screen shot of the example reporting interface display shown in FIG. 34.

FIG. 37 is another screen shot of the example reporting interface display shown in FIG. 34.

FIG. 38 is another screen shot of the example reporting interface display shown in FIG. 34.

FIG. 39 is another screen shot of the example reporting interface display shown in FIG. 34.

FIG. 40 is another screen shot of the example reporting interface display shown in FIG. 34.

FIG. 41 is another screen shot of the example reporting interface display shown in FIG. 34.

FIG. 42 is another screen shot of the example reporting interface display shown in FIG. 34.

FIG. 43 is another screen shot of the example reporting interface display shown in FIG. 34.

FIG. 44 is another screen shot of the example reporting interface display shown in FIG. 34.

FIG. 45 is another screen shot of the example reporting interface display shown in FIG. 34.

FIG. 46 is another screen shot of the example reporting interface display shown in FIG. 34.

FIG. 47 is another screen shot of the example reporting interface display shown in FIG. 34.

FIG. 48 illustrates an example billing report, such as generated by the billing interface engine of the interrogation data management system shown in FIG. 4.

DETAILED DESCRIPTION

Figure 1:
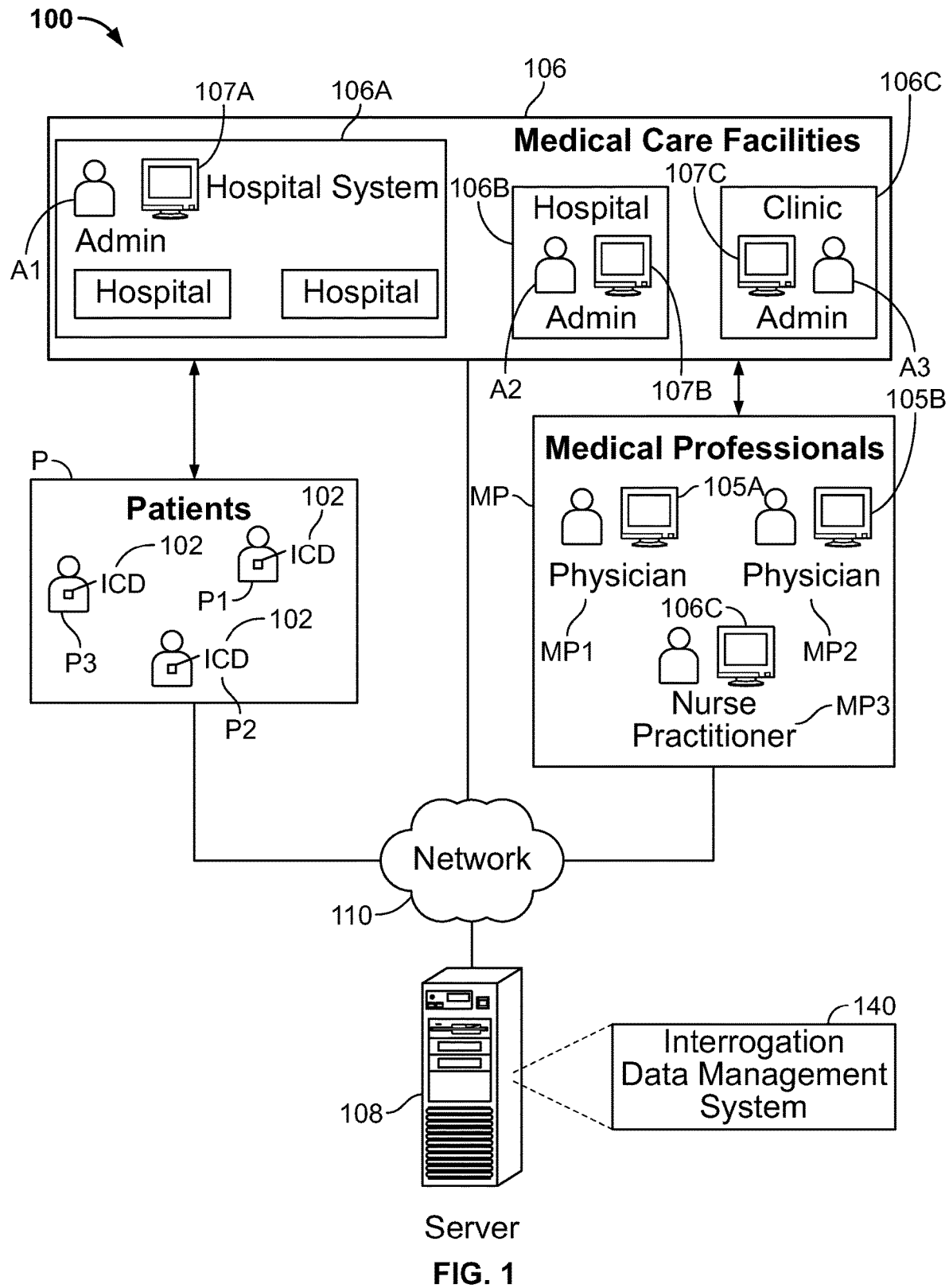
FIG. 1 is a schematic diagram illustrating an example care system involving implantable cardiac devices, and including an interrogation data management system.

Various embodiments will be described in detail with reference to the drawings, wherein like reference numerals represent like parts and assemblies throughout the several views. Reference to various embodiments does not limit the scope of the claims attached hereto. Additionally, any examples set forth in this specification are not intended to be limiting and merely set forth some of the many possible embodiments for the appended claims.

FIG. 1 is a schematic diagram illustrating an example care system 100 involving implantable cardiac devices 102, and including an interrogation data management system 140. The care system also includes medical care facilities 106, patients P, medical professionals MP, and one or more server computing devices 108 generating the interrogation data management system 140.

Examples of medical care facilities 106 include a hospital system 106A, a hospital 106B, and a clinic 106C. A hospital system 106A typically includes multiple hospitals. One or more administrators A are associated with the medical care facilities 106 and interact with the interrogation data management system 140, as described herein. The medical care facilities 106 typically include numerous computing devices 107 (and at least one computing device) through which the administrator A and medical professionals MP can access the interrogation data management system 140 through the data communication network 110, for example. The medical professionals MP can access the interrogation data management system 140 through the data communication network 110, at the numerous computing devices 105. Specifically, administrator A1 located at the hospital system 106A interacts with the interrogation data management system 140 at the computing device 107A. Administrator A2 located at the hospital 106B interacts with the interrogation data management system 140 at the computing device 107B. Administrator A3 located at the clinic 106C interacts with the interrogation data management system 140 at the computing device 107C.

Patients P having implantable cardiac devices 102 (IDCs) are cared for by the medical care facilities 106 and the medical professionals MP associated with those facilities. In some cases the implantable cardiac devices 102 permit remote monitoring, such as by wirelessly communicating device data to a remote monitoring device at the patient's home or work. The transfer of data from the implantable cardiac device 102 to another device is often referred to as an interrogation, and the data obtained therefrom is often referred to as the interrogation data. Interrogations may also occur when the patient P visits a medical care facility 106. For example, when a medical professional MP learns that the patient P has an implantable cardiac device 102, the medical professional MP may order an interrogation of that device 102.

The medical professionals MP are people with medical training, including physicians and nurse practitioners, for example. Some medical professionals MP provide direct care to patients P, while other medical professionals MP may not interact directly with the patient P but may be involved in other ways, such as reviewing the interrogation data, for example. In either case, the medical professionals MP can all be said to be caregivers who are providing care to the patient P in one form or another. One example of a physician is an electrophysiologist (EPs) who specializes in diagnosing and treating problems with the heart's electrical system. Other physicians can be involved as well, such as an emergency room physician, a primary caregiver, and the like. In some embodiments nurse practitioners assist physicians with certain tasks, such as some of the tasks described herein.

Figure 3:
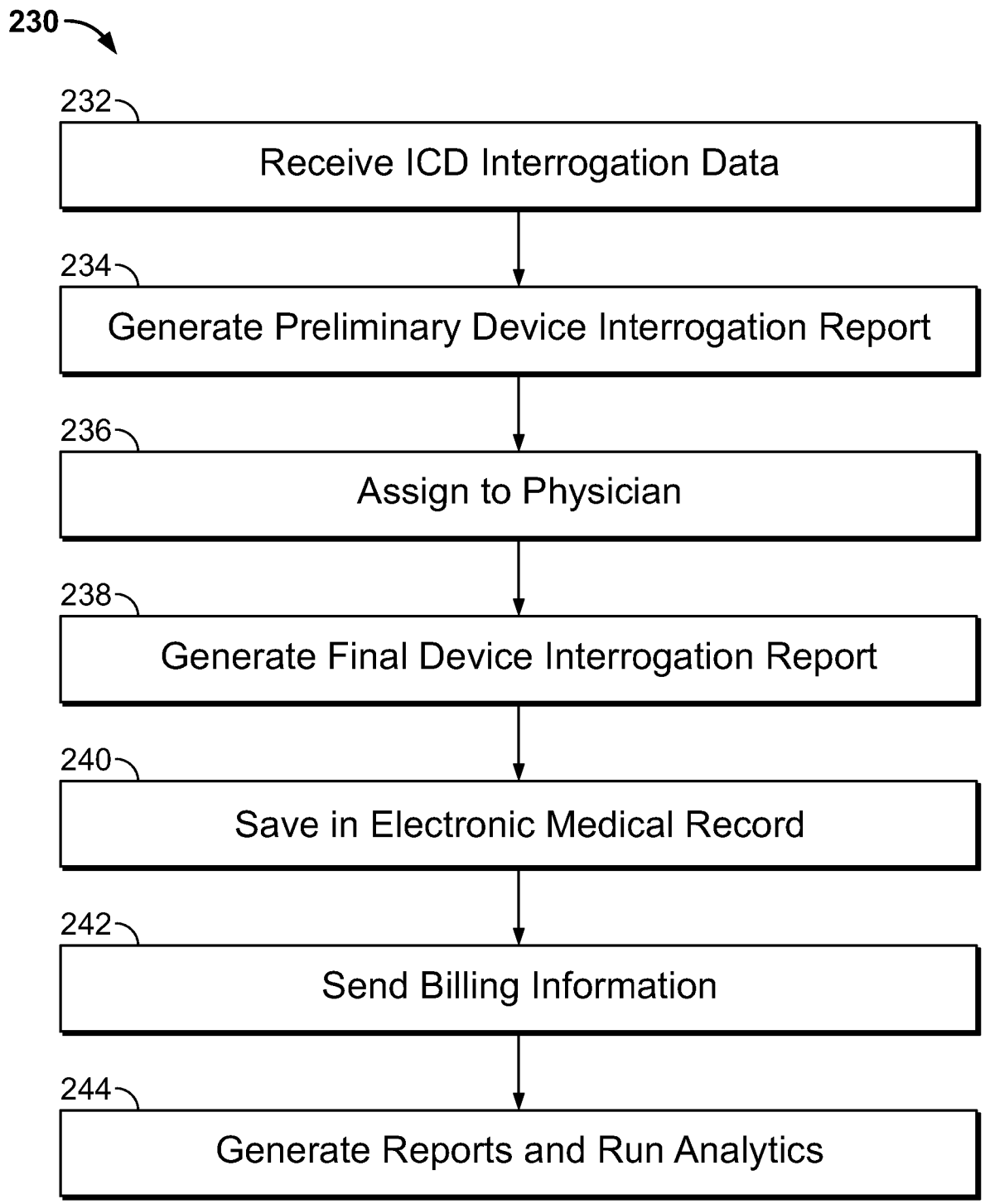
FIG. 3 is a flow chart illustrating an example method of managing implantable cardiac device interrogation data.

One or more server computing devices 108 are in data communication with a data communication network 110. In this example, the one or more server computing devices 108 generate an interrogation data management system 140. An example of the interrogation data management system 140 is illustrated and described with reference to FIG. 4, as well as throughout the present disclosure. FIG. 3 also illustrates a method that can be performed by the interrogation data management system 140 and the one or more server computing devices 108 shown in FIG. 1.

The data communication network 110 may include a local area network, or a wide area networking environment. When used in a local area networking environment or a wide area networking environment (such as the Internet), the interrogation data management system 140 is typically connected to the network 110 through a network interface, such as an Ethernet interface. Other possible embodiments use other communication devices. For example, some embodiments of the interrogation data management system 140 include a modem for communicating across the network 110.

Figure 2:
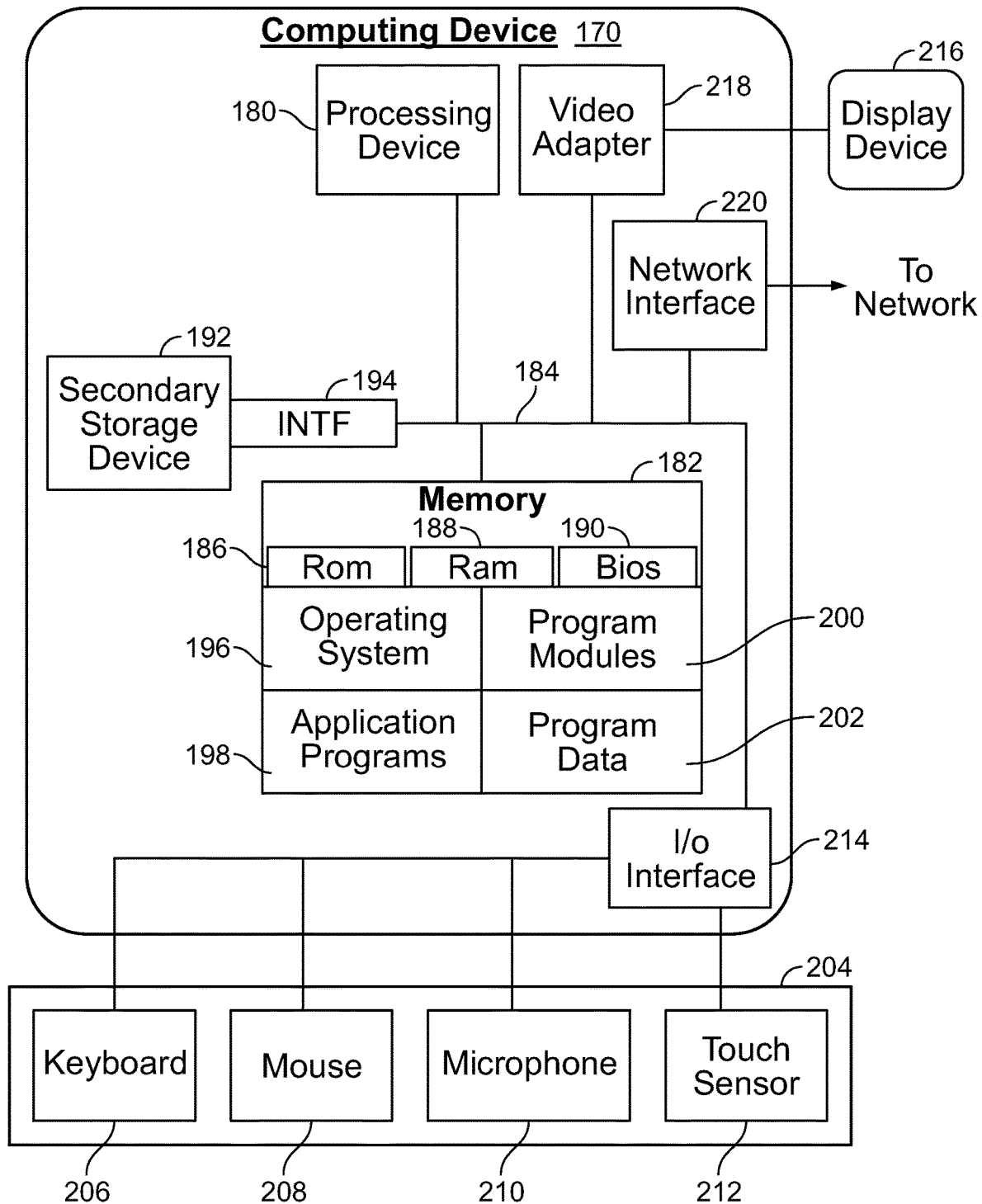
FIG. 2 is a schematic block diagram illustrating an exemplary architecture of a computing device that can be used to implement aspects of the present disclosure, including any of the computing devices of the example care system shown in FIG. 1.

FIG. 2 is a schematic block diagram illustrating an exemplary architecture of a computing device that can be used to implement aspects of the present disclosure, including any of the plurality of medical care facility 106 computing devices 107, medical professional MP computing devices 105, or server computing devices 108 shown in FIG. 1 or elsewhere described herein. For example, the computing device illustrated in FIG. 2 can be used to execute the operating system 196, application programs 198, and software modules 200 (including the software engines) described herein. By way of example, the computing device will be described below as the server computing device 170. To avoid undue repetition, this description of the computing device will not be separately repeated herein for each of the other computing devices, but such devices can also be configured as illustrated and described with reference to FIG. 2.

The computing device 170 includes, in some embodiments, at least one processing device 180, such as a central processing unit (CPU). A variety of processing devices are available from a variety of manufacturers, for example, Intel or Advanced Micro Devices. In this example, the computing device 170 also includes a system memory 182, and a system bus 184 that couples various system components including the system memory 182 to the processing device 180. The system bus 184 is one of any number of types of bus structures including a memory bus, or memory controller; a peripheral bus; and a local bus using any of a variety of bus architectures.

Examples of computing devices suitable for the computing device 170 include a desktop computer, a laptop computer, a tablet computer, a mobile computing device (such as a smart phone, an iPod® or iPad® mobile digital device, or other mobile devices), or other devices configured to process digital instructions.

The system memory 182 includes read only memory 186 and random access memory 188. A basic input/output system 190 containing the basic routines that act to transfer information within computing device 170, such as during start up, is typically stored in the read only memory 186.

The computing device 170 also includes a secondary storage device 192 in some embodiments, such as a hard disk drive, for storing digital data. The secondary storage device 192 is connected to the system bus 184 by a secondary storage interface 194. The secondary storage devices 192 and their associated computer readable media provide nonvolatile storage of computer readable instructions (including application programs and program modules), data structures, and other data for the computing device 170.

Although the exemplary environment described herein employs a hard disk drive as a secondary storage device, other types of computer readable storage media are used in other embodiments. Examples of these other types of computer readable storage media include magnetic cassettes, flash memory cards, digital video disks, Bernoulli cartridges, compact disc read only memories, digital versatile disk read only memories, random access memories, or read only memories. Some embodiments include non-transitory media. Additionally, such computer readable storage media can include local storage or cloud-based storage.

A number of program modules can be stored in secondary storage device 192 or memory 182, including an operating system 196, one or more application programs 198, other program modules 200 (such as the software engines described herein), and program data 202. The computing device 170 can utilize any suitable operating system, such as Microsoft Windows™, Google Chrome™, Apple OS, and any other operating system suitable for a computing device.

In some embodiments, a user provides inputs to the computing device 170 through one or more input devices 204. Examples of input devices 204 include a keyboard 206, mouse 208, microphone 210, and touch sensor 212 (such as a touchpad or touch sensitive display). Other embodiments include other input devices 204. The input devices are often connected to the processing device 180 through an input/output interface 214 that is coupled to the system bus 184. These input devices 204 can be connected by any number of input/output interfaces, such as a parallel port, serial port, game port, or a universal serial bus. Wireless communication between input devices and the interface 214 is possible as well, and includes infrared, BLUETOOTH® wireless technology, 802.11a/b/g/n, cellular, or other radio frequency communication systems in some possible embodiments.

In this example embodiment, a display device 216, such as a monitor, liquid crystal display device, projector, or touch sensitive display device, is also connected to the system bus 184 via an interface, such as a video adapter 218. In addition to the display device 216, the computing device 170 can include various other peripheral devices (not shown), such as speakers or a printer.

When used in a local area networking environment or a wide area networking environment (such as the Internet), the computing device 170 is typically connected to the network 112 through a network interface 220, such as an Ethernet interface. Other possible embodiments use other communication devices. For example, some embodiments of the computing device 170 include a modem for communicating across the network.

The computing device 170 typically includes at least some form of computer readable media. Computer readable media includes any available media that can be accessed by the computing device 170. By way of example, computer readable media include computer readable storage media and computer readable communication media.

Computer readable storage media includes volatile and nonvolatile, removable and non-removable media implemented in any device configured to store information such as computer readable instructions, data structures, program modules or other data. Computer readable storage media includes, but is not limited to, random access memory, read only memory, electrically erasable programmable read only memory, flash memory or other memory technology, compact disc read only memory, digital versatile disks or other optical storage, magnetic cassettes, magnetic tape, magnetic disk storage or other magnetic storage devices, or any other medium that can be used to store the desired information and that can be accessed by the computing device 170. Computer readable storage media does not include computer readable communication media.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are also included within the scope of computer readable media.

The computing device illustrated in FIG. 2 is also an example of programmable electronics, which may include one or more such computing devices, and when multiple computing devices are included, such computing devices can be coupled together with a suitable data communication network so as to collectively perform the various functions, methods, or operations disclosed herein.

FIG. 3 is a flow chart illustrating an example method 230 of managing implantable cardiac device interrogation data. In some embodiments the method 230 is performed by receiving the data from an implantable cardiac device manufacturer's system (such as through a web server). Examples of this operation are described in further detail in Applicant's co-pending patent application, U.S. Publication No. 2013/0317852, titled MEDICAL DEVICE INFORMATION PORTAL, the disclosure of which is hereby incorporated by reference in its entirety. For example, FIG. 19 of the co-pending application illustrates a process of obtaining data from one of multiple manufacturers through a server 262. In this example, the method 230 includes operations 232, 234, 236, 238, 240, 242, and 244.

In this example, the method 230 includes operations, including: receiving implantable cardiac device interrogation data 232, generating a preliminary device interrogation report 234; assigning to a reading physician 236, generating a final device interrogation report 238, saving in an electronic medical record 240, sending billing information 242, and generating reports and running analytics 244.

The operation 232 is performed to receive all data relevant to a specific implantable cardiac device. In some embodiments, the implantable cardiac device interrogation data is received at the one or more computing devices. The interrogation data may include a manufacturer's report associated with the implantable cardiac device.

The operation 234 is performed to generate a preliminary device interrogation report. In some embodiments, a summary report is generated, using one or more computing devices 170 (FIG. 2), from the implantable cardiac device manufacturer's report. In addition, a reading physician note relating to the implantable cardiac device is generated, using one or more computing devices 170 (FIG. 2). The operation 234 is performed by generating, using the one or more computing devices 170 (FIG. 2), a report relating to the implantable cardiac device, the report including the implantable cardiac device manufacturer's report, the summary report, and the reading physician note.

The operation 236 is then performed to assign the report generated in S234 to a physician to review. In some embodiments, the physician tasked to read the report generated in S234 may include medical professionals MP (i.e. physicians MP1 or MP2, or nurse practitioner MP3). It is imperative that the report be reviewed in a timely manner, as point of care interrogations can be related to time-sensitive procedures. After the interrogation data of the implantable cardiac device is received, the reading of the interrogation data task is assigned to a first reader. In the event the first reader does not read the interrogation data within a predetermined period of time, the task is then reassigned to a second reader.

The operation 238 is then performed to generate a final device interrogation report. In some embodiments, the final device interrogation report includes the reading physician's note associated with an implantable cardiac device, a summary report, and an implantable cardiac device manufacturer's report. Once the implantable cardiac device manufacturer's report containing device data associated with the implantable cardiac device is received, the device data from the implantable cardiac device manufacturer's report can be extracted. The physician can use the device data to automatically populate one or more fields of the reading physician's note. Once the reading physician's note is completed, the physician can electronically sign the implantable cardiac device report.

The operation 240 is then performed to save the final device interrogation report in an electronic medical record. The electronic medical record is associated with a specific implantable cardiac device and accessible using one or more computing devices 170 (FIG. 2).

The operation 242 is then performed to send billing information derived from the physician note. Once the billing information is determined, a billing report is generated using the billing information. An operation is then performed to send the billing report to a billing system of the medical care facility, or another billing system.

The operation 244 is then performed to performed analytics on the data collected by the interrogation data management system. For example, analytics could be used to identify high risk populations. Physicians could then be alerted to the high risk patients to ensure that proper care is being provided for those patients. Examples of high risk populations may include those with atrial fibrillation and those at risk of stroke. A device manufacturer can obtain this information from the interrogation data management system, for example, to permit manufacturer's representatives to contact the physicians managing those patients.

Figure 4:
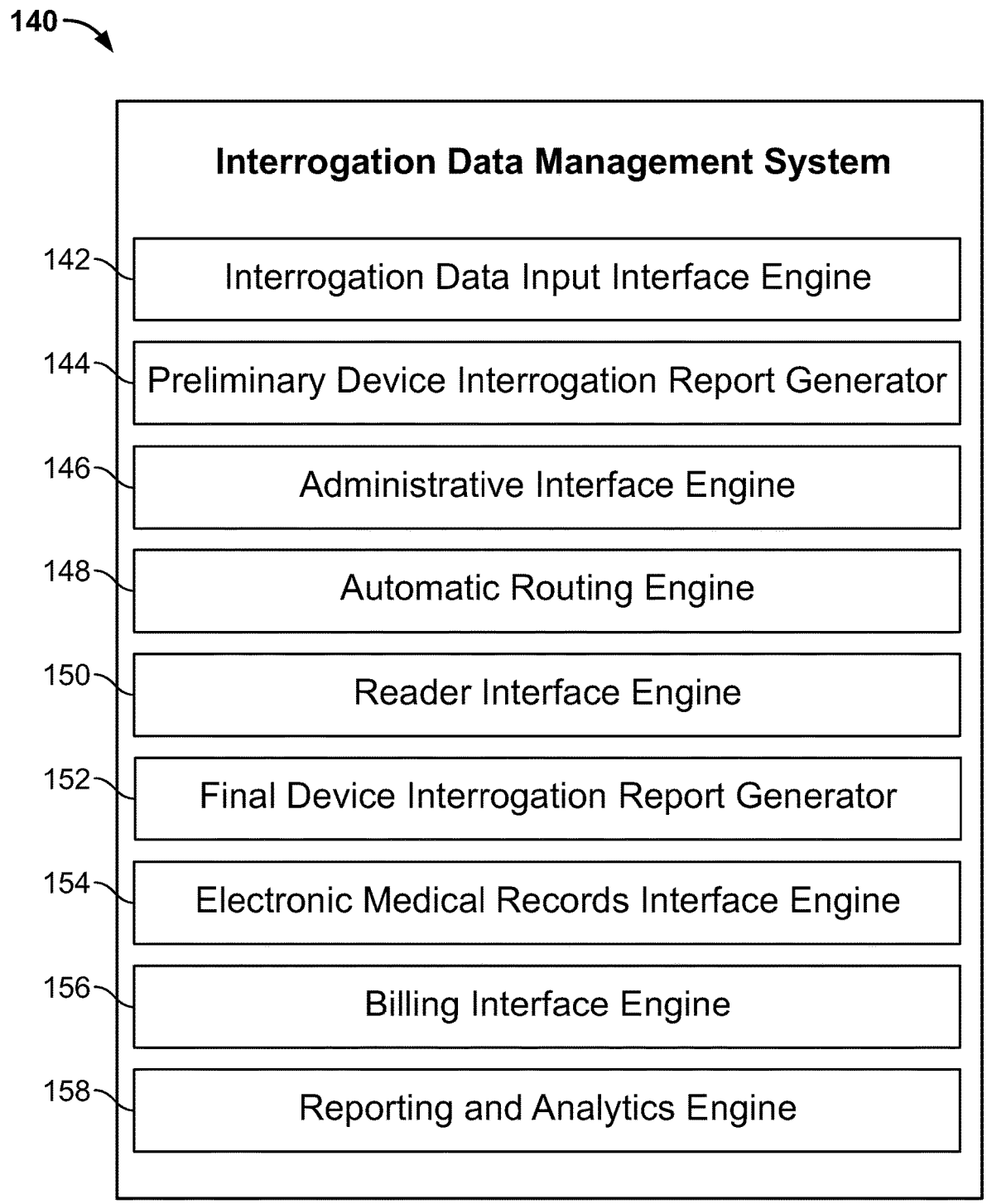
FIG. 4 is a schematic block diagram illustrating an example of the interrogation data management system shown in FIG. 1.

In some embodiments one or more of the operations shown in FIG. 3 can be performed by one or more of the engines illustrated and described in FIG. 4.

FIG. 4 is a schematic block diagram illustrating an example of the interrogation data management system 140 shown in FIG. 1. In this example, the interrogation data management system 140 includes an interrogation data input interface engine 142, a preliminary device interrogation report generator 144, an administrative interface engine 146, an automatic routing engine 148, a reader interface engine 150, a final device interrogation report generator 152, an electronic medical records interface engine 154, a billing interface engine 156, and a reporting and/or analytics engine 158.

The interrogation data input interface operates to receive interrogation data from the implantable cardiac device, such as from a manufacturer's system.

The preliminary device interrogation report generator operates to generate a preliminary device interrogation report. An example of the preliminary device interrogation report is shown in FIGS. 6-7. Additionally, some embodiments include a pre-populated physician note, such as generated by the reader interface engine and final device interrogation report generator described herein.

The administrative interface engine operates to interact with an administrator at a medical care facility. An example of the administrative interface engine is illustrated and described in more detail with reference to FIGS. 8-9.

The automatic routing engine operates to apply a set of routing rules to automatically route interrogation data reports to reading physicians. Examples of the automatic routing engine are illustrated and described in further detail with reference to FIGS. 10-14.

The reader interface engine operates to interact with medical care professionals to formally review the interrogation data reports. Examples of the reader interface engine are illustrated and described in further detail with reference to FIGS. 15-26.

The final device interrogation report generator operates to generate the final device interrogation report. An example of the final device interrogation report is illustrated and described in further detail with reference to FIGS. 28-31.

The electronic medical records interface engine operates to transfer the final device interrogation report to an electronic medical records system. In some embodiments the report is stored in the patient's medical record and becomes a formal part of the medical record.

The billing interface engine 156 operates to capture and define proper billing information, and to generate and transfer a billing report based on the billing information to a billing system of the medical care facility. An example of the billing interface engine 156 is illustrated and described in further detail with reference to FIG. 32.

The reporting and/or analytics engine operates to run searches and perform analytical processing on data generated by the interrogation data management system. Examples of a reporting engine are illustrated and described in further detail with reference to FIGS. 33-48.

Figure 5:
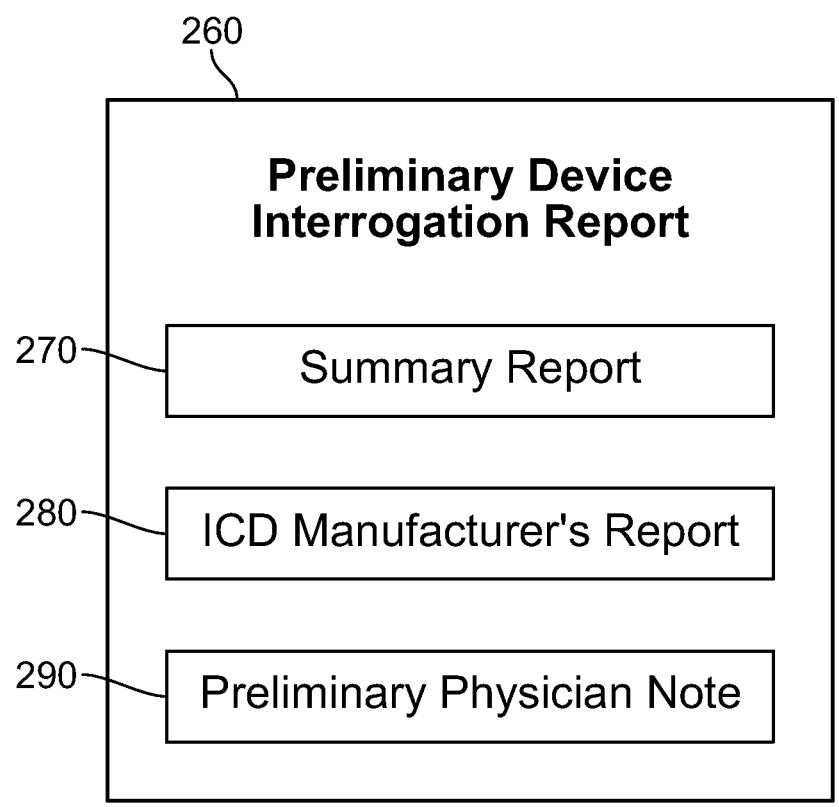
FIG. 5 is a block diagram illustrating an example of a preliminary device interrogation report.

FIG. 5 is a block diagram illustrating an example of a preliminary device interrogation report 260. In this example, the preliminary device interrogation report 260 includes a summary report 270, an implantable cardiac device manufacturer's report 280, and a preliminary physician note 290. An example of a preliminary physician note 290 is illustrated in FIG. 19. The preliminary physician note 290 is sometimes referred to as a preliminary reading physician note. In some embodiments, certain fields of the preliminary physician note 290 are automatically populated from the summary report, by reading information from certain fields of the summary report 270, and making corresponding selections or inserting corresponding descriptions into the fields in the preliminary physician note 290.

In some embodiments the preliminary device interrogation report 260 is sent to and stored in the electronic medical record in a preliminary state where it can be viewed by medical professionals MP that have access to the patient's medical record.

FIGS. 6-7 illustrate another example of the preliminary device interrogation report 260 shown in FIG. 5.

Figure 6A:
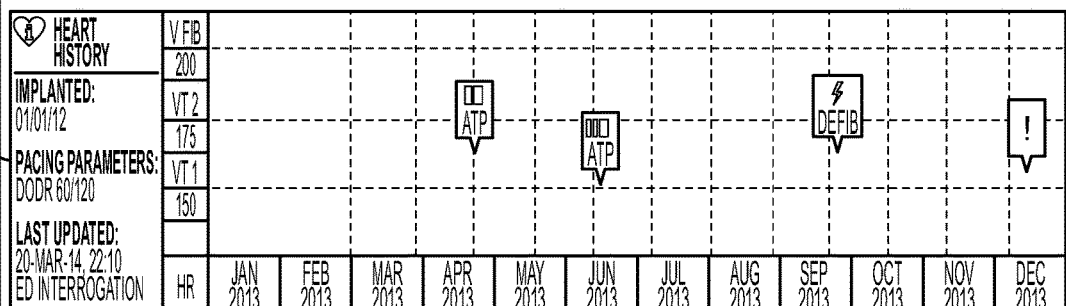
FIG. 6 (including FIGS. 6A to 6D) illustrate an example of a summary report.
Figure 6D:
Figure 7A:
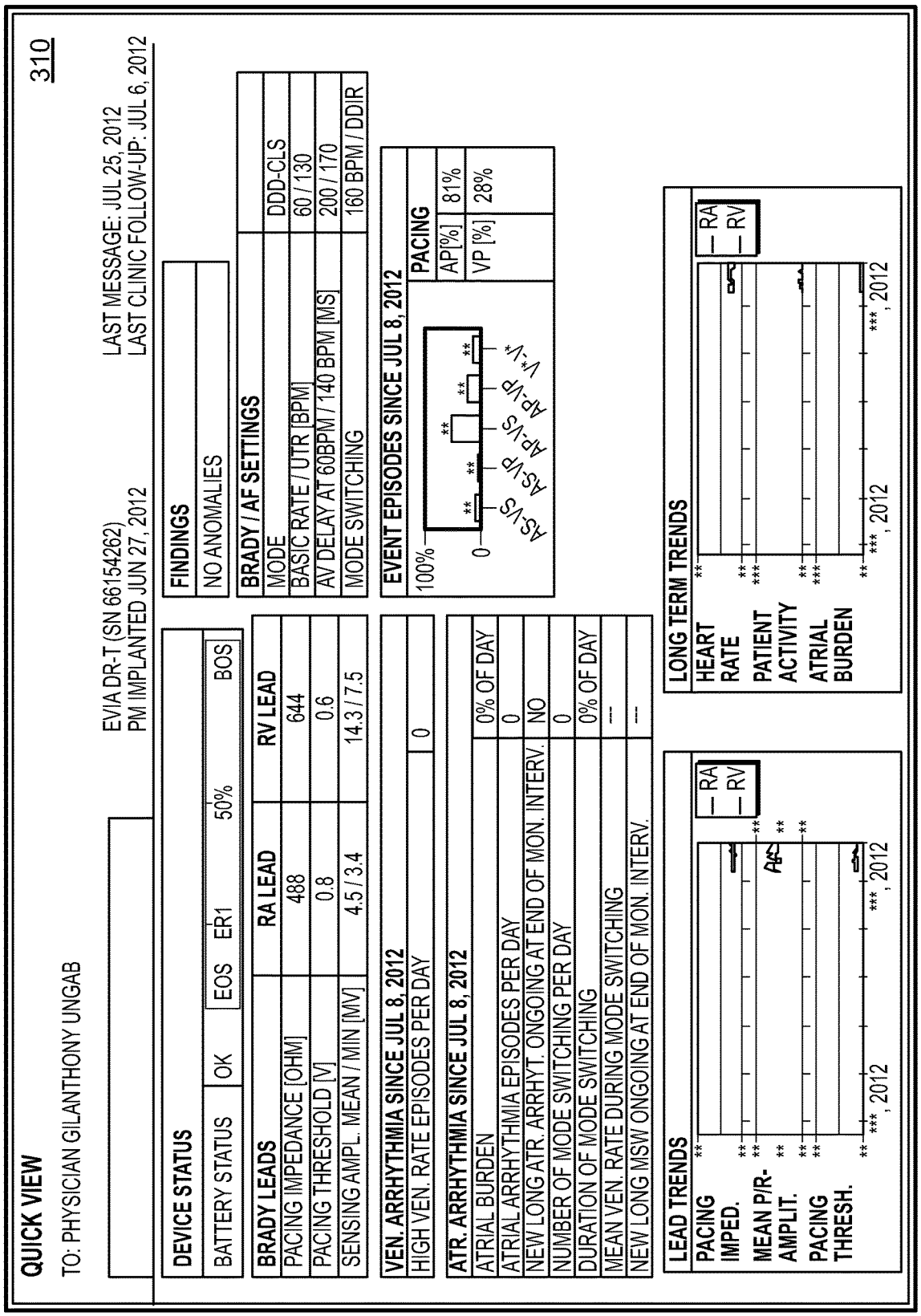
FIG. 7 (including FIGS. 7A to 7F) illustrates an example of a manufacturer's report.
Figure 7C:
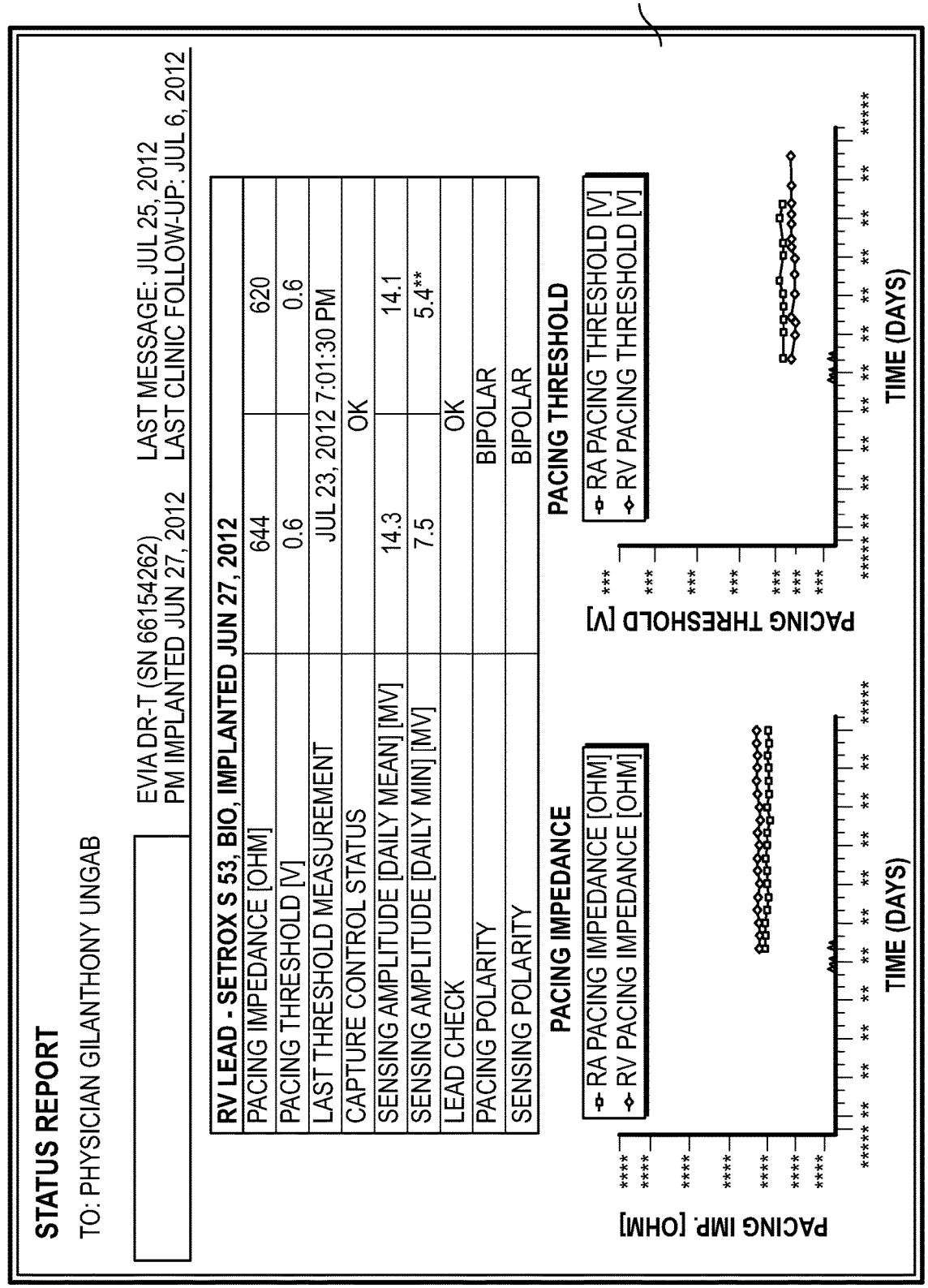
Figure 7C:
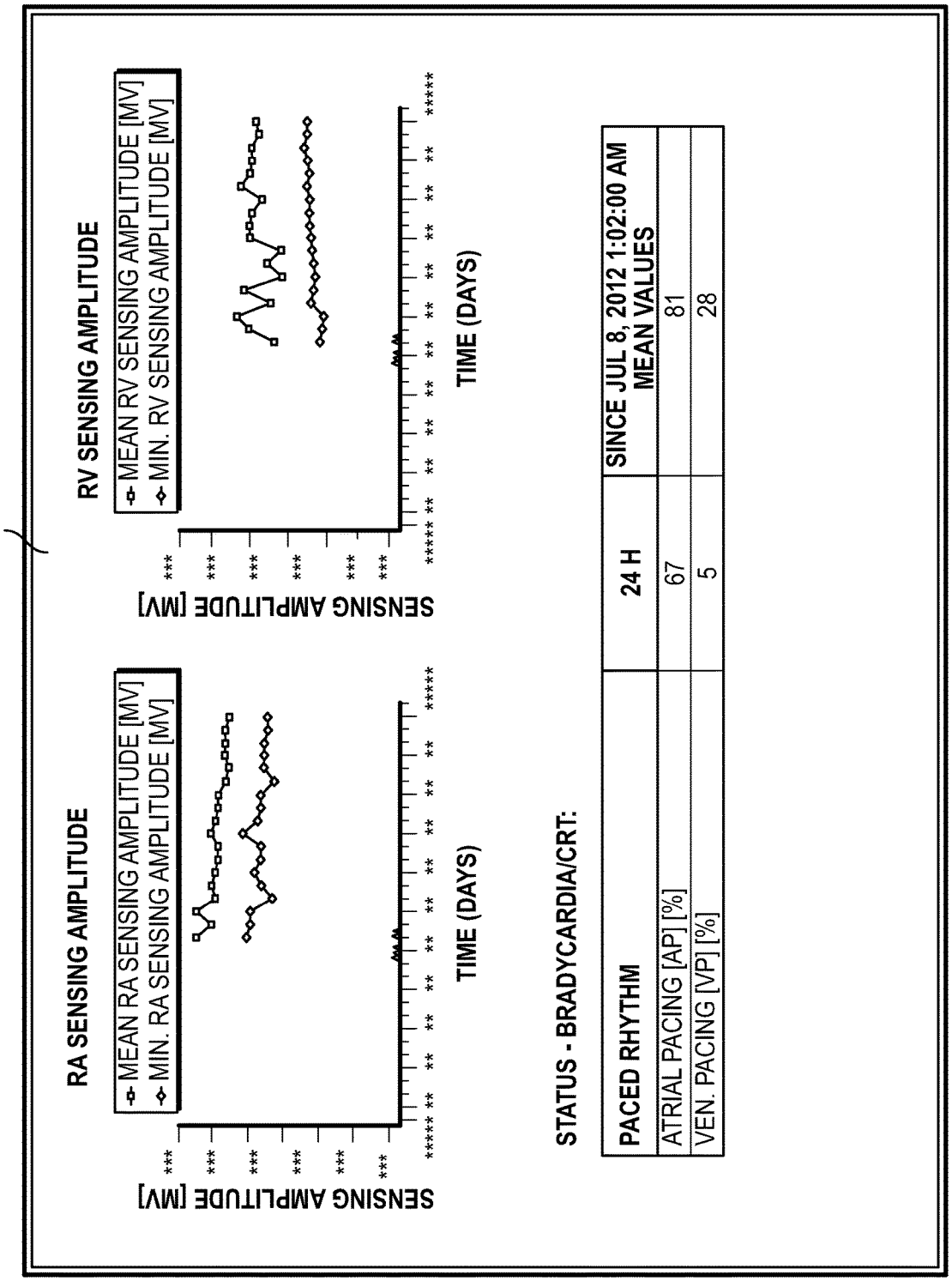
Figure 7D:
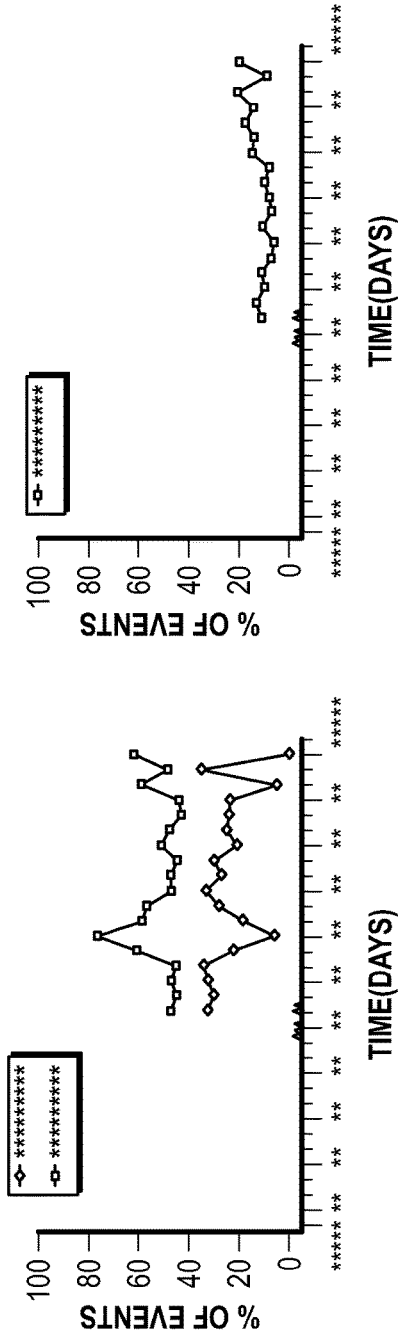
Figure 7E:
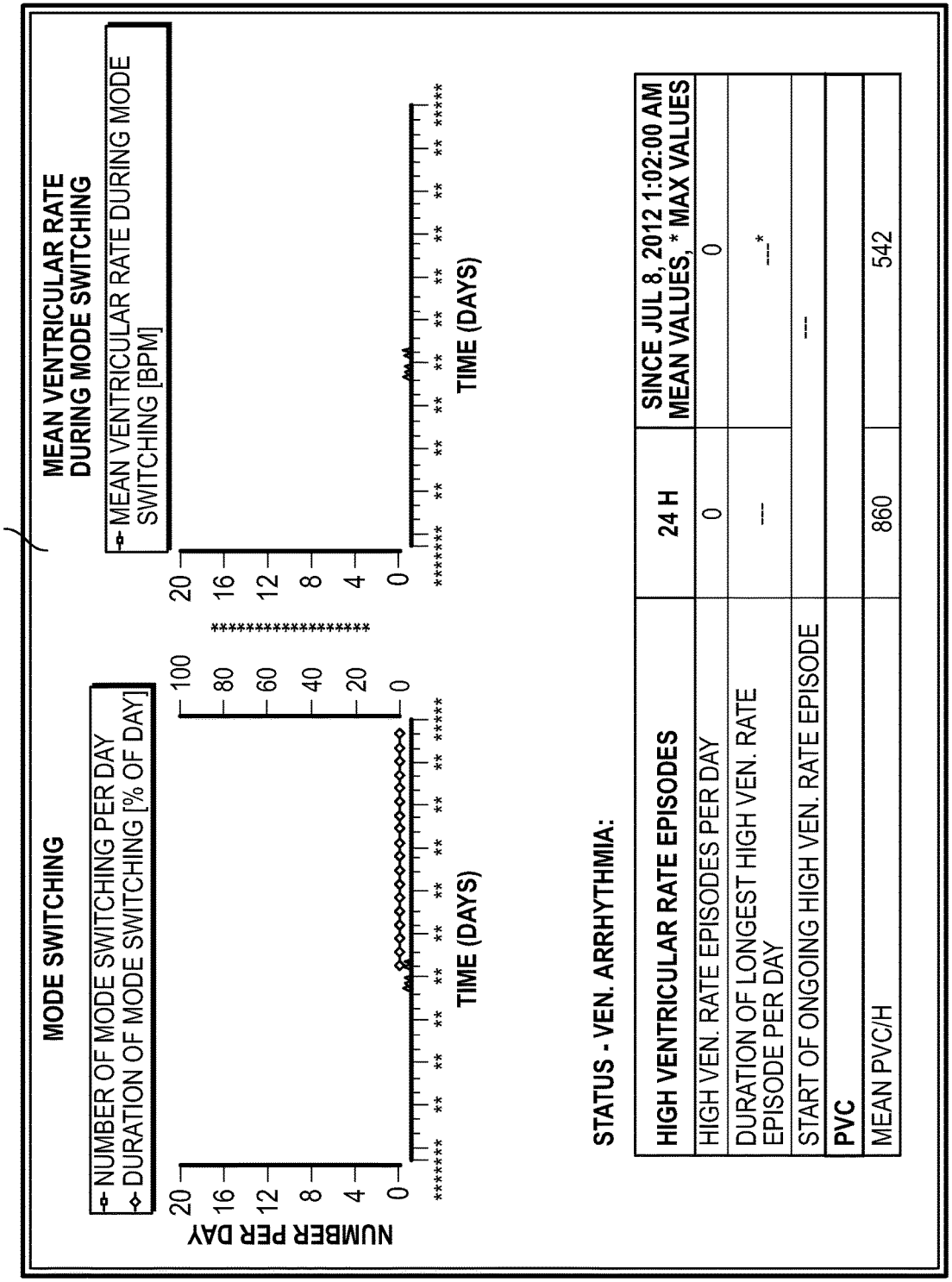
Figure 7F:
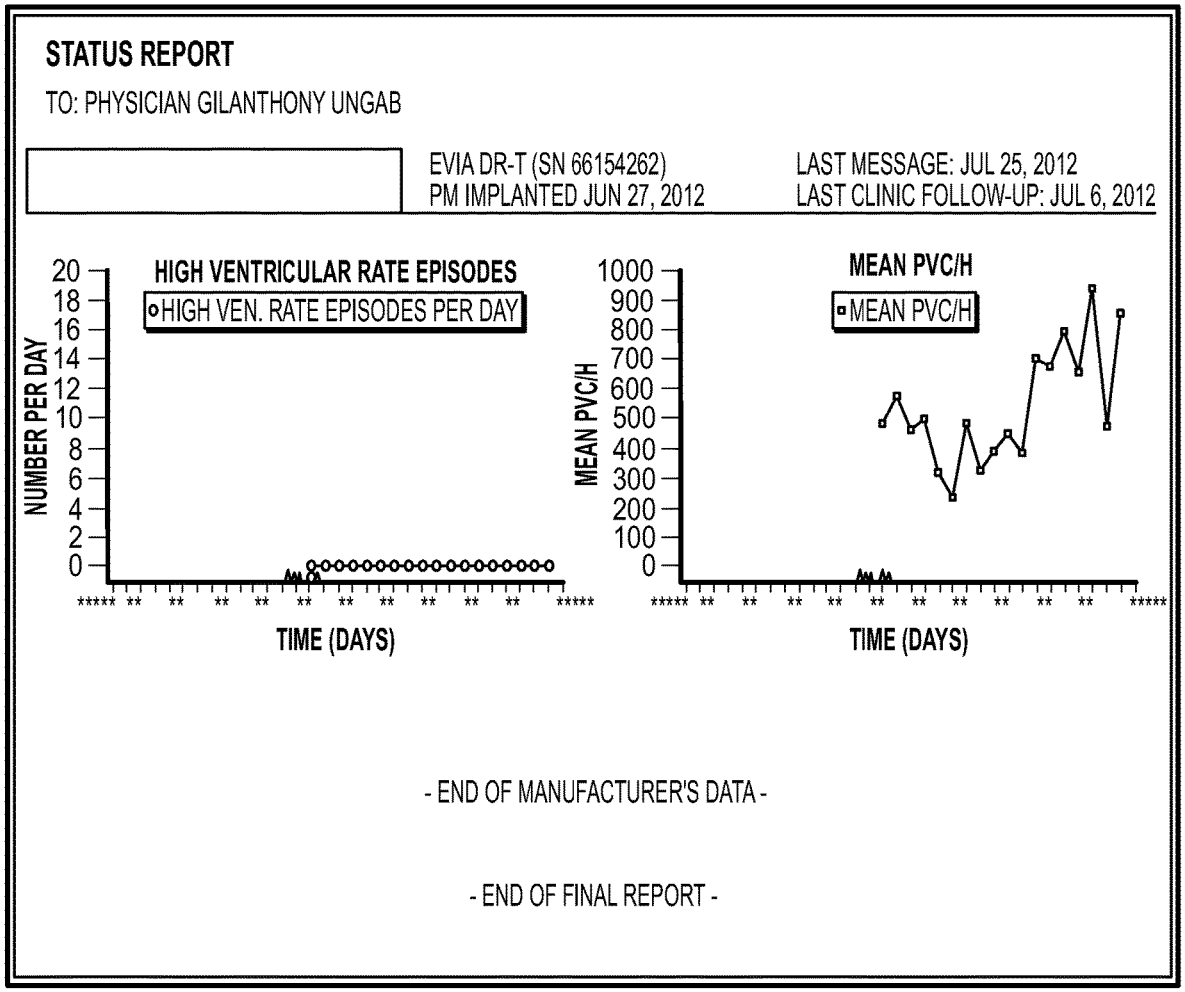

FIG. 6 (including FIGS. 6A to 6D) illustrate an example of a summary report 270. In this example, the summary report 270 includes a summary report display 272, a timeline display 274, and a details display 276.

In this example, the summary report display 272 provides a graphical display of key device information. For example, the summary report display 272 presents information in multiple different categories. In some embodiments the categories include device details 272A, battery status 272B, lead status 272C, arrhythmia log 272D, ventricular tachycardia (VT) therapies 272E, magnet mode 272F, and MRI safety 274E. Some embodiments further include congestive heart failure watch category. In this example, the summary report display 272 graphically displays a tab for each category. In some embodiments the tab is color coded to identify a status of that category of information, such as green for normal, yellow for abnormal, and red for critically abnormal. In some embodiments a size of the tab is enlarged for abnormal or critically abnormal statuses to further draw the medical professional's attention to that information. Within each tab is a brief description of the status, such as having a range from 1 to 10 words, or 1 to 5 words. Additional details and examples of the summary report display 272 are illustrated and described in further detail with reference to Applicant's co-pending U.S. Publication No. 2013/0317852.

Some embodiments include a timeline display 274 that graphically illustrates the dates one which recorded events of the implantable cardiac device occurred.

Some embodiments further include a details display 276. In this example, a detailed listing of interrogation data is displayed for each category of information shown in the summary report display.

FIG. 7 (including FIGS. 7A to 7F) illustrates an example of a manufacturer's report 310.

One example of an implantable cardiac device manufacturer's report is a cardiac rhythm management company report. The report contains a detailed listing of interrogation data obtained from an implantable cardiac device.

Figure 8:
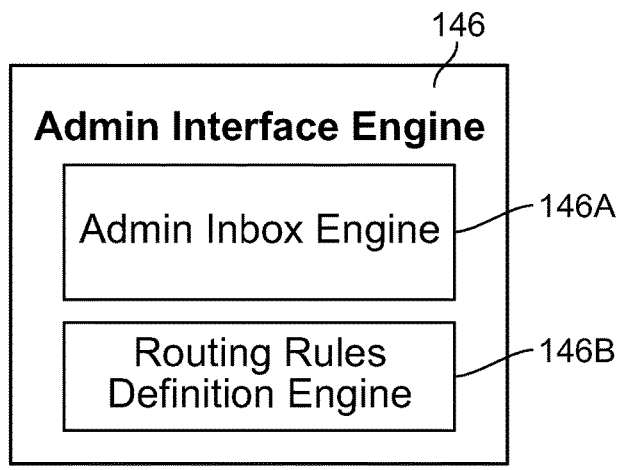
FIG. 8 is a schematic block diagram illustrating an example of an administrative interface engine of the interrogation data management system shown in FIG. 1.

FIGS. 8-9 illustrate an example of the administrative interface engine 146, shown in FIG. 4.

FIG. 8 is a schematic block diagram illustrating an example of an administrative interface engine 146 of the interrogation data management system 140 shown in FIG. 1. In this example, the administrative interface engine 146 includes an administrative inbox engine 146A and a routing rules definition engine 146B.

FIG. 9 is a screen shot illustrating an example of an administrative inbox display 320, such as generated by an administrative inbox engine 146A of the administrative interface engine 146 shown in FIG. 8.

FIGS. 10-14 illustrate examples of the automatic routing engine 148, shown in FIG. 4.

FIG. 10 (including FIGS. 10A and 10B) is a screen shot illustrating an example of routing rules definition display 330, such as generated by a routing rules definition engine 146B of the administrative interface engine 146 shown in FIG. 8.

Figure 11:
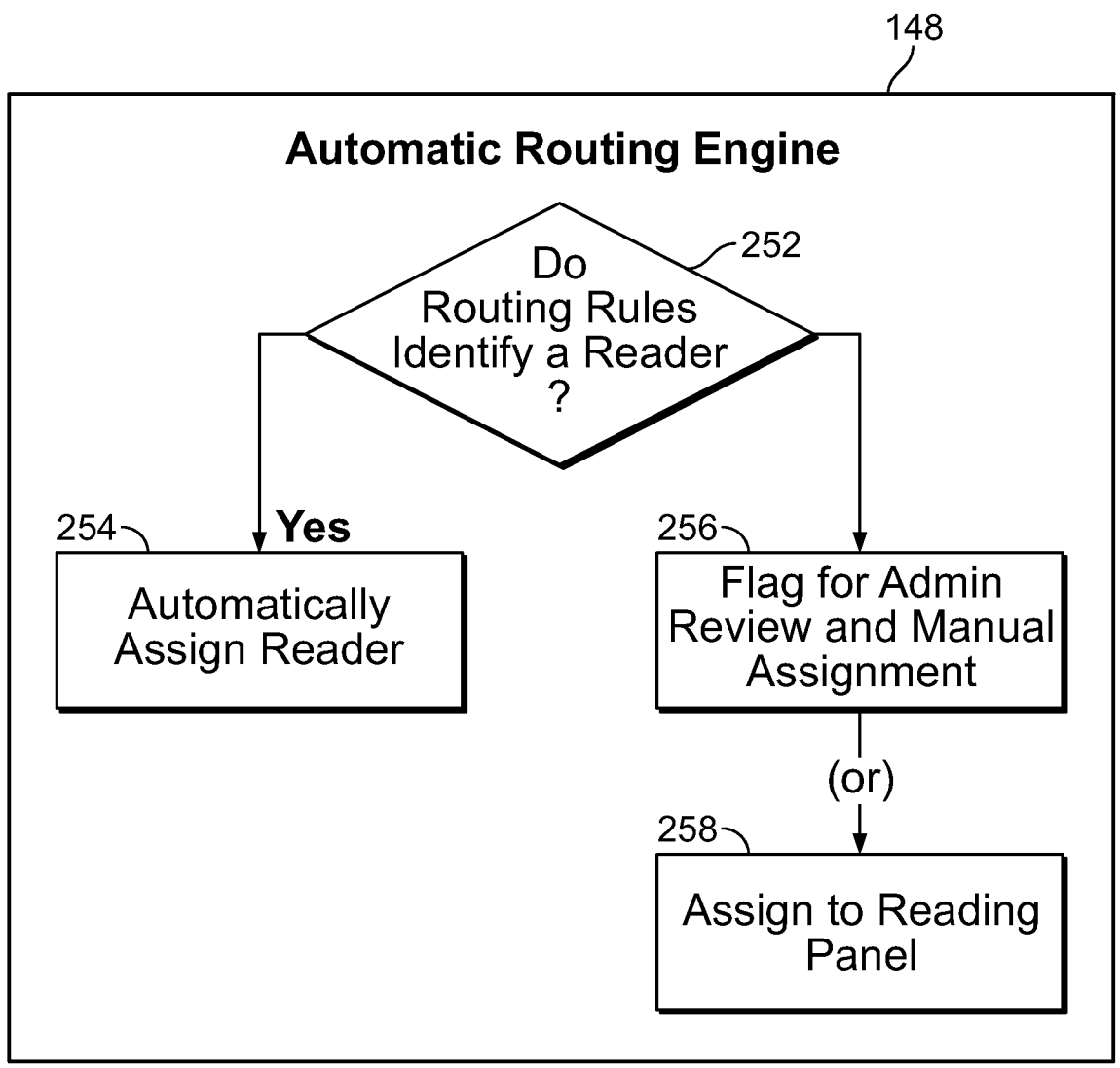
FIG. 11 illustrates an example of an automatic routing engine of the interrogation data management system shown in FIG. 1.

FIG. 11 illustrates an example of an automatic routing engine 148 of the interrogation data management system 140 shown in FIG. 4. The automatic routing engine 148 performs several operations.

In this example, the operations include 252, 254, 256, and 258. Specifically, operation 252 includes determining whether routing rules identify a reader. Where the routing rules identifies the reader, method 250 advances to operation 254, and automatically assigns the reader. In a case where the routing rules do not identify the reader, method 250 advances to operation 256, flagging for administrative review and manual assignment. Alternatively, where the routing rules do not identify the reader, method 250 advances to operation 258 where a reading panel is automatically assigned.

Figure 12:
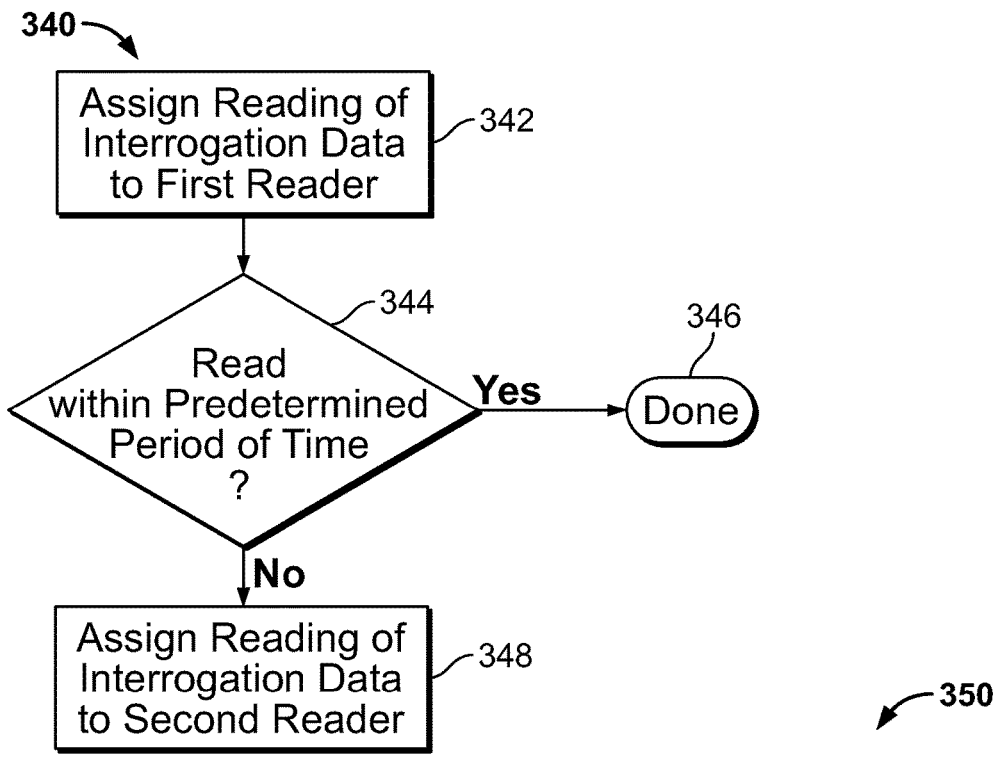
FIG. 12 is a flow chart illustrating an example method of assigning interrogation data to a reading physician.

FIG. 12 is a flow chart 340 illustrating an example method of assigning interrogation data to a reading physician, as indicated at operation 236 of FIG. 3. In this example, the method 340 includes several operations 342, 344, 346, and 348. The operation 342 is performed to assign reading of the interrogation data to a first reader. The operation 344 is then performed to determine whether the interrogation data is read within a predetermined period of time (such as 12, 24, or 48 hours). If not, the operation 348 is performed to assign reading of the interrogation data to a second reader.

Figure 13:
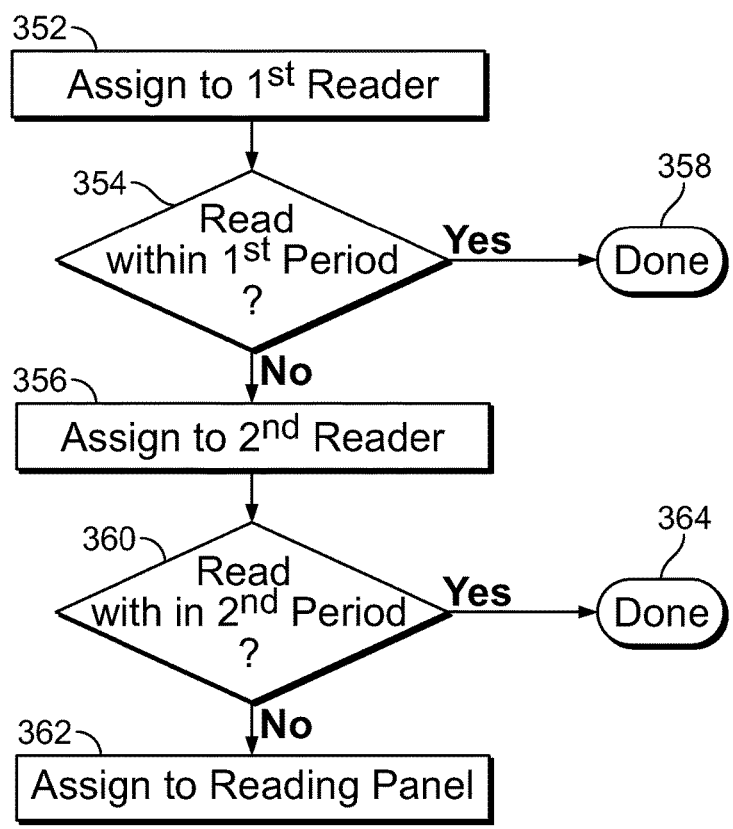
FIG. 13 is a flow chart illustrating another example method of assigning interrogation data to a reading physician.

FIG. 13 is a flow chart 350 illustrating another example method of assigning interrogation data to a reading physician, as indicated at operation 236 of FIG. 3. In this example, the method 350 includes several operations 352, 354, 356, 358, 360, 362, and 364. The operation 352 is performed to assign reading of the interrogation data to a first reader. The operation 354 is then performed to determine whether the interrogation data is read within a predetermined period of time. If not, the operation 356 is performed to assign the interrogation data to a second reader. The operation 360 is then performed to determine whether the interrogation data is read within a second period of time (e.g., 12, 24, or 48 hours from the assignment to the second reader, or a period of time calculated from the initial receipt of the interrogation data or assignment to the first reader). If not, the operation 362 is performed to assign the interrogation data to a reading panel.

In some embodiments the reading panel includes one or more medical professionals MP that are designated to perform the reading of interrogation data for a medical care facility 106 when one or more assigned medical professionals MP do not complete the reading within designated time periods.

Figure 14:
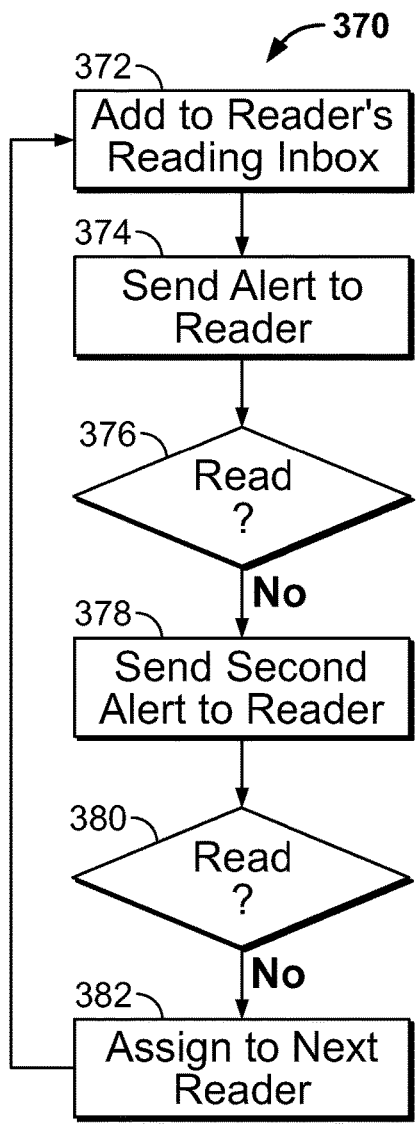
FIG. 14 is a flow chart illustrating another example method of assigning interrogation data to a reading physician, and further illustrating an alerting function.

FIG. 14 is a flow chart 370 illustrating another example method of assigning interrogation data to a reading physician, as indicated at operation 236 of FIG. 3, and further illustrating an alerting function. In this example, the method 370 includes several operations 372, 374, 376, 378, 380, 382, and 384.

The operation 372 is performed to add an assignment to read interrogation data to a reader's reading inbox. The operation 374 is performed to send an alert to the assigned reader, such as by sending an e-mail message to an e-mail address associated with the assigned reader. In some embodiments the assignment and the alert identify a deadline for reading the interrogation data. The operation 376 is then performed to monitor whether or not the reader completes the reading of the assigned interrogation data. If the reading does not occur by predetermined time before a deadline, the operation 378 is performed to send a second alert to the assigned reader. The operation 380 is then performed to continue to monitor whether or not the reader completes the reading of the assigned interrogation data. If the reading does not occur by the deadline, the operation 382 is performed to assign the reading to a next reader. The process can be repeated as many times as desired. In some embodiments the process ends when the interrogation data is assigned to a reading panel or when the assigned reader completes the reading of the assigned interrogation data.

FIGS. 15-27 illustrate examples of the reader interface engine 150, shown in FIG. 4.

Figure 15:
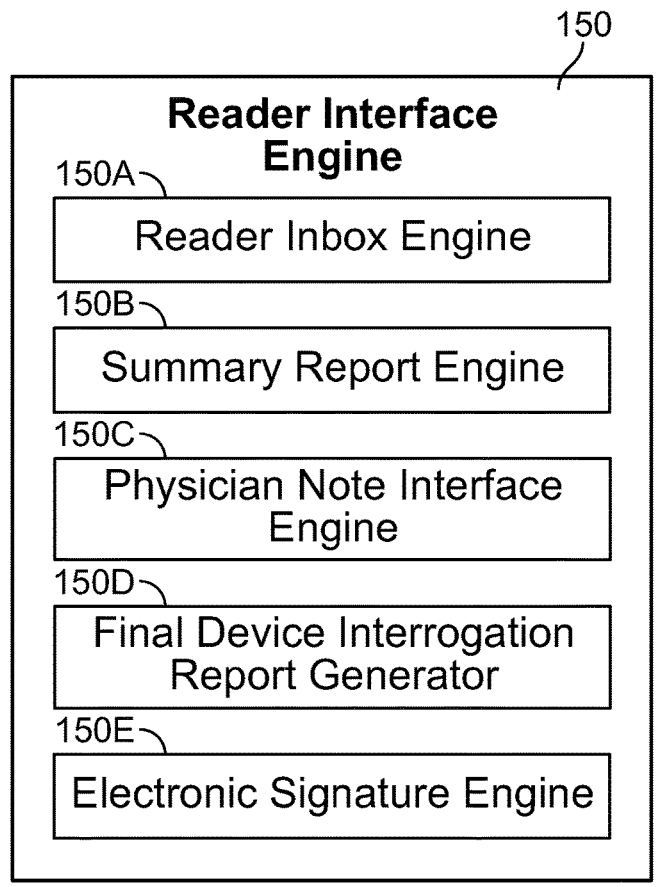
FIG. 15 is a schematic block diagram illustrating an example of the reader interface engine, shown in FIG. 4.

FIG. 15 is a schematic block diagram illustrating an example of the reader interface engine 150, shown in FIG. 4. In this example, the reader interface engine 150 includes a reader inbox engine 150A, a summary report engine 150B, a physician note interface engine 150C, a final device interrogation report generator 150D, and an electronic signature engine 150E.

Some examples of summary reports are illustrated and described in further detail in Applicant's co-pending patent application, U.S. Publication No. 2013/0317852. For example, FIG. 7 of the co-pending patent application describes a home page of a medical device information portal that provides a graphical display of information in a summary report. The summary report can be generated from the interrogation data obtained from a manufacturer's report for example. The summary report is arranged and configured to display the data in a way that is easy to understand by the physician, and to display device data in a common, manufacturer agnostic, format regardless of which manufacturer the interrogation data came from. For example, two reports generated for implantable cardiac devices from different manufacturers include the same format, such that the different data is arranged in the same places within the two reports.

In some embodiments the reader interface engine 150 is provided by a web server, such as the server 108 shown in FIG. 1. Because of this, medical professionals MP can access the reader interface from any location via a computing device 170, such as at a medical care facility 106, at their own clinic, or even at home. Further, a caregiver can be assigned to read interrogation reports from a variety of different medical facilities 106, and all of those assigned interrogation reports appear in the medical professional's reader inbox. This provides a central location for the medical professional MP to obtain the information for all medical facilities 106 that the medical professional works with.

Further, in some embodiments the reader interface presents to the medical professional MP the complete device interrogation report, as discussed herein, which provides the medical professional MP with all device information needed to prepare a complete reading physician note.

FIG. 16 is a screen shot of an example reader inbox display 420, such as generated by a reader inbox engine 150A of the reader interface engine 150 shown in FIG. 15. The reader inbox display illustrates assignments to read interrogation data, and their location. For example, the reader inbox display 420 includes the status 420A of the assignments, the patient name 420B, the location 420C of the patient's primary care, the time remaining 420D for which the interrogation data is to be read, when the interrogation data was assigned 420E, the patient's visit number 420F, where the interrogation data is assigned 420G, and an option to create a report or review report created 420H.

Figure 17:
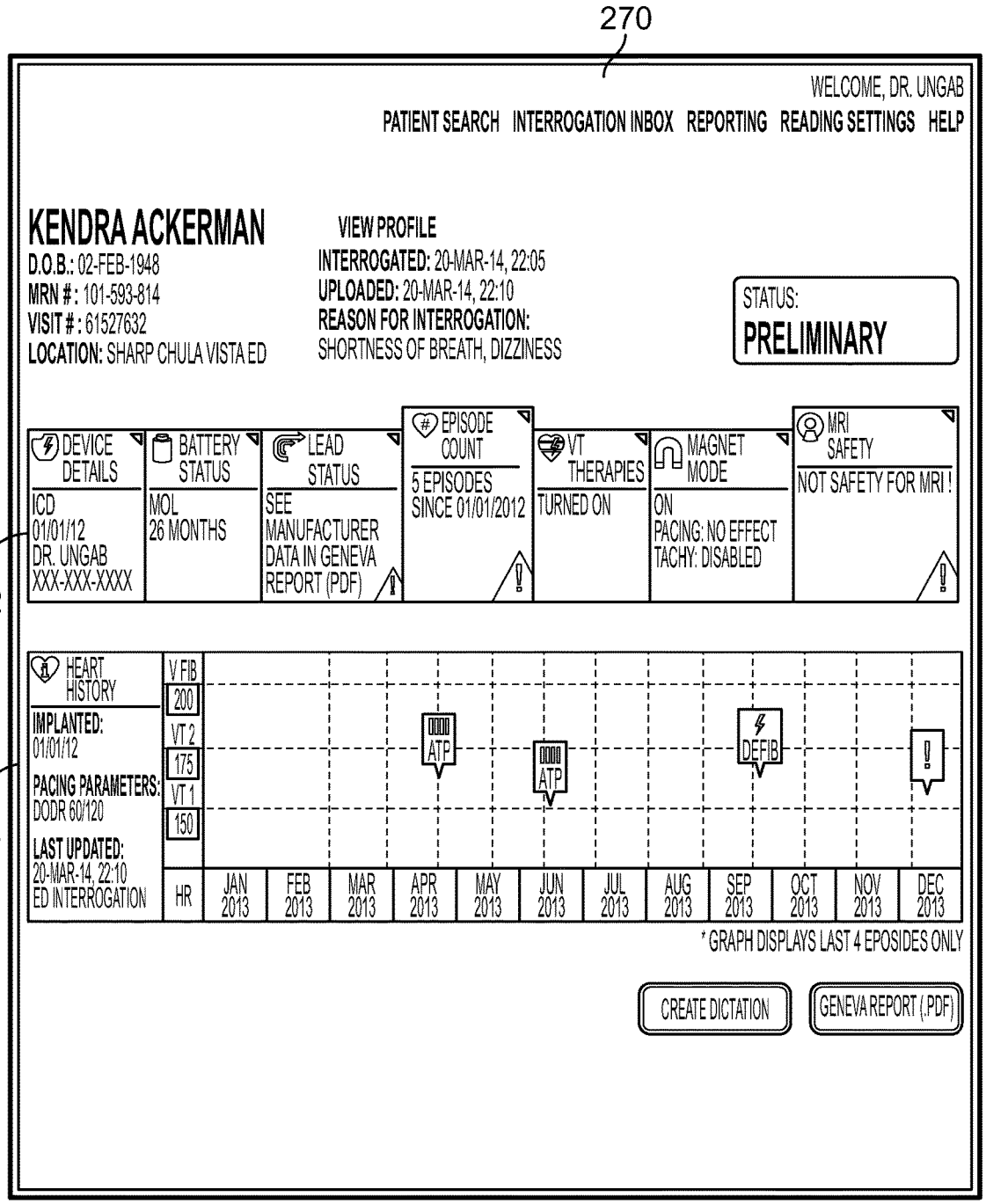
FIG. 17 is a screen shot of an example summary report display, such as generated by a summary report engine, shown in FIG. 15.

FIG. 17 is a screen shot of an example summary report display 270, such as generated by a summary report engine 150B, shown in FIG. 15. The summary report 270 in FIG. 17 includes the summary report display 272 and a timeline display 274. The summary report display 272 includes device details, battery status, lead status, arrhythmia log, ventricular tachycardia (VT) therapies, magnet mode, and MRI safety. The timeline display 274 graphically illustrates the dates one which recorded events of the implantable cardiac device occurred.

FIG. 18 is a screen shot of a details display 276, such as generated by the summary report engine, shown in FIG. 15. In the details display 276 is a detailed listing of interrogation data displayed for each category of information shown in the summary report display 272. In this case, the details display 276 is a listing of interrogation data as it relates to lead status.

FIGS. 19-24 illustrate examples of the physician note interface engine 150C.

FIG. 19 is a screen shot illustrating an example physician note interface display 430, such as generated by the physician note interface engine 150C shown in FIG. 15. The physician note interface engine 150C operates to interact with the reading physician to generate a physician note including the reading physician's findings/interpretations of the interrogation data, as well as the reading physician's conclusions.

In this example, the physician note interface display 430 includes a set of pre-populated fields. Pre-populating fields of the reading physician note saves the reading physician a lot of time by not requiring the reading physician to manually enter information already known by the interrogation data management system 140. The reading physician can then focus on reviewing the information, confirming it is correct, adding or modifying the information as desired, and quickly completing and electronically signing the report. Further, in addition to pre-populated fields, in some embodiments the physician note interface 430 provides a set of selectable options for each of the available categories of information to be documented within the reading physician note. This further saves the physician time and reduces the chance of errors by allowing the physician to quickly select from the selectable options. Examples of selectable options are shown in FIG. 20, for example. Free text fields are also available to permit the reading physician to add additional comments as desired.

Figure 20F:
FIG. 20 (including FIGS. 20A-20G) is a screen shot illustrating another example of the physician note interface display shown in FIG. 20, showing an expanded view.

FIG. 20 (including FIGS. 20A-20G) is a screen shot illustrating another example of the physician note interface display 430 shown in FIG. 20, showing an expanded view. As indicated FIGS. 20A-20G include a set of selectable options for each of the available categories of information to be documented within the reading physician note. For example, FIG. 20A includes selectable options relating to the device details of the implantable cardiac device. In addition, FIG. 20B includes selectable options related to the battery status of the implantable cardiac device. Moreover, FIG. 20C includes selectable options related to the lead status of the implantable cardiac device. Likewise, FIG. 20D includes selectable options related to the episode count of the implantable cardiac device. In addition, FIG. 20E includes selectable options related to the VT therapies of the implantable cardiac device. Moreover, FIG. 20F includes selectable options related to the MRI safety of the implantable cardiac device. Finally, FIG. 20E includes selectable options related to the report conclusion.

FIG. 21 is a screen shot of an example status selection page 450 of the example physician note interface engine 150C shown in FIG. 15. At the status selection page 450, the physician can select a status code associated with the free text entry field information shown in FIG. 21. The status corresponds with a color code to assist someone reviewing the report to know the status of each of the available categories of information. For example, the status code is selected from normal 452, abnormal 454, and critically abnormal 456.

Figure 24:
FIG. 24 is a screen shot illustrating an example of the physician note interface display shown in FIG. 19 after the selection of the billing codes as shown in FIGS. 22 and 23.

FIGS. 22-24 illustrate additional exemplary aspects of the physician note interface displays 430 shown in FIGS. 19-20.

FIG. 22 is a screen shot illustrating an example of the physician note interface display 430 shown in FIG. 19, and further illustrating the selection of one or more billing codes, such as Current Procedural Terminology (CPT) codes 430A.

FIG. 23 is a screen shot illustrating an example of the physician note interface display 430 shown in FIG. 19, and further illustrating the selection of one or more billing codes, such as diagnosis codes 430B.

FIG. 24 is a screen shot illustrating an example of the physician note interface display 430 shown in FIG. 19 after the selection of the billing codes as shown in FIGS. 22 and 23.

Figure 25:
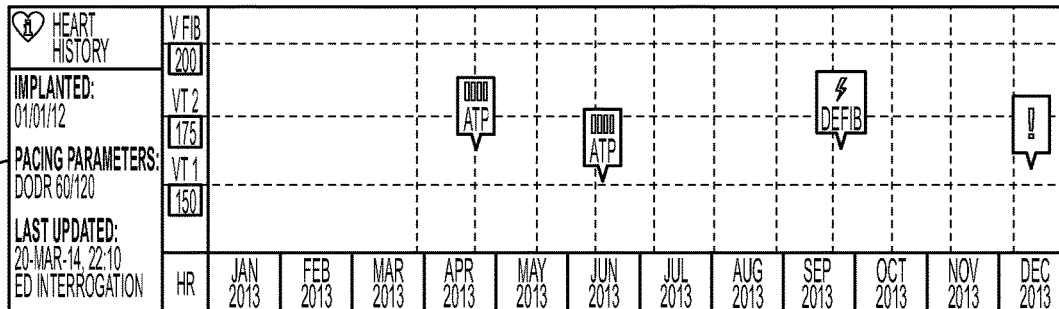
FIG. 25 is a screen shot illustrating another example of the summary report display shown in FIG. 17.

FIG. 25 is a screen shot illustrating another example of the summary report display 272 shown in FIG. 17, as displayed by the reader interface engine 150. The summary report display 270 of FIG. 25 includes a summary report display 272 and a timeline display 274.

FIG. 26 is a screen shot illustrating another example of a physician note interface display 430 after the reading physician's findings/interpretations and conclusion have been entered with a space for the physician's electronic signature 432.

FIG. 27 is a screen shot illustrating the example physician note interface display 430 of FIG. 26, and further illustrating the physician signing via the electronic signature process involving the electronic signature engine 150E shown in FIG. 15.

FIGS. 28-31 illustrate an example of a final device interrogation report 460, such as generated by the final device interrogation report generator 152 shown in FIG. 4.

Figure 28:
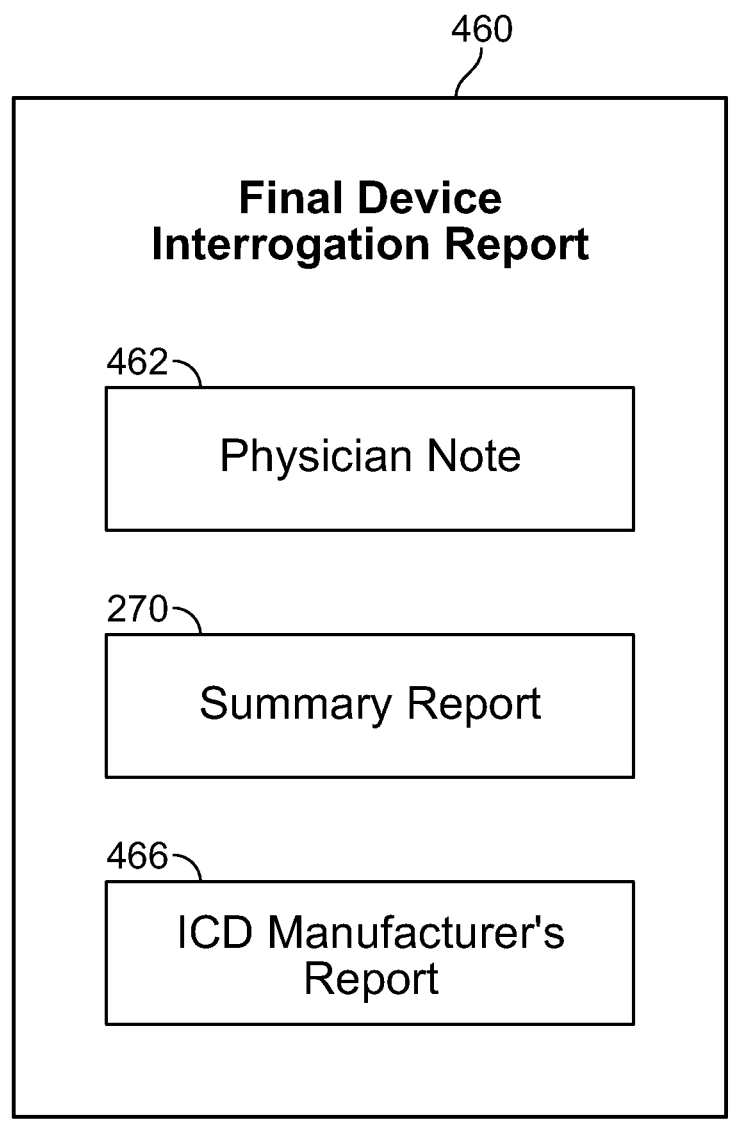
FIG. 28 is a schematic block diagram illustrating an example of a final device interrogation report.
Figure 31A:
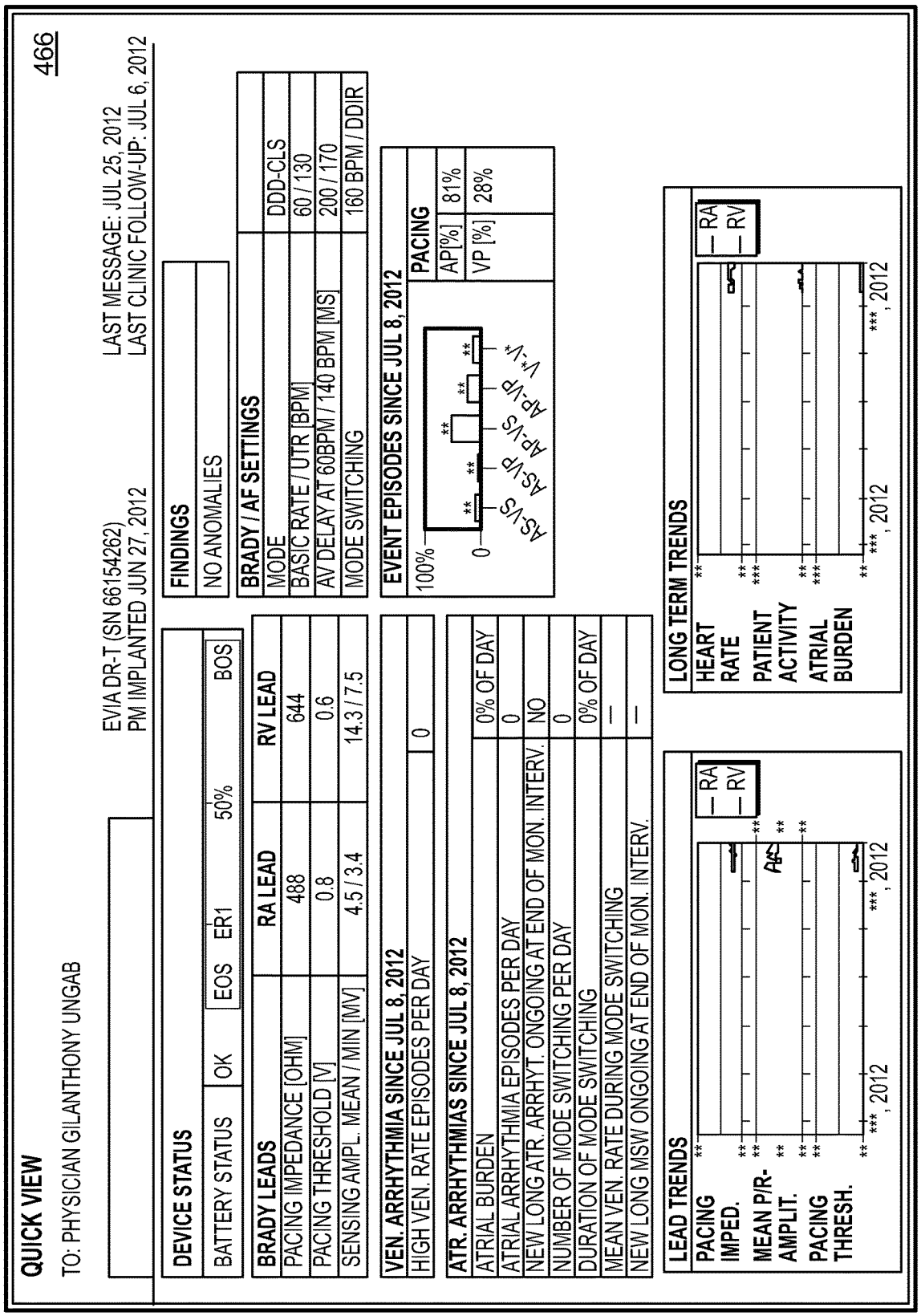
FIG. 31 (including FIGS. 31A-F) illustrates an example ICD manufacturer's report of the final device interrogation report.
Figure 31C:
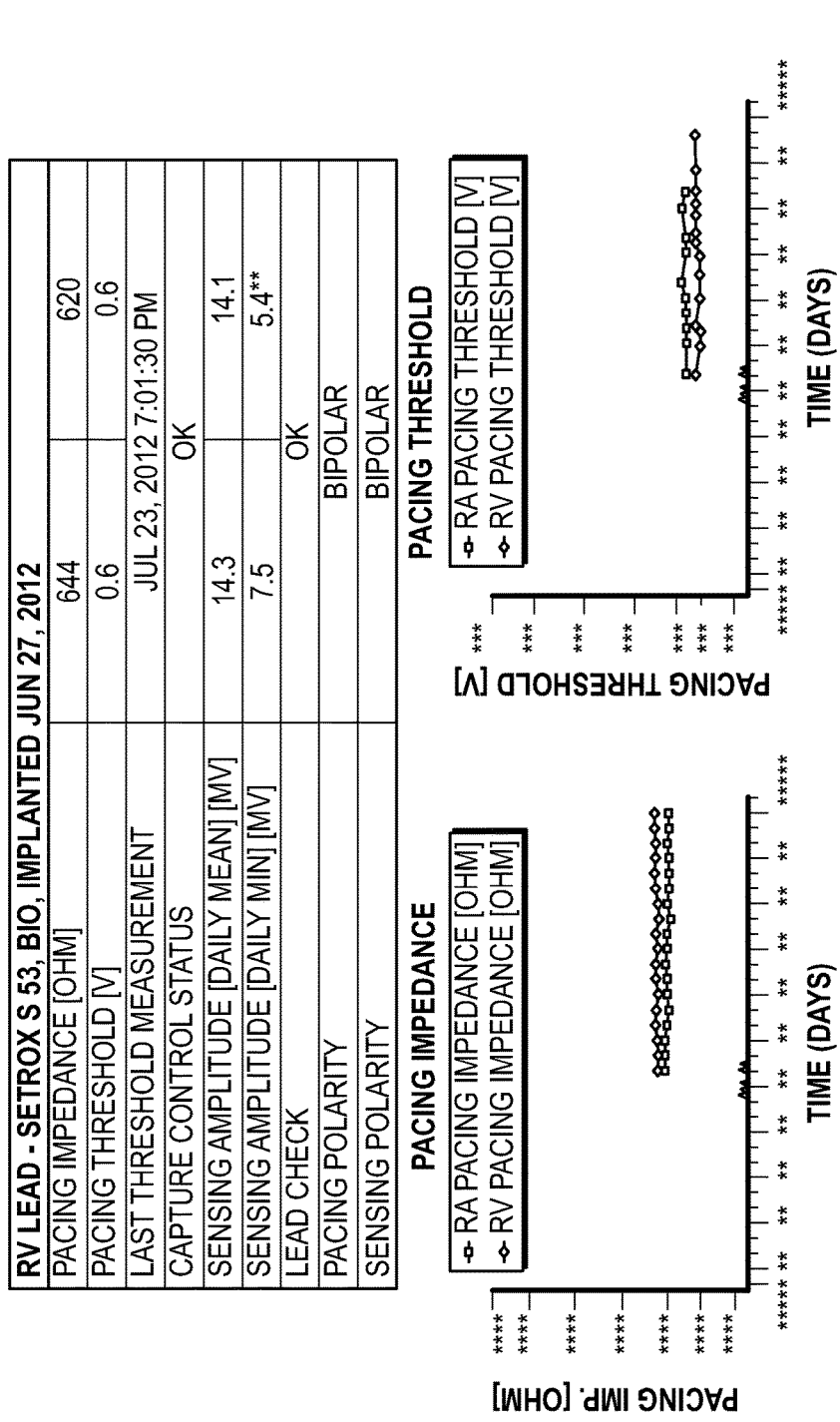
Figure 31C:
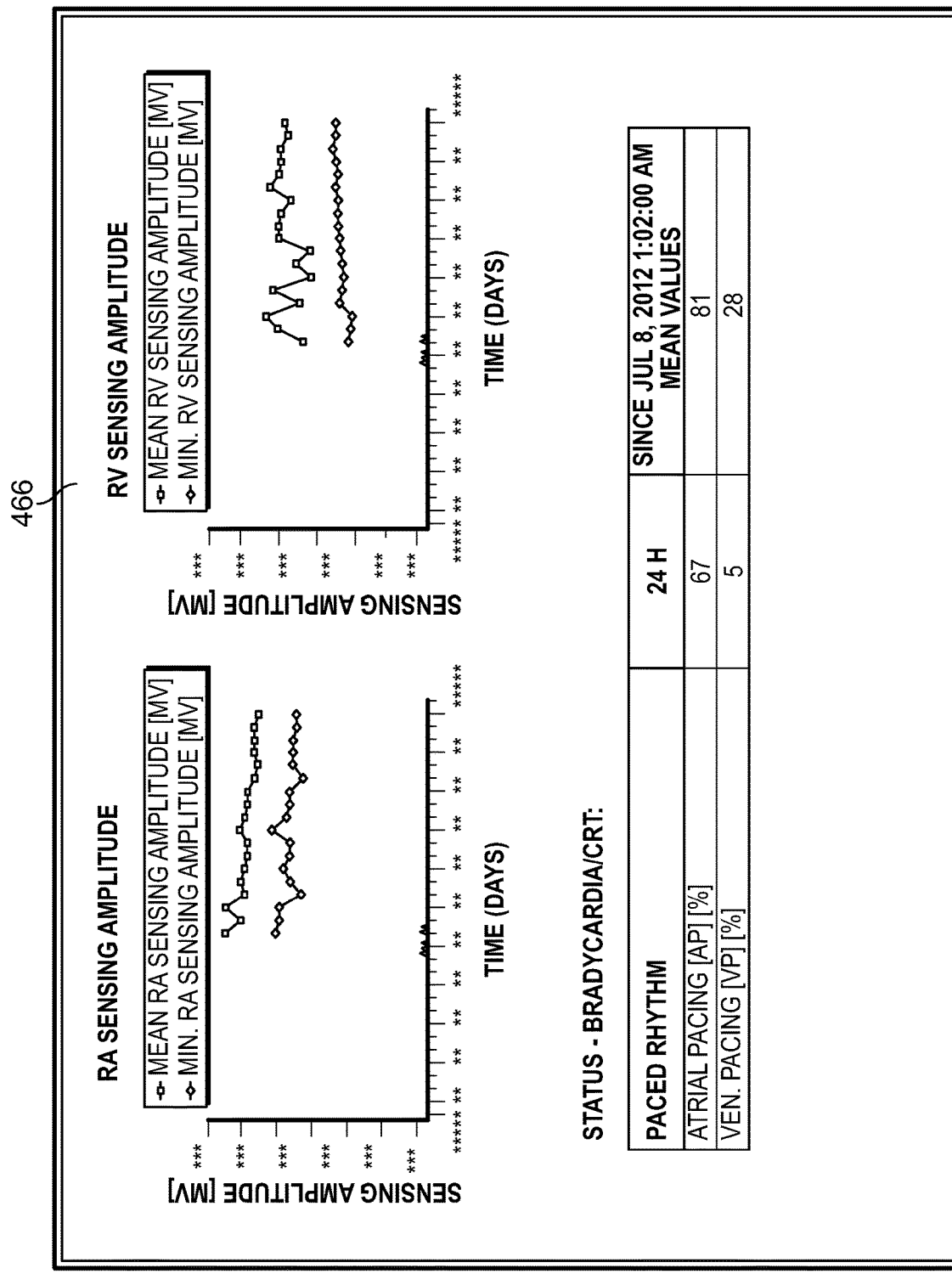
Figure 31D:
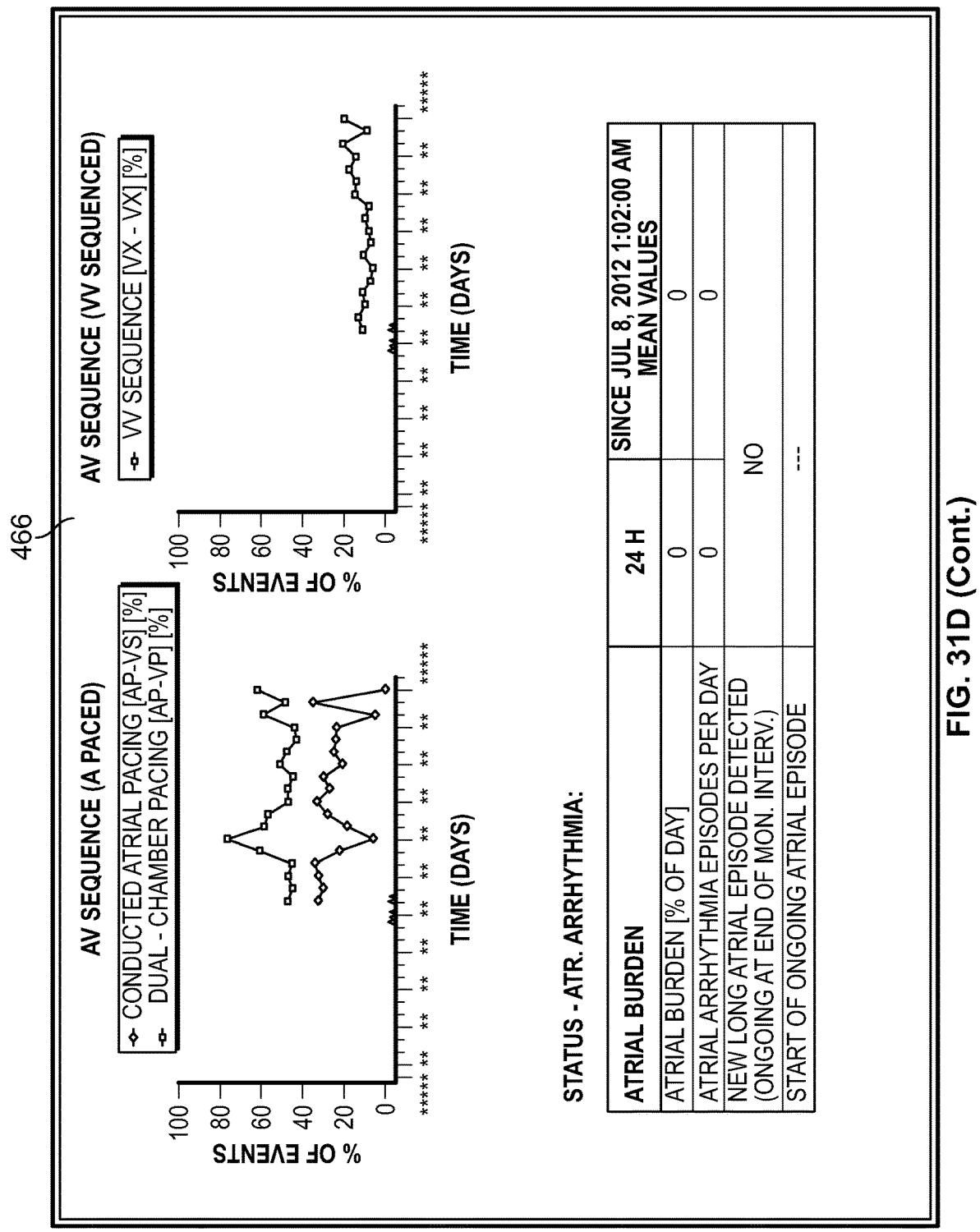
Figure 31E:
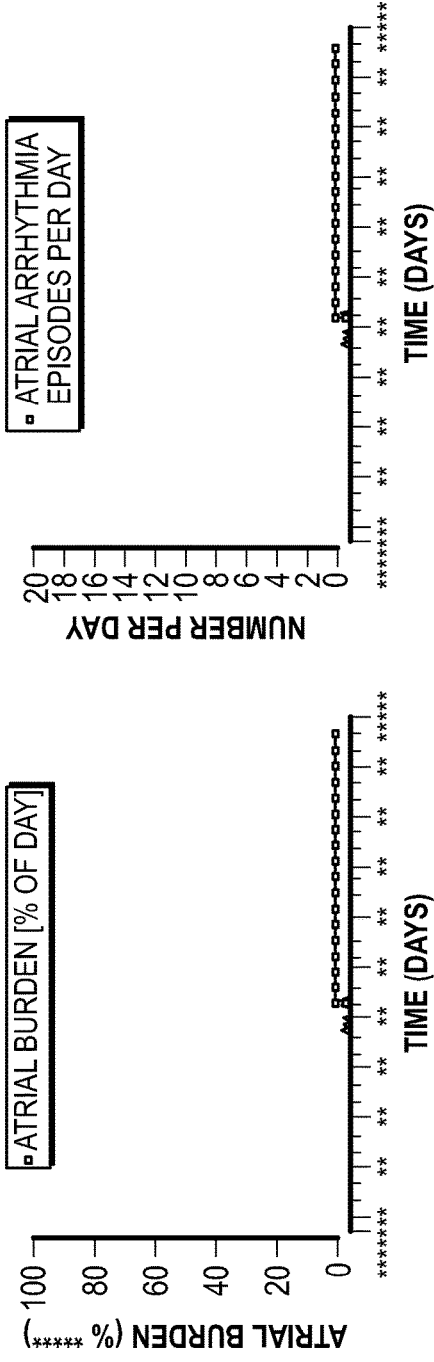
Figure 31E:
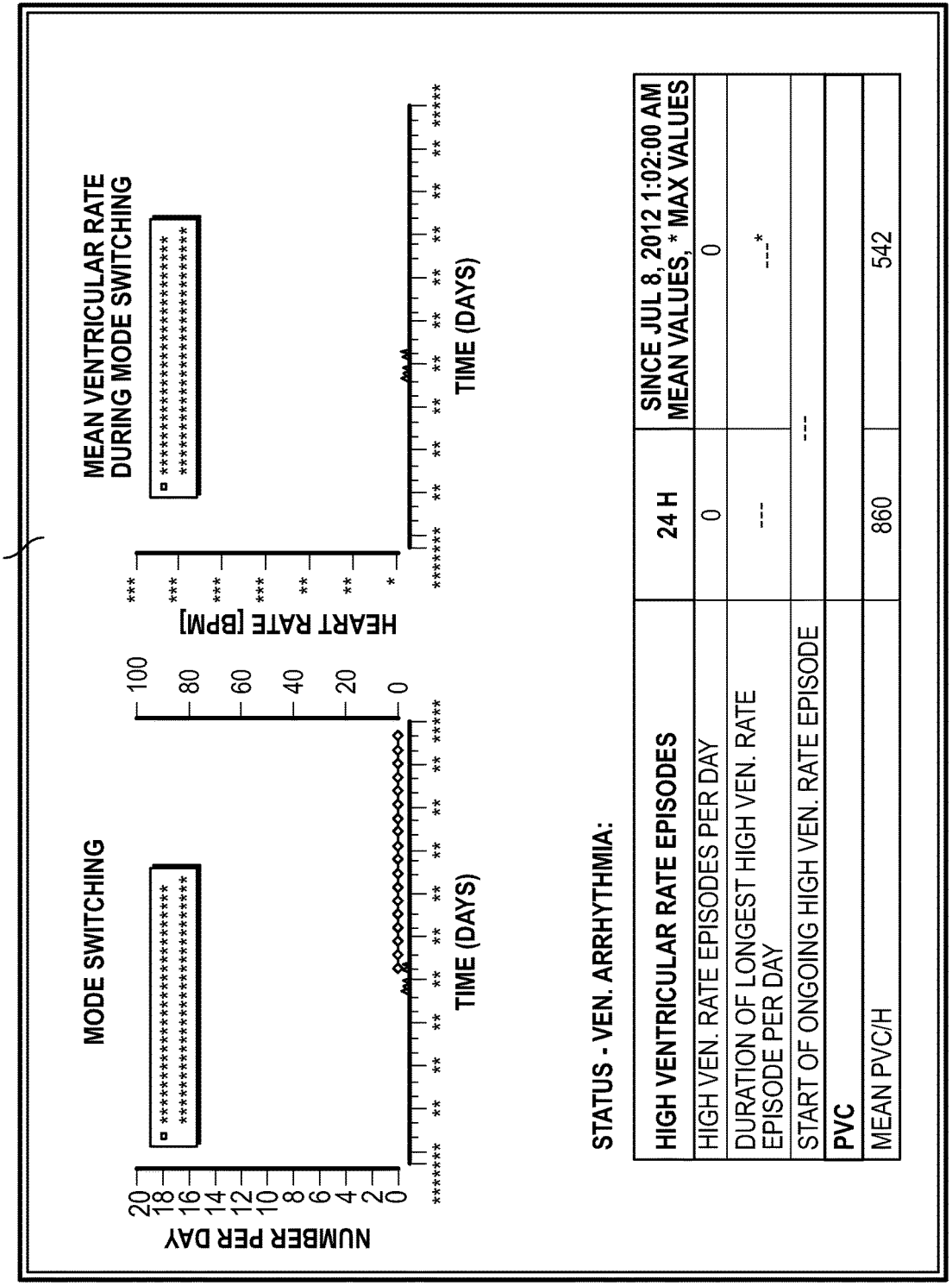
Figure 31F:
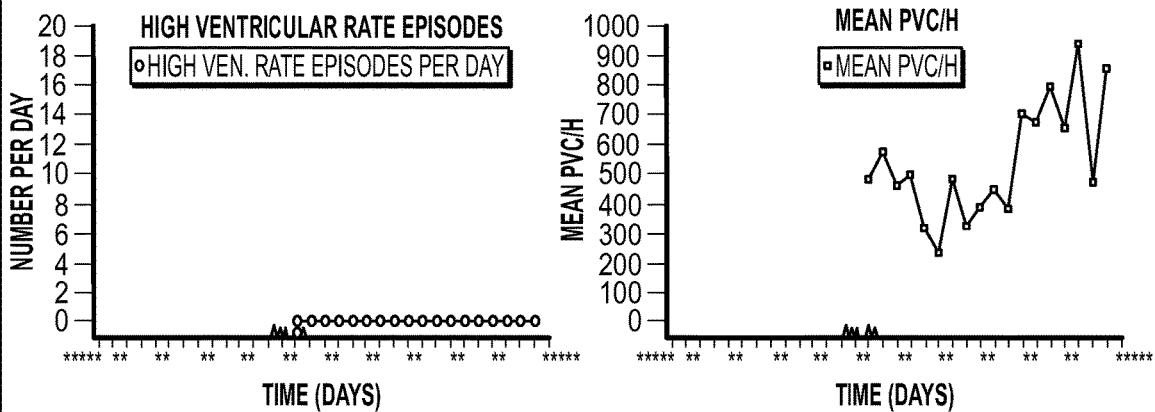

FIG. 28 is a schematic block diagram illustrating an example of a final device interrogation report. In FIG. 28, the final device interrogation report 460 includes a reading physician note 462, a summary report 270, and an implantable cardiac device manufacturer's report 466. The reading physician note 462 can be created using the device data to automatically populate one or more fields. The summary report 270 is created from the implantable cardiac device manufacturer's report. The implantable cardiac device manufacturer's report 466 includes device data associated with the implantable cardiac device.

FIG. 29 illustrates an example physician note 462 of the final device interrogation report. The physician note 462 includes the selected responses for each of the available categories of information.

FIG. 30 (including FIGS. 30A-30C) illustrates an example summary report 270 of the final device interrogation report 460. This includes the summary report display 272, a timeline display 274, and a details display 276.

FIG. 31 (including FIGS. 31A-F) illustrates an example ICD manufacturer's report 466 of the final device interrogation report 460. The ICD manufacturer's report 466 contains the available categories of information found in the physician note 462, as a result of the ICD manufacturer's report 466 being used to generate the physician note 462. The ICD manufacturer's report 466 specifically includes a quick view of the ICD (FIG. 31A). The ICD manufacturer's report 466 also includes an overall status summary (FIG. 31B), a device status (FIG. 31B), and a lead status (FIG. 31B). The ICD manufacturer's report 466 also includes pacing impedance and threshold data (FIG. 31C), sensing amplitude data (FIG. 31C), and the data summary (FIG. 31C). The ICD manufacturer's report 466 also includes paced rhythm and AV sequence data (FIG. 31D). The ICD manufacturer's report 466 also includes atrial burden and episodes data (FIG. 31E), mode switching and mean ventricular rate during mode switching data (FIG. 31E), and the data summary (FIG. 31E). Finally, the ICD manufacturer's report 466 includes high ventricular rate episodes and a mean PVC/H data (FIG. 31F).

Figure 32:
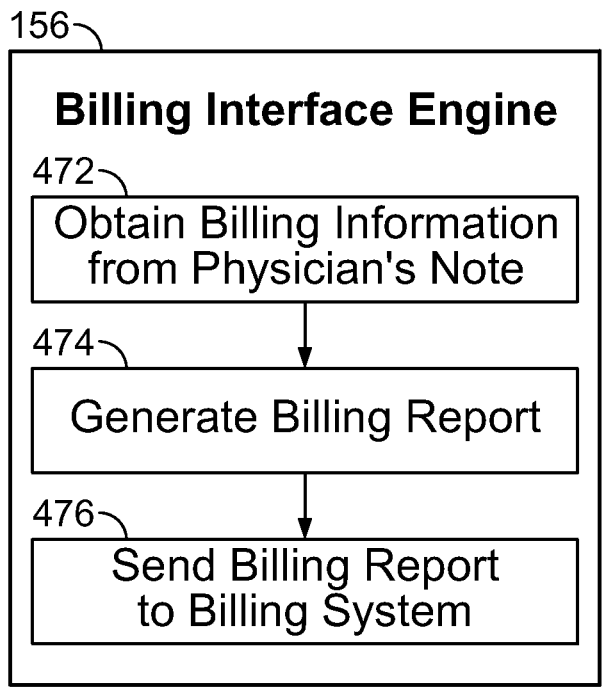
FIG. 32 is a schematic block diagram illustrating an example billing interface engine, such as of the interrogation data management system shown in FIG. 4.

FIG. 32 is a schematic block diagram illustrating an example billing interface engine 156, such as of the interrogation data management system 140 shown in FIG. 4. In this example, the billing interface engine 156 performs several operations. In this example, the billing interface engine 156 performs operations 472, 474, and 476. Specifically, operation 472 is performed to obtain billing information from the physician note 462. Once the billing information is obtained, operation 474 is then performed to generate a billing report using the billing information. Once the billing report is generated, operation 476 is then performed to send the billing report to a billing system of the medical care facility 106, or another billing system.

FIGS. 33-48 illustrate examples of the reporting and analytics engine 158, such as of the interrogation data management system 140 shown in FIG. 4.

Figure 33:
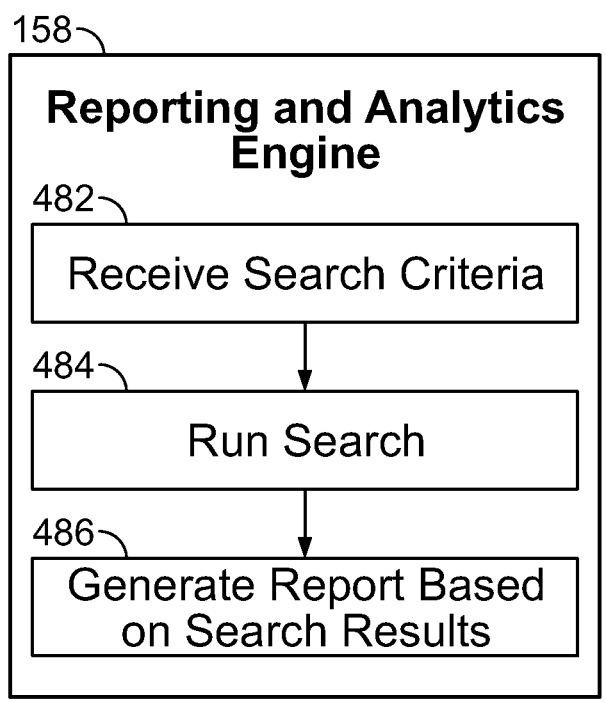
FIG. 33 is a schematic block diagram illustrating an example reporting engine, such as of the interrogation data management system shown in FIG. 4.

FIG. 33 is a schematic block diagram illustrating an example reporting engine 158, such as of the interrogation data management system 140 shown in FIG. 4. In this example, the reporting engine 158 performs several operations. In this example, the reporting engine 158 performs operations 482, 484, and 486.

Specifically, operation 482 is performed to receive search criteria. Examples of a report interface are illustrated and described in further detail with reference to FIGS. 34-47. Once the search criteria are received, operation 484 is then performed to run a search according to the search criteria and generate search results. Once the search results have been generated, operation 486 is then performed to generate a report based on the search results. An example of a report generated by the reporting engine is shown in FIG. 48.

FIG. 34 is a screen shot illustrating an example of a reporting interface display 490. The reporting interface display 490 at FIG. 34 allows for search criteria entry. In this example, the type of report, the time frame for which the report is created, and report format may be customized to search. Once the search criteria are received, a search is ran according to the search criteria.

FIG. 35 is another screen shot of the example reporting interface display 490 shown in FIG. 34. In this example, the selectable options of interrogation statistic and billing have been selected as search criterions.

FIG. 36 is another screen shot of the example reporting interface display 490 shown in FIG. 34. FIG. 36 further illustrates the selection of billing as the report type, and provides a set of selectable options for each of the available filters to be adjusted for the search criteria. Examples of selectable options include location, CPT codes, and diagnosis codes.

FIG. 37 is another screen shot of the example reporting interface display 490 shown in FIG. 34, and further illustrating the selection of one or more filters, such as location of the medical care facility 106.

FIG. 38 is another screen shot of the example reporting interface display 490 shown in FIG. 34, and further illustrating the selection of one or more locations of the medical care facility 106, such as Sharp Chula Vista.

FIG. 39 is another screen shot of the example reporting interface display 490 shown in FIG. 34. FIG. 39 illustrates the selection of billing as the report type, Sharp Chula Vista as the location, and Gil Ungab as the patient for the search criteria.

FIG. 40 is another screen shot of the example reporting interface display 490 shown in FIG. 34, and further illustrating the selection of one or more filters, such as the CPT codes.

FIG. 41 is another screen shot of the example reporting interface display 490 shown in FIG. 34, and further illustrating the selection of one or more CPT codes, such as Pacemaker (No programming evaluation) and AICD (no programming evaluation).

FIG. 42 is another screen shot of the example reporting interface display 490 shown in FIG. 34. FIG. 42 illustrates the selection of billing as the report type, Sharp Chula Vista as the location, Gil Ungab as the patient, and the selected CPT codes for the search criteria.

FIG. 43 is another screen shot of the example reporting interface display 490 shown in FIG. 34, and further illustrating the selection of one or more filters, such as the diagnosis codes.

FIG. 44 is another screen shot of the example reporting interface display 490 shown in FIG. 34, and further illustrating the selection of one or more diagnosis codes, such as Shortness of breath, Dizziness, and Palpitations.

FIG. 45 is another screen shot of the example reporting interface display 490 shown in FIG. 34. FIG. 45 illustrates the selection of billing as the report type, Sharp Chula Vista as the location, Gil Ungab as the patient, the selected CPT codes, and the selected Diagnosis codes for the search criteria.

FIG. 46 is another screen shot of the example reporting interface display 490 shown in FIG. 34, and further illustrating the selection of the time frame for with the search criteria is to be conducted, In this case, the search is to be conducted for reports created between Mar. 22, 2014 and Mar. 29, 2014. FIG. 46 also illustrates the selection of the report format, such as a pdf format.

FIG. 47 is another screen shot of the example reporting interface display 490 shown in FIG. 34. FIG. 47 illustrates the selection of billing as the report type, Sharp Chula Vista as the location, Gil Ungab as the patient, the selected CPT codes, the selected Diagnosis codes, the time frame for the document created, and the document format for the search criteria.

FIG. 48 illustrates an example billing report 500, such as generated by the reporting and analytics engine 158 of the interrogation data management system 140 shown in FIG. 4.

Additional analytics can be performed on data collected by the interrogation data management system 140. For example, analytics could be used to identify high risk populations. Physicians MP could then be alerted to the high risk patients P to ensure that proper care is being provided for those patients P. Examples of high risk populations may include those with atrial fibrillation and those at risk of stroke. Device manufacturer's can obtain this information from the interrogation data management system 140, for example, to permit manufacturer's representatives to contact the physicians MP managing those patients P.

ADDITIONAL CLAUSES

The foregoing detailed description describes a variety of possible embodiments to the present disclosure. For the sake of clarity, the following clauses identify some of these embodiments. Additional embodiments include combinations of these clauses, and further can be combined with any of the other embodiments described herein to arrive at further embodiments that are within the scope of the present disclosure.

Clause 1. A method of generating a report relating to an implantable cardiac device, the method being implemented by one or more computing devices, and comprising: receiving, using the one or more computing devices, an implantable cardiac device manufacturer's report associated with the implantable cardiac device; generating, using the one or more computing devices, a summary report from the implantable cardiac device manufacturer's report; generating, using the one or more computing devices, a reading physician note relating to the implantable cardiac device; and generating, using the one or more computing devices, a report relating to the implantable cardiac device, the report including the implantable cardiac device manufacturer's report, the summary report, and the reading physician note.

Clause 2. The method of clause 1, wherein the reading physician note comprises findings/interpretations and a conclusion.

Clause 3. The method of clause 1, wherein the implantable cardiac device manufacturer's report is a cardiac rhythm management company report.

Clause 4. The method of clause 1, wherein the report presents implantable cardiac device data in a clear and concise manner allowing one or more medical professionals to better treat and care for the patient with the implantable cardiac device.

Clause 5. The method of clause 1, wherein the summary report is a dashboard summary report.

Clause 6. A method of reviewing interrogation data of an implantable cardiac device, the method comprising: receiving the interrogation data of the implantable cardiac device; assigning, using a computing device, reading of the interrogation data to a first reader; and when the reading of the interrogation data by the first reader does not occur within a predetermined period of time, assigning reading of the interrogation data to a second reader.

Clause 7. The method of clause 6, further comprising: when the reading of the interrogation data to the second reader does not occur within a second predetermined period of time, assigning reading of the interrogation data to a third reader.

Clause 8. The method of clause 7, wherein the third reader is a reading panel.

Clause 9. The method of clause 8, wherein the reading panel includes one or more medical professionals that are designated to perform the reading of interrogation data for a medical facility when one or more assigned medical professionals do not complete the reading within designated time periods.

Clause 10. The method of clause 8, wherein the first reader is an ordering physician, and the second reader is a following physician.

Clause 11. The method of clause 6, further comprising alerting the first reader when the reading of the interrogation data is assigned to the first user, and further comprising alerting the first reader again before the predetermined period of time has elapsed.

Clause 12. The method of clause 11, further comprising alerting the second reader when the reading of the interrogation data is assigned to the second user, and further comprising alerting the second reader again before the second predetermined period of time has elapsed.

Clause 13. The method of clause 6, further comprising receiving inputs from a physician to complete a reading physician note after reading of the interrogation data has been completed by the second reader.

Clause 14. The method of clause 13, wherein the reading physician note is formally signed by the second reader as the reading physician.

Clause 15. The method of clause 14, wherein the reading physician note is electronically signed by the second reader.

Clause 16. The method of clause 13, further comprising generating and sending billing information for the second reader, the billing information being associated with the reading of the interrogation data by the second reader.

Clause 17. The method of clause 6, further comprising generating and sending billing information for a reading physician that completed the reading of the interrogation data.

Clause 18. The method of clause 6, wherein the assigning occurs automatically according to one or more rules.

Clause 19. The method of clause 18, wherein the assigning is based at least in part upon one or more of: a role of a physician, a qualification of a physician, an availability of a physician, an order of priority of readers, and a designation of a physician to a reading panel.

Clause 20. The method of clause 13, further comprising: storing the physicians notes in an electronic medical records system.

Clause 21. The method of clause 13, further comprising: receiving an implantable cardiac device manufacturer's report associated with the implantable cardiac device; generating a summary report from the implantable cardiac device manufacturer's report; and generating, using the one or more computing devices, a report relating to the implantable cardiac device, the report including the implantable cardiac device manufacturer's report, the summary report, and the reading physician note.

Clause 22. The method of clause 13, further comprising sending the report to an electronic medical records system.

Clause 23. A method of generating a reading physician's note associated with an implantable cardiac device, the method comprising: receiving an implantable cardiac device manufacturer's report containing device data associated with the implantable cardiac device; extracting the device data from the implantable cardiac device manufacturer's report; and using the device data to automatically populate one or more fields of the reading physician's note.

Clause 24. The method of clause 23, further comprising: presenting the reading physician's note to a reading physician for review, the physician's note including the one or more automatically populated fields; and receiving an electronic signature input from the reading physician for the reading physician's note.

Clause 25. The method of clause 24, further comprising: receiving additional information from the reading physician and updating the reading physician's note based on the additional information, and before receiving the electronic signature.

Clause 26. The method of clause 25, wherein receiving additional information from the reading physician comprises receiving selections from the physician from a set of predefined options.

Clause 27. The method of clause 25, wherein receiving additional information from the reading physician comprises receiving information into a free text entry field, wherein the free text entry field is associated with a particular category of information for the reading physician's note.

Clause 28. The method of clause 27, further comprising prompting the reading physician to select a status code associated with the free text entry field information.

Clause 29. The method of clause 27, wherein the status code is selected from normal, abnormal, and critically abnormal.

Clause 30. The method of clause 24, further comprising sending the physician's note to an electronic medical records system for storage in an electronic record associated with a patient with the implantable cardiac device.

Clause 31. The method of clause 24, sending billing information associated with a reading of the device data.

Clause 32. The method of clause 23, further comprising: generating a summary report from the extracted device data, and presenting the summary report to the physician before receiving the electronic signature input.

Clause 33. The method of clause 23, further comprising: presenting the implantable cardiac device manufacturer's report to the physician before receiving the electronic signature input.

Clause 34. The method of clause 23, wherein the physician's note is a formal record containing the reading physician's findings/interpretations and conclusions based on the reading physician's reading of the implantable cardiac device's device data.

Clause 35. The method of clause 34, wherein the physician's note comprises: device details, battery status, lead status, arrhythmia log, ventricular tachycardia (VT) therapies, magnet mode, and MRI safety.

Clause 36. The method of clause 35, wherein the physician's note further comprises a summary diagram graphically depicting status information in a summary form.

Clause 37. The method of clause 36, further comprising a timeline display graphically illustrating dates at which implantable cardiac device events occurred.

Clause 38. A method of electronically signing an implantable cardiac device report, the method comprising: receiving interrogation data at a server computing device associated with an implantable cardiac device; sending data from the server computing device to a remote computing device to generate a user interface for displaying the interrogation data to a physician; and receiving at the server computing device, and from the remote computing device, an input from the physician electronically signing the interrogation data.

Clause 39. The method of clause 38, wherein the data sent to the remote computing device comprises web page data, wherein the web page data is configured to generate a web page display through a browser software application running on the remote computing device.

Clause 40. The method of clause 38, wherein the data sent to the remote computing device comprises one or more messages configured to be received by an app running on the remote computing device, wherein the app generates a user interface to display the data to the physician.

Clause 41. A method of distributing interrogation data associated with implantable cardiac devices to a physician, the method comprising: receiving interrogation data associated with a first implantable cardiac device, the interrogation data identifying a first medical facility; receiving interrogation data associated with a second implantable cardiac device, the interrogation data identifying a second medical facility different than the first medical facility; and assigning reading of the interrogation data associated with the first and second implantable cardiac devices to a first physician.

Clause 42. The method of clause 41, wherein the first implantable cardiac device is manufactured by a first implantable cardiac device manufacturer and the second implantable cardiac device is manufactured by a second implantable cardiac device manufacturer.

Clause 43. A method of formally reviewing implantable cardiac device data, the method comprising: designating a physician as a reader; receiving implantable cardiac device data; and when the implantable cardiac device data is not read according to one or more predetermined criteria, assigning the implantable cardiac device data to be read by the designated reader using a computing device.

Clause 44. A system comprising: one or more processing devices; and one or more computer readable media, wherein the one or more computer readable media store data instructions, which when executed by the one or more processing devices cause the one or more processing devices to: receive an implantable cardiac device manufacturer's report associated with the implantable cardiac device; generate a summary report from the implantable cardiac device manufacturer's report; generate a reading physician note relating to the implantable cardiac device; and generate a report relating to the implantable cardiac device, the report including the implantable cardiac device manufacturer's report, the summary report, and the reading physician note.

Clause 45. A system comprising: one or more processing devices; and one or more computer readable media, wherein the one or more computer readable media store data instructions, which when executed by the one or more processing devices cause the one or more processing devices to: receive interrogation data of an implantable cardiac device; assign reading of the interrogation data to a first reader; and when the reading of the interrogation data by the first reader does not occur within a predetermined period of time, assign reading of the interrogation data to a second reader.

Clause 46. A system comprising: one or more processing devices; and one or more computer readable media, wherein the one or more computer readable media store data instructions, which when executed by the one or more processing devices cause the one or more processing devices to: receive an implantable cardiac device manufacturer's report containing device data associated with an implantable cardiac device; extract the device data from the implantable cardiac device manufacturer's report; and use the device data to automatically populate one or more fields of a reading physician's note.

Clause 47. A system comprising: one or more processing devices; and one or more computer readable media, wherein the one or more computer readable media store data instructions, which when executed by the one or more processing devices cause the one or more processing devices to: receive interrogation data associated with an implantable cardiac device; send data to a remote computing device to generate a user interface for displaying the interrogation data to a physician; and receive from the remote computing device an input from the physician electronically signing the interrogation data.

Clause 48. A system comprising: one or more processing devices; and one or more computer readable media, wherein the one or more computer readable media store data instructions, which when executed by the one or more processing devices cause the one or more processing devices to: receive interrogation data associated with a first implantable cardiac device, interrogation data identifying a first medical facility; receive interrogation data associated with a second implantable cardiac device, the interrogation data identifying a second medical facility different than the first medical facility; and assign reading of the interrogation data associated with the first and second implantable cardiac devices to a first physician.

Clause 49. A system comprising: one or more processing devices; and one or more computer readable media, wherein the one or more computer readable media store data instructions, which when executed by the one or more processing devices cause the one or more processing devices to: designate a physician as a reader; receive implantable cardiac device data; and when the implantable cardiac device data is not read according to one or more predetermined criteria, assign the implantable cardiac device data to be read by the designated reader.

Clause 50. Any one of the methods illustrated and/or described herein.

Clause 51. Any one of the systems illustrated and/or described herein.

Clause 52. A system comprising: one or more processing devices; and one or more computer readable media, wherein the one or more computer readable media store data instructions, which when executed by the one or more processing devices cause the one or more processing devices to execute any one or more of the engines illustrated and/or described herein.

The various embodiments described above are provided by way of illustration only and should not be construed to limit the claims attached hereto. Those skilled in the art will readily recognize various modifications and changes that may be made without following the example embodiments and applications illustrated and described herein, and without departing from the true spirit and scope of the following claims.

What is claimed is:

1. A medical device platform comprising:
    a memory storing computer-executable instructions; and
    a computing device executing the computer-executable instructions, wherein the instructions cause the computing device to:
        receive interrogation data transmitted from an implantable cardiac device located in a remote location, wherein the interrogation data from the implantable cardiac device is associated with a specific patient identifier, a specific intake time, and at least one of a plurality of implantable cardiac device manufacturers;
        based on receiving the interrogation data from the implantable cardiac device:
            generate a preliminary device interrogation report that includes a summary report and a reading physician note including a plurality of fields to receive analysis input in association with interrogation data, wherein generating the summary report and the reading physician note further causes the computing device to:
                determine in which one of a plurality of known vendor data formats the interrogation data exists;
                convert the interrogation data in the one known vendor data format to a common, manufacturer agnostic format to create consistent uniformity in data displayed to a reader regardless of a vendor of the implantable cardiac device; and
                populate one or more fields of each of the summary report and the reading physician note with the interrogation data in the common, manufacturer agnostic format; and
            determine a window of time for reading the preliminary device interrogation report based on the specific intake time;
            assign the reading of the preliminary device interrogation report to the reader according to a predetermined set of reading routing rules and send a reading alert to the reader to read the preliminary device interrogation report; and
            determine that the reading of the preliminary device interrogation report is completed within the window of time and, based on the determination that the preliminary device interrogation report has been read, generate a final device interrogation report based one or more inputs received in association with the reading of the preliminary device interrogation report.

2. The medical device platform of claim 1, wherein the computing device is further caused to determine that the reading of the preliminary device interrogation report is not completed within the window of time, and based on the determination that the reading has not been completed, determine a new window of time for reading the preliminary device interrogation report based on the specific intake time and assign the reading of the preliminary device interrogation report to a new reader or a reading panel, which comprises a plurality of readers, according to the predetermined set of reading routing rules.

3. The medical device platform of claim 1, wherein the reading alert comprises a first reading alert, and wherein the instructions further cause the computing device to send a second reading alert to the reader prior to determination that the reading of the preliminary device interrogation report is completed within the time window.

4. The medical device platform of claim 1, wherein the instructions further cause the computing device to determine that the preliminary device interrogation report is electronically signed and, based on the preliminary device interrogation report being signed, transmit billing information that is derived from reading physician note.

5. The medical device platform of claim 1, wherein the instructions further cause the computing device to determine that the preliminary device interrogation report is electronically signed and, based on the preliminary device interrogation report being signed, display a completed read status on a user interface of the medical device platform.

6. The medical device platform of claim 2, wherein the reader comprises an ordering physician and the new reader comprises a following physician.

7. The medical device platform of claim 1, wherein the reading routing rules are based upon one or more of: a role of a physician, a qualification of a physician, an availability of a physician, an order of priority of readers and a designation of a physician to a reading panel.

8. The medical device platform of claim 1, wherein the instructions further cause the computing device to:
    receive an implantable cardiac device manufacturer's report containing device data associated with the implantable cardiac device;
    extract the device data from the implantable device manufacturer's report; convert the extracted device data to the common manufacturer agnostic format; and populate at least one of the plurality of fields of the reading physician note with the converted device data.

9. The medical device platform of claim 8, wherein the instructions further cause the computing device to receive reader input to the reading physician note and receive an electronic signature to the reading physician note.

10. The medical platform of claim 8, wherein the reading physician note includes a status code field having a selectable status representative of the interrogation data.

11. The medical platform of claim 10, wherein the selectable status is selected from a normal status, an abnormal status, and a critically abnormal status.

12. The medical platform of claim 1,
    wherein the interrogation data comprises first interrogation data, wherein the implantable cardiac device comprises a first implantable cardiac device, wherein the preliminary device interrogation report comprises a first preliminary device interrogation report and wherein the first interrogation data identifies an association with a first medical facility, and
    wherein the instructions further cause the computing device to: receive second interrogation data associated with a second implantable cardiac device, the second interrogation data identifies an association with a second medical facility different from the first medical facility;
    generate a second preliminary device interrogation report; and assign reading of the first and second preliminary device interrogation reports to the same reader.

13. The medical platform of claim 12, wherein the first implantable cardiac device is manufactured by a first manufacturer and the second implantable cardiac device is manufactured by a second manufacturer that is different from the first manufacturer.

\* \* \* \* \*